US012475972B2

(12) United States Patent
Zhou et al.

(10) Patent No.: US 12,475,972 B2
(45) Date of Patent: Nov. 18, 2025

(54) PREDICTION SYSTEM FOR IDENTIFYING KEY HETEROGENEOUS MOLECULES DRIVING TUMOR METASTASIS

(71) Applicant: NANJING HANWEI PUBLIC HEALTH TECHNOLOGY CO., LTD., Nanjing (CN)

(72) Inventors: Jianwei Zhou, Nanjing (CN); Jiahua Cui, Nanjing (CN); Chuanjun Shu, Nanjing (CN); Junjie Chen, Nanjing (CN); Aiping Li, Nanjing (CN)

(73) Assignee: NANJING HANWEI PUBLIC HEALTH TECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 18/608,874

(22) Filed: Mar. 18, 2024

(65) Prior Publication Data

US 2024/0221867 A1 Jul. 4, 2024

Related U.S. Application Data

(63) Continuation-in-part of application No. PCT/CN2022/080847, filed on Mar. 15, 2022.

(30) Foreign Application Priority Data

Nov. 30, 2021 (CN) ......................... 202111444532.0

(51) Int. Cl.

*G16B 20/50* (2019.01)
*G01N 33/68* (2006.01)
*G16B 35/20* (2019.01)

(52) U.S. Cl.

CPC ......... *G16B 20/50* (2019.02); *G01N 33/6848* (2013.01); *G16B 35/20* (2019.02); *G01N 2800/52* (2013.01)

(58) Field of Classification Search

None

See application file for complete search history.

(56) References Cited

U.S. PATENT DOCUMENTS

| | | | |
|---|---|---|---|
| 2020/0225242 | A1 | 7/2020 | Haas et al. |
| 2021/0249101 | A1 | 8/2021 | Jain et al. |

FOREIGN PATENT DOCUMENTS

| | | | |
|---|---|---|---|
| CN | 107064519 | A | 8/2017 |
| CN | 107674919 | A | 2/2018 |
| CN | 109801680 | A | 5/2019 |
| CN | 111192638 | A | 5/2020 |
| CN | 114038504 | | 2/2022 |

*Primary Examiner* — G. Steven Vanni

(74) *Attorney, Agent, or Firm* — MATTHIAS SCHOLL P.C.; Matthias Scholl

(57) ABSTRACT

A prediction system for identifying key heterogeneous molecules that drive tumor metastasis including an input module, an analysis module, and an output module. The input module is configured to input a first quantitative analysis result of proteins and a second quantitative analysis result of proteins; the first quantitative analysis result of proteins is a collection of quantitative analysis results of various protein expression levels in tumor metastases of a target patient before drug intervention, and the second quantitative analysis result of proteins is a collection of quantitative analysis results of various protein expression levels in residual tumor metastases of the target patient after drug intervention. The analysis module includes a primary analysis submodule, a secondary analysis submodule, and a calculation and sorting submodule. The primary analysis submodule is used for preliminary screening analysis. The output module is used to output a sorted list of heterogeneous molecules.

10 Claims, 64 Drawing Sheets

| NO. | Gene Name | Description [Homo sapiens] | Fold change Animal model 1 JP3 + SP141 vs Vehicle |
|---|---|---|---|
| 1 | AGRN | agrin isoform 2 precursor | 0.98 |
| 2 | ANXA4 | annexin A4 isoform a | 0.99 |
| 3 | CFL1 | cofilin-1 | 0.98 |
| 4 | EEF2 | elongation factor 2 | 1.02 |
| 5 | ENO1 | alpha-enolase isoform 1 | 1.03 |
| 6 | EZR | ezrin | 1.03 |
| 7 | FASN | fatty acid synthase | 1.05 |
| 8 | GRP78 | 78 kDa glucose-regulated protein precursor | 0.95 |
| 9 | HNRNPK | heterogeneous nuclear ribonucleoprotein K isoform d | 1.04 |
| 10 | HSP90AB1 | heat shock protein HSP 90-beta isoform c | 0.99 |
| 11 | LDHA | L-lactate dehydrogenase A chain isoform 1 | 1.04 |
| 12 | NCL | nucleolin | 1.04 |
| 13 | NPM1 | nucleophosmin isoform 1 | 1.03 |
| 14 | PKM | pyruvate kinase PKM isoform a | 1.02 |
| 15 | PRDX1 | peroxiredoxin-1 | 1.03 |
| 16 | RAB1A | ras-related protein Rab-1A isoform 1 | 0.96 |
| 17 | SERPINH1 | serpin H1 precursor [Homo sapiens | 0.96 |
| 18 | SND1 | staphylococcal nuclease domain-containing protein 1 | 1.00 |
| 19 | SPTBN1 | spectrin beta chain, non-erythrocytic 1 isoform 1 | 1.03 |
| 20 | STIP1 | stress-induced-phosphoprotein 1 isoform b | 1.03 |
| 21 | TRAP1 | heat shock protein 75 kDa, mitochondrial isoform 2 | 1.02 |
| 22 | TUBB | tubulin beta chain isoform b | 1.03 |
| 23 | USP9X | probable ubiquitin carboxyl-terminal hydrolase FAF-X isoform 4 | 0.95 |
| 24 | VCP | transitional endoplasmic reticulum ATPase | 1.02 |
| 25 | VIM | vimentin | 1.05 |
| 26 | FSCN1 | fascin | 0.96 |
| 27 | GART | trifunctional purine biosynthetic protein adenosine-3 isoform 1 | 1.02 |
| 28 | HSP90B1 | endoplasmin precursor | 1.03 |
| 29 | HSPA9 | stress-70 protein, mitochondrial precursor | 0.97 |
| 30 | HSPB1 | heat shock protein beta-1 | 0.99 |
| 31 | HSPD1 | 60 kDa heat shock protein, mitochondrial | 1.05 |
| 32 | NUP98 | nuclear pore complex protein Nup98-Nup96 isoform 1 preproprotein | 1.04 |
| 33 | PCBP2 | poly(rC)-binding protein 2 isoform e | 1.00 |
| 34 | PFN1 | profilin-1 | 1.05 |
| 35 | PGAM1 | phosphoglycerate mutase 1 isoform 1 | 0.96 |
| 36 | PRDX4 | peroxiredoxin-4 precursor | 1.02 |
| 37 | SLC3A2 | 4F2 cell-surface antigen heavy chain isoform c | 1.02 |
| 38 | XPO1 | exportin-1 | 1.02 |

FIG. 14

| NO. | Name A | Stress A | Name C | Stress C |
|---|---|---|---|---|
| 1 | HSP90AB1 | 64 | ENO1 | 700 |
| 2 | HSPD1 | 42 | EEF2 | 502 |
| 3 | VCP | 18 | PKM | 474 |
| 4 | NPM1 | 18 | GRP78 | 404 |
| 5 | HSP90B1 | 10 | CFL1 | 296 |
| 6 | HSPA9 | 6 | HSPD1 | 294 |
| 7 | PKM | 4 | HSP90AB1 | 266 |
| 8 | ENO1 | 4 | HSPA9 | 220 |
| 9 | GRP78 | 2 | SPTBN1 | 206 |
| 10 | TUBB | 0 | PRDX1 | 198 |
| 11 | STIP1 | 0 | NPM1 | 168 |
| 12 | SPTBN1 | 0 | EZR | 162 |
| 13 | RAB1A | 0 | NCL | 156 |
| 14 | PGAM1 | 0 | HSPB1 | 142 |
| 15 | PCBP2 | 0 | LDHA | 142 |
| 16 | NCL | 0 | HNRNPK | 140 |
| 17 | LDHA | 0 | STIP1 | 136 |
| 18 | HNRNPK | 0 | TUBB | 84 |
| 19 | CFL1 | 0 | HSP90B1 | 76 |
| 20 | AGRN | 0 | TRAP1 | 72 |
| 21 | ANXA4 | 0 | XPO1 | 72 |
| 22 | EEF2 | 0 | VCP | 58 |
| 23 | EZR | 0 | PRDX4 | 44 |
| 24 | FASN | 0 | GART | 16 |
| 25 | PRDX1 | 0 | FSCN1 | 12 |
| 26 | SERPINH1 | 0 | PCBP2 | 12 |
| 27 | SND1 | 0 | SND1 | 8 |
| 28 | TRAP1 | 0 | SERPINH1 | 6 |
| 29 | USP9X | 0 | PGAM1 | 4 |
| 30 | VIM | 0 | ANXA4 | 0 |
| 31 | FSCN1 | 0 | VIM | 0 |
| 32 | GART | 0 | SLC3A2 | 0 |
| 33 | HSPB1 | 0 | FASN | 0 |
| 34 | NUP98 | 0 | RAB1A | 0 |
| 35 | PFN1 | 0 | NUP98 | 0 |
| 36 | PRDX4 | 0 | AGRN | 0 |
| 37 | SLC3A2 | 0 | USP9X | 0 |
| 38 | XPO1 | 0 | PFN1 | 0 |

FIG. 16

| Gene_Symbol | KEGG pathway |
|---|---|
| AGRN | ECM-receptor interaction |
| ANXA4 | NA |
| NUP98 | RNA transport; Influenza A; Amyotrophic lateral sclerosis |
| PFN1 | Amyotrophic lateral sclerosis |
| RAB1A | Amyotrophic lateral sclerosis; Pathways of neurodegeneration - multiple diseases; Autophagy - animal; Pathogenic Escherichia coli infection; Legionellosis |
| SLC3A2 | Protein digestion and absorption; mTOR signaling pathway; Ferroptosis |
| USP9X | NA |
| VIM | Epstein-Barr virus infection; MicroRNAs in cancer; Opioid receptor agonists/antagonists; beta-Lactam resistance; Protein processing in endoplasmic reticulum |
| FASN | Fatty acid metabolism; Metabolic pathways; Fatty acid biosynthesis; AMPK signaling pathway; Insulin signaling pathway |
| CFL1 | NA |
| EEF2 | Oxytocin signaling pathway; AMPK signaling pathway |
| ENO1 | HIF-1 signaling pathway |
| EZR | Sulfur relay system; Gastric acid secretion; Pathogenic Escherichia coli infection; Proteoglycans in cancer; MicroRNAs in cancer |
| FSCN1 | MicroRNAs in cancer |
| GART | Metabolic pathways; Purine metabolism; Biosynthesis of secondary metabolites; One carbon pool by folate; Antifolate resistance |
| GRP78 | NA |
| HNRNPK | Spliceosome; Viral carcinogenesis; MicroRNAs in cancer |
| HSP90AB1 | NA |
| HSP90B1 | NA |
| HSPA9 | NA |
| HSPB1 | MAPK signaling pathway; VEGF signaling pathway; Amoebiasis |
| HSPD1 | NA |
| LDHA | Pyruvate metabolism; Metabolic pathways; Microbial metabolism in diverse environments; HIF-1 signaling pathway; Central carbon metabolism in cancer |
| NCL | Pathogenic Escherichia coli infection |
| NPM1 | NA |
| PCBP2 | Ferroptosis |
| PGAM1 | NA |
| PKM | Central carbon metabolism in cancer; Glucagon signaling pathway |
| PRDX1 | Peroxisome; Amoebiasis |
| PRDX4 | NA |
| SERPINH1 | NA |
| SND1 | Viral carcinogenesis |
| SPTBN1 | NA |
| STIP1 | Prion disease |
| TRAP1 | Parkinson disease |
| TUBB | Pathways of neurodegeneration - multiple diseases |
| VCP | Amyotrophic lateral sclerosis; Pathways of neurodegeneration - multiple diseases; Protein processing in endoplasmic reticulum; Legionellosis |
| XPO1 | RNA transport; Ribosome biogenesis in eukaryotes; MAPK signaling pathway - fly; Influenza A; Human T-cell leukemia virus 1 infection |

FIG. 18

| NO. | Gene Name | Fold change Animal model 1 JP3 + SP141 vs Vehicle | Fold change Animal model 2 EGCG vs JP3 + SP141 |
|---|---|---|---|
| 1 | NUP98 | 1.04 | 1.01 |
| 2 | PFN1 | 1.05 | 0.99 |
| 3 | SLC3A2 | 1.02 | 0.99 |
| 4 | AGRN | 0.98 | 0.81 |
| 5 | ANXA4 | 0.99 | 1.12 |
| 6 | RAB1A | 0.96 | 1.14 |
| 7 | USP9X | 0.95 | undetermined |
| 8 | VIM | 1.05 | 0.88 |
FIG. 22
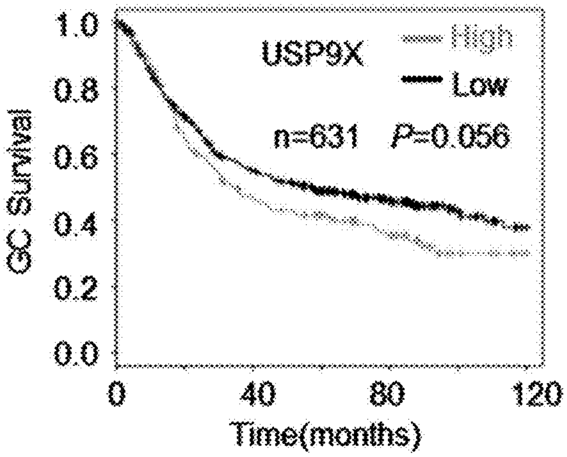
FIG. 23A
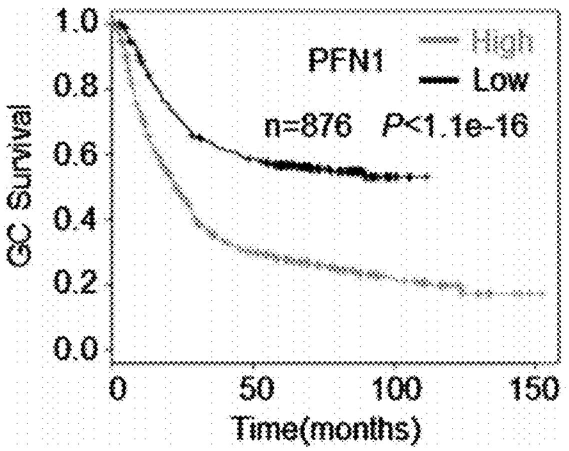
FIG. 23B

| NO. | Gene Name | Description |
|---|---|---|
| 1 | ARF1 | ADP-ribosylation factor 1 |
| 2 | BAG1 | BAG family molecular chaperone regulator 1 isoform 1S |
| 3 | BAG2 | BAG family molecular chaperone regulator 2 |
| 4 | BNIP3 | BCL2/adenovirus E1B 19 kDa protein-interacting protein 3 |
| 5 | CADM1 | cell adhesion molecule 1 isoform d precursor |
| 6 | CALR | calreticulin precursor |
| 7 | CBX4 | E3 SUMO-protein ligase CBX4 |
| 8 | CCND1 | G1/S-specific cyclin-D1 |
| 9 | CD2AP | CD2-associated protein |
| 10 | CDK1 | cyclin-dependent kinase 1 |
| 11 | CDK9 | cyclin-dependent kinase 9 |
| 12 | CUL4A | cullin-4A |
| 13 | FADS1 | fatty acid desaturase 1 |
| 14 | PGP | glycerol-3-phosphate phosphatase |
| 15 | GSK3B | glycogen synthase kinase-3 beta |
| 16 | GSTP1 | glutathione S-transferase P 1 |
| 17 | Hsp90b1 | endoplasmin precursor |
| 18 | HSPA5 | 78 kDa glucose-regulated protein precursor |

FIG. 33A

| NO. | Gene Name | Description |
|---|---|---|
| 19 | KHSRP | far upstream element-binding protein 2 |
| 20 | Map2k3 | dual specificity mitogen-activated protein kinase kinase 3 |
| 21 | Map2k4 | dual specificity mitogen-activated protein kinase kinase 4 isoform b |
| 22 | MEAF6 | chromatin modification-related protein MEAF6 isoform 2 |
| 23 | NEDD4 | E3 ubiquitin-protein ligase NEDD4 |
| 24 | PGD | 6-phosphogluconate dehydrogenase, decarboxylating |
| 25 | POLB | DNA polymerase beta |
| 26 | RNF181 | E3 ubiquitin-protein ligase RNF181 |
| 27 | TOP1 | DNA topoisomerase 1 |
| 28 | D54 | tumor protein D54 isoform c |
| 29 | H2AFX | histone H2AX |
| 30 | HSPA9 | stress-70 protein, mitochondrial |
| 31 | IDH1 | isocitrate dehydrogenase [NADP] cytoplasmic |
| 32 | IDH2 | isocitrate dehydrogenase [NADP], mitochondrial precursor |
| 33 | ITGA4 | integrin alpha-4 precursor |
| 34 | L2HGDH | L-2-hydroxyglutarate dehydrogenase, mitochondrial precursor |
| 35 | MCL1 | induced myeloid leukemia cell differentiation protein Mcl-1 homolog |
| 36 | MOB2 | MOB kinase activator 2 |

FIG. 33B

| NO. | Gene Name | Description |
|---|---|---|
| 37 | MTOR | serine/threonine-protein kinase mTOR |
| 38 | NDRG1 | protein NDRG1 |
| 39 | OAT | ornithine aminotransferase, mitochondrial precursor |
| 40 | PDIA3 | protein disulfide-isomerase A3 precursor |
| 41 | PDIA4 | protein disulfide-isomerase A4 precursor |
| 42 | PDIA6 | protein disulfide-isomerase A6 precursor |
| 43 | PFN1 | profilin-1 |
| 44 | PPIA | peptidyl-prolyl cis-trans isomerase A |
| 45 | RAC1 | ras-related C3 botulinum toxin substrate 1 precursor |
| 46 | ROCK2 | rho-associated protein kinase 2 |
| 47 | SMAD3 | mothers against decapentaplegic homolog 3 |
| 48 | SMC1A | structural maintenance of chromosomes protein 1A |
| 49 | SMC3 | structural maintenance of chromosomes protein 3 |
| 50 | SRSF3 | serine/arginine-rich splicing factor 3 |
| 51 | STUB1 | STIP1 homology and U box-containing protein 1 |
| 52 | TYR | tyrosinase isoform 1 precursor |
| 53 | UFC1 | ubiquitin-fold modifier-conjugating enzyme 1 |
| 54 | VCP | transitional endoplasmic reticulum ATPase |

FIG. 33C

| NO. | Name D | Stress D | Name E | Stress E | Name F | Stress F |
|---|---|---|---|---|---|---|
| 1 | SMAD3 | 200 | HSPA5 | 622 | MTOR | 934 |
| 2 | CDK9 | 198 | NEDD4 | 540 | CALR | 932 |
| 3 | STUB1 | 192 | STUB1 | 484 | HSPA5 | 814 |
| 4 | BAG2 | 182 | RAC1 | 452 | CDK1 | 810 |
| 5 | HSPA5 | 134 | H2AFX | 416 | H2AFX | 596 |
| 6 | CDK1 | 104 | BAG1 | 258 | MCL1 | 554 |
| 7 | CCND1 | 86 | BAG2 | 258 | VCP | 546 |
| 8 | H2AFX | 66 | SMAD3 | 258 | IDH1 | 450 |
| 9 | RAC1 | 12 | HSP90B1 | 206 | IDH2 | 450 |
| 10 | HSP90B1 | 2 | VCP | 166 | SMC1A | 444 |
| 11 | CALR | 2 | CDK9 | 148 | STUB1 | 444 |
| 12 | CBX4 | 0 | CCND1 | 146 | RAC1 | 436 |
| 13 | ARF1 | 0 | CALR | 126 | PDIA3 | 418 |
| 14 | NEDD4 | 0 | CDK1 | 112 | CCND1 | 256 |
| 15 | CADM1 | 0 | HSPA9 | 108 | BNIP3 | 256 |
| 16 | HSPA9 | 0 | GSK3B | 100 | PFN1 | 234 |
| 17 | BAG1 | 0 | SMC3 | 38 | HSPA9 | 174 |
| 18 | PDIA6 | 0 | MCL1 | 20 | HSP90B1 | 168 |
| 19 | PFN1 | 0 | CUL4A | 0 | PPIA | 98 |
| 20 | ROCK2 | 0 | PPIA | 0 | SMAD3 | 78 |
| 21 | GSK3B | 0 | CADM1 | 0 | SMC3 | 68 |
| 22 | IDH2 | 0 | ARF1 | 0 | BAG1 | 68 |
| 23 | IDH1 | 0 | CBX4 | 0 | NEDD4 | 58 |
| 24 | PDIA3 | 0 | PDIA6 | 0 | CDK9 | 30 |
| 25 | SMC1A | 0 | PFN1 | 0 | PDIA6 | 10 |
| 26 | SMC3 | 0 | ROCK2 | 0 | PDIA4 | 6 |
| 27 | BNIP3 | 0 | IDH2 | 0 | GSK3B | 4 |

FIG. 35A

| NO. | Name D | Stress D | Name E | Stress E | Name F | Stress F |
|---|---|---|---|---|---|---|
| 28 | CD2AP | 0 | IDH1 | 0 | BAG2 | 0 |
| 29 | CUL4A | 0 | PDIA3 | 0 | ROCK2 | 0 |
| 30 | FADS1 | 0 | SMC1A | 0 | ARF1 | 0 |
| 31 | PGP | 0 | BNIP3 | 0 | CBX4 | 0 |
| 32 | GSTP1 | 0 | CD2AP | 0 | CADM1 | 0 |
| 33 | KHSRP | 0 | FADS1 | 0 | KHSRP | 0 |
| 34 | MAPAK3 | 0 | PGP | 0 | SRSF3 | 0 |
| 35 | MAPAK4 | 0 | GSTP1 | 0 | PGD | 0 |
| 36 | MEAF6 | 0 | KHSRP | 0 | L2HGDH | 0 |
| 37 | PGD | 0 | MAPAK3 | 0 | TOP1 | 0 |
| 38 | POLB | 0 | MAPAK4 | 0 | OAT | 0 |
| 39 | RNF181 | 0 | MEAF6 | 0 | MOB2 | 0 |
| 40 | TOP1 | 0 | PGD | 0 | CUL4A | 0 |
| 41 | D54 | 0 | POLB | 0 | POLB | 0 |
| 42 | ITGA4 | 0 | RNF181 | 0 | NDRG1 | 0 |
| 43 | L2HGDH | 0 | TOP1 | 0 | CD2AP | 0 |
| 44 | MCL1 | 0 | D54 | 0 | FADS1 | 0 |
| 45 | MOB2 | 0 | ITGA4 | 0 | PGP | 0 |
| 46 | MTOR | 0 | L2HGDH | 0 | GSTP1 | 0 |
| 47 | NDRG1 | 0 | MOB2 | 0 | MAPAK3 | 0 |
| 48 | OAT | 0 | MTOR | 0 | MAPAK4 | 0 |
| 49 | PDIA4 | 0 | NDRG1 | 0 | MEAF6 | 0 |
| 50 | PPIA | 0 | OAT | 0 | RNF181 | 0 |
| 51 | SRSF3 | 0 | PDIA4 | 0 | D54 | 0 |
| 52 | TYR | 0 | SRSF3 | 0 | ITGA4 | 0 |
| 53 | UFC1 | 0 | TYR | 0 | TYR | 0 |
| 54 | VCP | 0 | UFC1 | 0 | UFC1 | 0 |

FIG. 35B

| Gene Name | KEGG pathway |
|---|---|
| ARF1 | Shigellosis; Phospholipase D signaling pathway; Pathogenic Escherichia coli infection; Endocytosis; Viral protein interaction with cytokine and cytokine receptor; Vibrio cholerae infection; Salmonella infection; Legionellosis; Epstein-Barr virus infection |
| BAG1 | Protein processing in endoplasmic reticulum |
| BAG2 | Protein processing in endoplasmic reticulum |
| BNIP3 | Mitophagy - animal; FoxO signaling pathway; Autophagy - animal; Shigellosis; Legionellosis |
| CADM1 | Cell adhesion molecules |
| CALR | Phagosome; Antigen processing and presentation; Protein processing in endoplasmic reticulum; Chagas disease; Human cytomegalovirus infection; Human T-cell leukemia virus 1 infection; Herpes simplex virus 1 infection; Epstein-Barr virus infection; Human immunodeficiency virus 1 infection; |
| CBX4 | NA |
| CCND1 | Pathways in cancer ;Breast cancer; Cellular senescence; Prolactin signaling pathway; Human cytomegalovirus infection; Non-small cell lung cancer; Gastric cancer; PI3K-Akt signaling pathway; Human papillomavirus infection; MicroRNAs in cancer; Hepatocellular carcinoma; Hedgehog signaling pathway; Human T-cell leukemia virus 1 infection; Viral carcinogenesis; |

FIG. 38A

| Gene Name | KEGG pathway |
|---|---|
| | Colorectal cancer; Glioma; Melanoma; Small cell lung cancer; Endocrine resistance; FoxO signaling pathway; p53 signaling pathway; Cell cycle; AMPK signaling pathway; Wnt signaling pathway; Apelin signaling pathway; Hippo signaling pathway; Focal adhesion; Tight junction; JAK-STAT signaling pathway; Thyroid hormone signaling pathway; Oxytocin signaling pathway; AGE-RAGE signaling pathway in diabetic complications; Cushing syndrome; Hepatitis C; Measles; Kaposi sarcoma-associated herpesvirus infection; Epstein-Barr virus infection; Proteoglycans in cancer; Pancreatic cancer; Endometrial cancer; Prostate cancer; Thyroid cancer; Bladder cancer; Chronic myeloid leukemia; Acute myeloid leukemia; Viral myocarditis |
| CD2AP | Bacterial invasion of epithelial cells |
| CDK1 | Oocyte meiosis; Progesterone-mediated oocyte maturation; Cell cycle; Cellular senescence; Human immunodeficiency virus 1 infection; Viral carcinogenesis; p53 signaling pathway; Gap junction; Transcriptional misregulation in cancer |
| CDK9 | Transcriptional misregulation in cancer |
| CUL4A | NA |
| FADS1 | Biosynthesis of unsaturated fatty acids; Fatty acid metabolism; Metabolic pathways |
| PGP | Metabolic pathways; Glycerophospholipid metabolism; Glyoxylate and dicarboxylate metabolism; Biosynthesis of secondary metabolites; Carbon metabolism; Purine metabolism; Biofilm formation - Escherichia coli; Biofilm formation - Pseudomonas aeruginosa; Biofilm formation - Vibrio cholerae |

FIG. 38B

| Gene Name | KEGG pathway |
|---|---|
| GSK3B | Hedgehog signaling pathway; Alzheimer disease; Insulin resistance; Pathways of neurodegeneration - multiple diseases; Axon guidance; Signaling pathways regulating pluripotency of stem cells; Human papillomavirus infection; Kaposi sarcoma-associated herpesvirus infection; Colorectal cancer; Gastric cancer; mTOR signaling pathway; EGFR tyrosine kinase inhibitor resistance; ErbB signaling pathway; Chemokine signaling pathway; Cell cycle; PI3K-Akt signaling pathway; Wnt signaling pathway ;Hedgehog signaling pathway - fly; Hippo signaling pathway; Focal adhesion; T cell receptor signaling pathway; IL-17 signaling pathway; B cell receptor signaling pathway; Circadian rhythm - fly; Neurotrophin signaling pathway; Dopaminergic synapse; Insulin signaling pathway; Melanogenesis; Prolactin signaling pathway; Thyroid hormone signaling pathway; Non-alcoholic fatty liver disease; Cushing syndrome; Growth hormone synthesis, secretion and action; Prion disease; Shigellosis; Yersinia infection; Hepatitis C; Measles; Human cytomegalovirus infection; Pathways in cancer; Endometrial cancer; Prostate cancer; Basal cell carcinoma; Breast cancer; Hepatocellular carcinoma; Lipid and atherosclerosis; Diabetic cardiomyopathy |
| GSTP1 | Prostate cancer; Pathways in cancer |
| Hsp90b1 | NA |
| HSPA5 | Prion disease; Pathways of neurodegeneration - multiple diseases; Protein export; Protein processing in endoplasmic reticulum; Antigen processing and presentation; Thyroid hormone synthesis; Parkinson disease; Amyotrophic lateral sclerosis; Lipid and atherosclerosis; Dopaminergic synapse; Insulin signaling pathway; Melanogenesis; Prolactin signaling pathway; Thyroid hormone signaling pathway; Non-alcoholic fatty liver disease; Cushing syndrome; Growth hormone synthesis, secretion and action; Prion disease; Shigellosis; Yersinia infection; Hepatitis C; Measles; Human cytomegalovirus infection |
| KHSRP | NA |
| Map2k3 | TNF signaling pathway; Lipid and atherosclerosis; MAPK signaling pathway; MAPK signaling |

FIG. 38C

| Gene Name | KEGG pathway |
|---|---|
| | pathway - fly; Rap1 signaling pathway; Cellular senescence; Toll-like receptor signaling pathway; Toll and Imd signaling pathway; Fc epsilon RI signaling pathway; Thermogenesis; Inflammatory mediator regulation of TRP channels; GnRH signaling pathway; Growth hormone synthesis, secretion and action; Amyotrophic lateral sclerosis; Pathways of neurodegeneration - multiple diseases; Salmonella infection; Yersinia infection; Toxoplasmosis; Hepatitis B; Epstein-Barr virus infection; PD-L1 expression and PD-1 checkpoint pathway in cancer; Human immunodeficiency virus 1 infection |
| Map2k4 | Hepatitis B; Lipid and atherosclerosis; Fluid shear stress and atherosclerosis; MAPK signaling pathway; ErbB signaling pathway; MAPK signaling pathway - fly; Axon regeneration; Toll-like receptor signaling pathway; Fc epsilon RI signaling pathway; TNF signaling pathway; GnRH signaling pathway; Relaxin signaling pathway; Growth hormone synthesis, secretion and action; Epithelial cell signaling in Helicobacter pylori infection; Salmonella infection; Yersinia infection; Chagas disease; Human T-cell leukemia virus 1 infection; Kaposi sarcoma-associated herpesvirus infection; Epstein-Barr virus infection |
| MEAF6 | NA |
| NEDD4 | Aldosterone-regulated sodium reabsorption; Ubiquitin mediated proteolysis; Tight junction; Endocytosis; Epstein-Barr virus infection; MAPK signaling pathway - yeast |
| PGD | Pentose phosphate pathway; Carbon metabolism; Microbial metabolism in diverse environments; Fc epsilon RI signaling pathway; African trypanosomiasis |
| POLB | Base excision repair; DNA replication; Human T-cell leukemia virus 1 infection; Viral carcinogenesis |
| RNF181 | NA |
| TOP1 | NA |

FIG. 38D

| Gene Name | KEGG pathway |
|---|---|
| D54 | NA |
| H2AFX | NA |
| HSPA9 | NA |
| IDH1 | 2-Oxocarboxylic acid metabolism; Metabolic pathways; Microbial metabolism in diverse environments; Carbon metabolism; Citrate cycle (TCA cycle); Biosynthesis of secondary metabolites; Biosynthesis of amino acids; Central carbon metabolism in cancer; Glutathione metabolism; Carbon fixation pathways in prokaryotes; Peroxisome |
| IDH2 | NA |
| ITGA4 | Cell adhesion molecules; Leukocyte transendothelial migration; ECM-receptor interaction; Intestinal immune network for IgA production; PI3K-Akt signaling pathway; Focal adhesion; Hematopoietic cell lineage; Regulation of actin cytoskeleton; Yersinia infection; Leishmaniasis; Human papillomavirus infection; Hypertrophic cardiomyopathy; Arrhythmogenic right ventricular cardiomyopathy; Dilated cardiomyopathy |
| L2HGDH | Butanoate metabolism; Metabolic pathways |
| MCL1 | Apoptosis; JAK-STAT signaling pathway; MicroRNAs in cancer; PI3K-Akt signaling pathway |
| MOB2 | NA |
| MTOR | mTOR signaling pathway; Phospholipase D signaling pathway; Longevity regulating pathway; Insulin resistance; Hepatocellular carcinoma; Insulin signaling pathway; Adipocytokine signaling pathway; Type II diabetes mellitus; Longevity regulating pathway - multiple species; Glioma; Cellular senescence; Breast cancer; Autophagy - animal;PI3K-Akt signaling pathway; |

FIG. 38E

| Gene Name | KEGG pathway |
|---|---|
| | Thermogenesis; EGFR tyrosine kinase inhibitor resistance; ErbB signaling pathway; HIF-1 signaling pathway; AMPK signaling pathway; Longevity regulating pathway - worm; Apelin signaling pathway; Axon regeneration; Thyroid hormone signaling pathway; Human cytomegalovirus infection; Human papillomavirus infection; Human immunodeficiency virus 1 infection; Pathways in cancer; Proteoglycans in cancer; Colorectal cancer; Acute myeloid leukemia; Gastric cancer; Central carbon metabolism in cancer; Choline metabolism in cancer;PD-L1 expression and PD-1 checkpoint pathway in cancer; Diabetic cardiomyopathy; Autophagy - yeast; Endocrine resistance; Neutrophil extracellular trap formation; JAK-STAT signaling pathway;Th17 cell differentiation; Growth hormone synthesis, secretion and action; Alzheimer disease; Amyotrophic lateral sclerosis; Huntington disease; Spinocerebellar ataxia; Shigellosis; Pathways of neurodegeneration - multiple diseases; Kaposi sarcoma-associated herpesvirus infection; Herpes simplex virus 1 infection; Pancreatic cancer |
| NDRG1 | NA |
| OAT | NA |
| PDIA3 | Protein processing in endoplasmic reticulum; Antigen processing and presentation; Human cytomegalovirus infection; Herpes simplex virus 1 infection; Epstein-Barr virus infection; Human immunodeficiency virus 1 infection |
| PDIA4 | Protein processing in endoplasmic reticulum; Thyroid hormone synthesis; Vibrio cholerae infection |
| PDIA6 | Protein processing in endoplasmic reticulum |
| PFN1 | Amyotrophic lateral sclerosis |
| PPIA | Cationic antimicrobial peptide (CAMP) resistance; Necroptosis |

FIG. 38F

| Gene Name | KEGG pathway |
|---|---|
| RAC1 | Shigellosis; Wnt signaling pathway; Axon guidance; Adherens junction; Lipid and atherosclerosis; Ras signaling pathway; Tight junction; Leukocyte; Amyotrophic lateral sclerosis; Pathways of neurodegeneration - multiple diseases; Epithelial cell signaling in Helicobacter pylori infection; Kaposi sarcoma-associated herpesvirus infection; Epstein-Barr virus infection; Renal cell carcinoma; MAPK signaling pathway; MAPK signaling pathway - fly; cAMP signaling pathway; Chemokine signaling pathway; Sphingolipid signaling pathway; Axon regeneration; VEGF signaling pathway; Focal adhesion; Neutrophil extracellular trap formation; Natural killer cell mediated cytotoxicity; B cell receptor signaling pathway; Fc epsilon RI signaling pathway; Fc gamma R-mediated phagocytosis; Prion disease; Human immunodeficiency virus 1 infection; Human cytomegalovirus infection; Viral carcinogenesis; Colorectal cancer; Choline metabolism in cancer transendothelial migration; Pathogenic Escherichia coli infection; Salmonella infection; Proteoglycans in cancer; Yersinia infection;Rap1 signaling pathway; Phagosome; Bacterial invasion of epithelial cells; Pathways in cancer; Pancreatic cancer; PI3K-Akt signaling pathway; Osteoclast differentiation; Toll-like receptor signaling pathway; Regulation of actin cytoskeleton; Neurotrophin signaling pathway; Non-alcoholic fatty liver disease; AGE-RAGE signaling pathway in diabetic complications; Pancreatic secretion |
| ROCK2 | Axon guidance; Tight junction; Leukocyte transendothelial migration; Wnt signaling pathway; Lipid and atherosclerosis; cGMP-PKG signaling pathway; cAMP signaling pathway; Chemokine signaling pathway; Sphingolipid signaling pathway; Vascular smooth muscle contraction; Focal adhesion; Platelet activation; Regulation of actin cytoskeleton; Oxytocin signaling pathway; Pathogenic Escherichia coli infection; Shigellosis; Salmonella infection; Yersinia infection; Human cytomegalovirus infection; Pathways in cancer;;Proteoglycans in cancer |
| SMAD3 | TGF-beta signaling pathway; Hepatitis B; FoxO signaling pathway; Hippo signaling pathway; |

FIG. 38G

| Gene Name | KEGG pathway |
|---|---|
| | Signaling pathways regulating pluripotency of stem cells;Th17 cell differentiation; Wnt signaling pathway; Adherens junction; Chronic myeloid leukemia; Cell cycle; Endocytosis; Cellular senescence; Apelin signaling pathway; AGE-RAGE signaling pathway in diabetic complications; Human T-cell leukemia virus 1 infection; Pathways in cancer; Colorectal cancer; Pancreatic cancer; Hepatocellular carcinoma; Gastric cancer; Diabetic cardiomyopathy; Inflammatory bowel disease |
| SMC1A | NA |
| SMC3 | Meiosis - yeast; Oocyte meiosis; Cell cycle; Cell cycle - yeast; Proteasome; Alzheimer disease; Parkinson disease; Amyotrophic lateral sclerosis; Huntington disease; Spinocerebellar ataxia; Prion disease; Pathways of neurodegeneration - multiple diseases; Epstein-Barr virus infection |
| SRSF3 | NA |
| STUB1 | Protein processing in endoplasmic reticulum; Ubiquitin mediated proteolysis |
| TYR | Melanogenesis |
| UFC1 | Oxidative phosphorylation; Metabolic pathways; Thermogenesis; Retrograde endocannabinoid signaling; Non-alcoholic fatty liver disease; Alzheimer disease; Parkinson disease; Amyotrophic lateral sclerosis; Huntington disease; Prion disease; Pathways of neurodegeneration - multiple diseases; Diabetic cardiomyopathy |
| VCP | Amyotrophic lateral sclerosis; Pathways of neurodegeneration - multiple diseases; Protein processing in endoplasmic reticulum; Legionellosis |

FIG. 38H

| Abbreviation | Gene name |
|---|---|
| AGRN | Agrin |
| ANXA4 | Annexin A4 |
| NUP98 | Precursor of nuclear pore proteins 98 and 96 |
| PFN1 | Profilin 1 |
| RAB1A | RAS oncogene family member RAB1A |
| SLC3A2 | Member 2 of Solute carrier family 3 |
| USP9X | x-linked ubiquitin-specific peptidase 9 |
| VIM | vimentin |
| FASN | Fatty acid synthase |
| CFL1 | Cofilin 1 |
| EEF2 | Eukaryotic translation elongation factor |
| ENO1 | Enolase-1 |
| EZR | Ezrin |
| FSCN1 | Actin-binding protein 1 |
| GART | Phosphoribosylceramide transcarboxylase |
| GRP78 | G protein-coupled receptor 78 |
| HNRNPK | Nuclear heterogeneity ribonucleoprotein K |
| HSP90AB1 | 90kDa heat shock protein αβ1 |
| HSP90B1 | 90kDa heat shock protein β1 |
| HSPA9 | 70KDA heat shock protein 9 |
| HSPB1 | Member 1 of Heat shock protein family B |
| HSPD1 | Member 1 of Heat shock protein family D (Hsp60) |
| LDHA | Lactate dehydrogenase |
| NCL | Nucleolin |
| NPM1 | Nuclear phosphoprotein 1 |
| PCBP2 | Polycytidyne-binding protein 2 |
| PGAM1 | Phosphoglycerate translocase 1 |
| PKM | M-type pyruvate kinase |
| PRDX1 | Peroxiredoxin 1 |
| PRDX4 | Peroxiredoxin 4 |

FIG. 42A

| Abbreviation | Gene name |
|---|---|
| SERPINH1 | Serine protease inhibitor H1 |
| SND1 | Staphylococcal nuclease structural domain 1 |
| SPTBN1 | spectrin β1 |
| STIP1 | Stress-inducible phosphoprotein 1 |
| TRAP1 | Tumor necrosis factor receptor-related protein 1 |
| TUBB | Microtubule protein β-microtubule protein |
| VCP | Valerian casein-containing proteins |
| XPO1 | Nuclear export protein 1 |
| ARF1 | ADP nuclear glycosylation factor 1 |
| BAG1 | Bcl-2-associated athanogene 1 |
| BAG2 | Bcl-2-associated athanogene 2 |
| BNIP3 | BCL2/Adenovirus E1B Interaction Protein 3 |
| CADM1 | Cell adhesion molecule 1 |
| CALR | Calreticulin |
| CBX4 | Polychrome box homologue 4 |
| CCND1 | Cell cycle protein D1 |
| CD2AP | CD2-related protein |
| CDK1 | Cyclin-dependent kinase 1 |
| CDK9 | Cyclin-dependent kinase 9 |
| CUL4A | Ubiquitin-proteasome system 4A |
| FADS1 | Fatty acid desaturase 1 |
| PGP | Osmotic glycoprotein |
| GSK3B | Glycogen synthase kinase 3β |
| GSTP1 | Glutathione sulfotransferase P1 |
| HSPA5 | Heat shock protein family A (Hsp70) member 5 |
| KHSRP | Shear-type regulatory protein |
| Map2k3 | Mitogen-activated protein kinase 3 |
| Map2k4 | Mitogen-activated protein kinase 4 |
| MEAF6 | MYST/ Esa1-associated factor 6 |
| NEDD4 | Neural precursor cell expression and developmental down-regulation factors 4 |
| PGD | Phosphogluconate dehydrogenase |
| POLB | DNA guide polymerase beta |

FIG. 42B

| Abbreviation | Gene name |
|---|---|
| RNF181 | Silencing ring finger protein 181 |
| TOP1 | Topoisomerase I |
| D54 | Tumor protein D54 |
| H2AFX | H2A histone family member X |
| IDH1 | Isocitrate dehydrogenase-1 |
| IDH2 | Isocitrate dehydrogenase-2 |
| ITGA4 | Integrin a4 |
| L2HGDH | l-2-hydroxyglutarate dehydrogenase |
| MCL1 | Bcl2-related myeloid leukemia sequence 1 |
| MOB2 | MOB family protein 2 |
| MTOR | Rapamycin target protein |
| NDRG1 | N-myc downstream regulated gene 1 |
| OAT | Ornithine transaminase |
| PDIA3 | Protein disulfide bond isomerase A3 |
| PDIA4 | Protein disulfide isomerase A4 |
| PDIA6 | Protein disulfide isomerase A6 |
| PPIA | Peptidyl prolyl isomerase A |
| RAC1 | Small GTP-binding protein RAC1 |
| ROCK2 | Serine/threonine kinase |
| SMAD3 | SMAD homolog 3 |
| SMC1A | Structural maintenance of chromosome protein 1A |
| SMC3 | Structural maintenance of chromosome protein 3 |
| SRSF3 | Serine- and arginine-rich splicing factor 3 |
| STUB1 | STIP1 homolog and U-Box containing protein 1 |
| TYR | Tyrosinase-related protein family |
| UFC1 | Ubiquitin folding modification conjugating enzyme 1 |

FIG. 42C

PREDICTION SYSTEM FOR IDENTIFYING KEY HETEROGENEOUS MOLECULES DRIVING TUMOR METASTASIS

CROSS-REFERENCE TO RELATED APPLICATIONS

This application is a continuation-in-part of International Patent Application No. PCT/CN2022/080847 with an international filing date of Mar. 15, 2022, designating the United States, and further claims foreign priority benefits to Chinese Patent Application No. 202111444532.0 filed Nov. 30, 2021. The contents of all of the aforementioned applications, including any intervening amendments thereto, are incorporated herein by reference.

BACKGROUND

The disclosure relates to the field of pharmaceutical biotechnology, and more particularly to a prediction system for identifying key heterogeneous molecules driving tumor metastasis.

Malignant tumors are a major public health problem having a detrimental effect on human health. Tumor drug resistance and metastasis are one of the underlying causes of low survival rates and death in tumor patients. The biggest challenge facing tumor therapy is how to overcome tumor drug resistance and metastasis resulting from tumor heterogeneity. Although new approaches including biotherapies and immunotherapies have brought hope to tumor treatment, the treatment targets a single site, and tumor heterogeneity leads to difficulty in completely conquering the tumor. Even if there is some efficacy in the early stages of treatment, tumor cell drug resistance or metastasis often occurs after a period of time, rendering the treatment ineffective. Since heterogeneous tumor cell subpopulations are independent of each other, even if an effective intervention can be taken against an oncogene or cancer suppressor gene, other heterogeneous molecules will not be affected at the same time; these heterogeneous tumor cell subpopulations will play a dominant role in adapting to the host environment when the conditions are suitable, and further drive the occurrence of tumor metastasis.

That tumor drug resistance and metastasis driven by heterogeneous molecules lead to tumor progression is a consensus in the field of cancer research. However, most studies are still searching for differentially expressed molecules and proving their exact upstream and downstream regulatory networks and mechanisms. There is currently no method to accurately identify heterogeneous molecules of tumors in individual patients. It is urgent to develop technical means that can accurately identify heterogeneous molecules of tumors in individual patients.

There are certain prediction systems in the related art, for example, a system based on lncRNA molecular model to predict the efficacy and prognosis of neoadjuvant chemoradiotherapy for esophageal squamous cell carcinoma patients. The system is directed to detect the expression levels of three lncRNAs: SCAT1, PRKAG2-AS1, and FLG-AS1, to predict the efficacy of neoadjuvant chemoradiotherapy for esophageal squamous cell carcinoma patients, and also to predict the prognosis of esophageal squamous cell carcinoma patients, such as overall prognostic survival and relapse-free survival. However, there has not yet been a technical solution aimed at discovering and guiding tumor treatment interventions with technical effects.

SUMMARY

One objective of the disclosure is to overcome the problems in the prior art, and provide a prediction system for identifying key heterogeneous molecules driving tumor metastasis. Based on the quantitative analysis results of proteins of metastatic tumor tissues before and after tumor treatment, combined with bioinformatics and computational biology methods, a list of tumor heterogeneous molecules was screened, sorted, and determined. The system can effectively identify the heterogeneous molecules driving tumor metastasis in different patients, providing precise guidance for individualized treatment plans for tumor metastasis.

The disclosure provides a prediction system for identifying key heterogeneous molecules driving tumor metastasis, the system comprising: an input module, an analysis module, and an output module.

The input module is configured to input a first quantitative analysis result of proteins and a second quantitative analysis result of proteins;

- the first quantitative analysis result of proteins is a collection of quantitative analysis results of various protein expression levels in tumor metastases of a target patient before drug intervention, and the second quantitative analysis result of proteins is a collection of quantitative analysis results of various protein expression levels in residual tumor metastases of the target patient after drug intervention;
- the analysis module comprises a primary analysis submodule, a secondary analysis submodule, and a calculation and sorting submodule;
- the primary analysis submodule is used for preliminary screening analysis; the preliminary screening analysis comprises comparing the first quantitative analysis result of proteins and the second quantitative analysis result of proteins, and including proteins with expression changes within a predetermined range in a candidate protein set;
- the secondary analysis submodule is used for secondary screening analysis; the secondary screening analysis comprises constructing, using a protein interaction network analysis tool, experimentally validated protein interaction networks based on the candidate protein set, supplementing the protein interaction networks by utilizing signal pathways involved in the candidate protein set in a signal pathway database; including most important proteins in each protein interaction network as independent heterogeneous molecules in an independent molecular set; constructing, using a protein interaction network prediction tool and based on the candidate protein set, a protein interaction prediction network according to a protein interaction law; and including proteins in the candidate protein set that do not participate in any protein interaction prediction network as independent heterogeneous molecules in the independent molecular set;
- the calculation and sorting submodule is used for calculating and sorting; the calculating and sorting comprises calculating a hazard ratio (HR) value of each heterogeneous molecule in the independent molecular set, sorting the heterogeneous molecule based on the HR value, to form a sorting list of each heterogeneous molecule; and the output module is used to output a sorted list of heterogeneous molecules.

Practical researches show that accurate identification of new heterogeneous targets driving tumor metastasis and timely intervention can overcome tumor drug resistance and metastasis driven by heterogeneous molecules, effectively control tumor progression, and prolong patient life before tumor cells fully adapt to a current treatment plan. The key to driving tumor metastasis or recurrence lies in the heterogeneous molecules that are not controlled by current drugs but closely related to tumor progression. If precise intervention can be implemented against the heterogeneous molecules in residual tumor foci, perhaps the problem of tumor drug resistance and metastasis recurrence driven by heterogeneous molecules can be solved.

Through the prediction system of the disclosure, relevant proteins in tumor metastases before and after intervention are first screened, and then further screened through bioinformatics and computational biology methods. The "importance" of the heterogeneous molecules driving tumor metastasis is ranked to determine the theoretical intervention order of target molecules. The prediction system can accurately identify heterogeneous molecules driving tumor metastasis, providing precise intervention strategies for effectively suppressing tumor drug resistance and metastasis driven by heterogeneous molecules.

In a class of this embodiment, the first quantitative analysis result of proteins and the second quantitative analysis result of proteins are acquired through high-throughput protein sequencing; and the high-throughput protein sequencing comprises protein mass spectrometry analysis.

Through the technical solution, the specific details of obtaining quantitative analysis results of proteins can be further optimized.

In a class of this embodiment, during the preliminary screening analysis, the proteins with expression changes within a predetermined range are proteins whose expression levels after drug intervention are 0.95-1.05 times higher than those before drug intervention.

In a class of this embodiment, during the preliminary screening analysis, the proteins with expression changes within the predetermined range are first screened and then included in the candidate protein set; the proteins that are screened meet the following conditions: a number of specific peptide segments is ≥2, and is not a prediction protein; a coverage of amino acids of identified peptide segments of a current protein is ≥10%; a quantification frequency of the current protein is ≥2, and a sequencing quality comprehensive score of the current protein is ≥200; evidence in a database shows the current protein is related to tumor progression; the specific peptide segments refer to a specific peptide segment used to identify the current protein; the prediction protein refers to an attribute that defines a reliability of the current protein in Uniport or NCBI databases as a prediction protein; the identified peptide segments refer to a specific peptide segment that can be used to indicate the current protein being detected; the quantification frequency of the current protein refers to a number of repetitions of the current protein being quantitatively detected.

Through the technical solution, the specific details of the preliminary screening analysis of the primary analysis submodule can be further optimized.

In a class of this embodiment, during the secondary screening analysis, the protein interaction network analysis tool comprises a STRING network tool; the signal pathway database comprises KEGG, SMPDB, WikiPathways, Cell Signaling Technology, BioCarta Pathway, Pathway Commons, and PID; the protein interaction network prediction tool comprises a Genemania network tool, Unihi network tool, and Hitpredict network tool.

In a class of this embodiment, a Cytoscape tool is employed to construct and supplement the protein interaction networks, and to construct the protein interaction prediction network.

In a class of this embodiment, during the secondary screening analysis, the most important proteins in each protein interaction network are identified through characteristic analysis; the characteristic analysis comprises analyzing the importance, degree, and radiancy of each protein in the protein interaction network; and proteins with the highest importance, degree, and radiancy are the most important proteins in the protein interaction network.

Through the technical solution, the specific details of the secondary analysis submodule can be further optimized for further screening and analysis.

In a class of this embodiment, during the calculating and sorting, the HR value of each heterogeneous molecule is calculated as follows: obtaining sequencing data of tumors from a public database, obtaining a standardized counting matrix of genes corresponding to the heterogeneous molecules from the sequencing data, and performing batch single factor COX regression on the genes to obtain the HR value.

In a class of this embodiment, the public database comprises TCGA, ICGC, and GEO.

In a class of this embodiment, during the calculating and sorting, a sorting rule is: the heterogeneous molecules with HR values greater than or equal to 1 are directly sorted in reverse order according to their HR values, and the heterogeneous molecules with HR values less than 1 are sorted in reverse order according to their 1/HR values.

Through the technical solution, the calculation and sorting of the calculation and sorting submodule are optimized.

In another aspect, the disclosure also provides a sequential intervention system for executing a sequential intervention order of heterogeneous molecules driving tumor metastasis. The sequential intervention system comprises the abovementioned prediction system for identifying key heterogeneous molecules driving tumor metastasis, and an execution module. The execution module is used to determine the sequential intervention order based on the sorting list of heterogeneous molecules output by the prediction system and a predetermined rule. The predetermined rule refers to the selection and ranking rules determined by users based on actual situations (such as certain heterogeneous molecules without inhibitors or agonists, or unreachable drugs due to high prices), making the sequential intervention sequence more in line with the actual situation.

The following advantages are associated with the prediction system for identifying key heterogeneous molecules driving tumor metastasis of the disclosure:

(1) Uniqueness: compared to other identification and analysis methods, the prediction system of the disclosure focuses on targets with mutations, variants, and abnormal expression, the prediction system is able to identify and screen heterogeneous molecules with stable protein expression in tumor metastases before and after drug intervention, and with the potential to drive tumor metastasis.

(2) Practicality: sequential intervention validation studies of the heterogeneous molecules predicted and screened by the disclosure are carried out in gastric cancer and melanoma respectively, and the expected results are obtained, indicating that the heterogeneous molecules and the sequential intervention strategy of the disclosure are correct and feasible.

(3) Effectiveness: the results of the validation studies on the heterogeneous molecules in gastric cancer and melanoma show that each additional intervention of a heterogeneous molecule significantly improves the outcome or prolongs the survival time of the model mice, which indicates that the heterogeneous molecules identified and predicted by the disclosure are indeed able to independently drive the metastasis of gastric cancer or melanoma; the implementation of sequential interventions in accordance with the order of heterogeneous molecules identified by the method of the disclosure combined with the actual situation can effectively overcome the tumor drug resistance and recurrence of tumor metastasis caused by the heterogeneous molecules.

In summary, the prediction system can reasonably and accurately identify the key heterogeneous molecules driving tumor metastasis and rank the key heterogeneous molecules, and then carry out sequential interventions according to the results in combination with the actual situation, and the therapeutic efficacy is certain. The findings and evidences provide innovative ideas, specific algorithms and practical guidance for the clinical treatment of drug-resistant and metastatic tumors due to tumor heterogeneity.

BRIEF DESCRIPTION OF THE DRAWINGS

FIGS. 12-18 show results of identifying other heterogeneous molecules driving gastric cancer metastasis after joint intervention on JWA and MDM2 in operations 1.4 of Example 1 of the disclosure;

FIGS. 22 and 23A-23B show how the sequential interventions on JWA, MDM2, and FASN can further identify other heterogeneous molecules in gastric cancer driving metastasis in operations 1.6 of Example 1 of the disclosure;

FIGS. 32, 33A-33C, 34A-34D, 35A-35B, 36, 37, 38A-38H, and 39A-39B show how to identify heterogeneous molecules driving melanoma metastasis after joint intervention on JWA and MDM2 in operations 2.4 of Example 2 of the disclosure;

FIGS. 42A-42C shows the abbreviations and corresponding English names of the main genes involved in the disclosure.

DETAILED DESCRIPTION

Figure 1A:
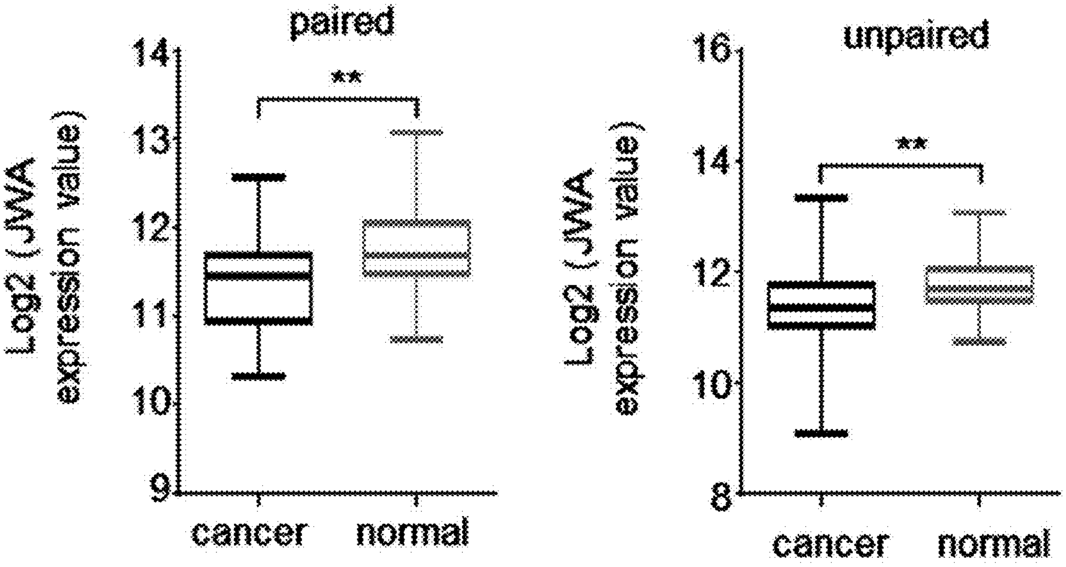
FIGS. 1A-1B, 2A-2D, 3A-3D, and 4A-4B show a relationship between the tumor suppressor gene JWA and the prognosis and metastasis characteristics of gastric cancer in operations 1.1 of Example 1 of the disclosure.

Specifically, the disclosure provides a prediction system for identifying key heterogeneous molecules driving tumor metastasis, the system comprising an input module, an analysis module, and an output module.

The input module is configured to input a first quantitative analysis result of proteins and a second quantitative analysis result of proteins; the first quantitative analysis result of proteins is a collection of quantitative analysis results of various protein expression levels in tumor metastases of a target patient before drug intervention, and the second quantitative analysis result of proteins is a collection of quantitative analysis results of various protein expression levels in residual tumor metastases of the target patient after drug intervention.

The first quantitative analysis result of proteins and the second quantitative analysis result of proteins are acquired through high-throughput protein sequencing; and the high-throughput protein sequencing comprises protein mass spectrometry analysis.

The analysis module comprises a primary analysis submodule, a secondary analysis submodule, and a calculation and sorting submodule.

The primary analysis submodule is used for preliminary screening analysis; the preliminary screening analysis comprises comparing the first quantitative analysis result of proteins and the second quantitative analysis result of proteins, and including proteins with expression changes within a predetermined range in a candidate protein set.

During the preliminary screening analysis, the proteins with expression changes within a predetermined range are proteins whose expression levels after drug intervention are 0.95-1.05 times higher than those before drug intervention.

During the preliminary screening analysis, the proteins with expression changes within the predetermined range are first screened and then included in the candidate protein set; the proteins that are screened meet the following conditions: a number of specific peptide segments is ≥2, and is not a prediction protein; a coverage of amino acids of identified peptide segments of a current protein is ≥10%; a quantification frequency of the current protein is ≥2, and a sequencing quality comprehensive score of the current protein is ≥200; evidence in a database shows the current protein is related to tumor progression; the specific peptide segments refer to a specific peptide segment used to identify the current protein; the prediction protein refers to an attribute that defines a reliability of the current protein in Uniport or NCBI databases as a prediction protein; the identified peptide segments refer to a specific peptide segment that can be used to indicate the current protein being detected; the quantification frequency of the current protein refers to a number of repetitions of the current protein being quantitatively detected.

The secondary analysis submodule is used for secondary screening analysis; the secondary screening analysis comprises constructing, using a protein interaction network analysis tool, experimentally validated protein interaction networks based on the candidate protein set, supplementing the protein interaction networks by utilizing signal pathways involved in the candidate protein set in a signal pathway database; including most important proteins in each protein interaction network as independent heterogeneous molecules in an independent molecular set; constructing, using a protein interaction network prediction tool and based on the candidate protein set, a protein interaction prediction network according to a protein interaction law; and including proteins in the candidate protein set that do not participate in any protein interaction prediction network as independent heterogeneous molecules in the independent molecular set.

The protein interaction network analysis tool comprises a STRING network tool; the signal pathway database comprises KEGG, SMPDB, WikiPathways, Cell Signaling Technology, BioCarta Pathway, Pathway Commons, and PID; the protein interaction network prediction tool comprises a Genemania network tool, Unihi network tool, and Hitpredict network tool. A Cytoscape tool is employed to construct and supplement the protein interaction networks, and to construct the protein interaction prediction network.

During the secondary screening analysis, the most important proteins in each protein interaction network are identified through characteristic analysis; the characteristic analysis comprises analyzing the importance, degree, and radiancy of each protein in the protein interaction network; and proteins with the highest importance, degree, and radiancy are the most important proteins in the protein interaction network.

The calculation and sorting submodule is used for calculating and sorting; the calculating and sorting comprises calculating a hazard ratio (HR) value of each heterogeneous molecule in the independent molecular set, sorting the heterogeneous molecule based on the HR value, to form a sorting list of each heterogeneous molecule. HR is hazard ratio in short.

During the calculating and sorting, the HR value of each heterogeneous molecule is calculated as follows: obtaining sequencing data of tumors from a public database, obtaining a standardized counting matrix of genes corresponding to the heterogeneous molecules from the sequencing data, and performing batch single factor COX regression on the genes to obtain the HR value. The public database comprises TCGA, ICGC, and GEO.

During the calculating and sorting, a sorting rule is: the heterogeneous molecules with HR values greater than or equal to 1 are directly sorted in reverse order according to their HR values, and the heterogeneous molecules with HR values less than 1 are sorted in reverse order according to their 1/HR values.

The output module is used to output a sorted list of heterogeneous molecules.

The above modules are all runnable on computer-readable media.

In another aspect, the disclosure also provides a sequential intervention system for executing a sequential intervention order of heterogeneous molecules driving tumor metastasis. The sequential intervention system comprises the abovementioned prediction system for identifying key heterogeneous molecules driving tumor metastasis, and an execution module. The execution module is used to determine the sequential intervention order based on the sorting list of heterogeneous molecules output by the prediction system.

To validate the effectiveness of each of the above systems, the following validation methods are used:

Validation method of sequential interventions against predicted heterogeneous molecules, that is, the inhibition of tumor metastasis and prolonged survival time through interventions on heterogeneous molecules, the method is performed as follows (refers to examples):

1) based on the principle of mutual non-regulation of tumor heterogeneous molecules, selecting two molecules such as cancer suppressor gene JWA and oncogene MDM2 for the first round of joint intervention;
2) extracting residual tumor metastasis tissue after joint intervention on JWA and MDM2 for high-throughput protein sequencing;
3) based on the results of high-throughput protein sequencing, using the above prediction system, screening and sorting the heterogeneous molecules driving tumor metastasis according to HR value, as candidate targets for sequential intervention;
4) developing and implementing a sequential intervention program to inhibit tumor metastasis based on the candidate targets;
5) extracting tumor metastasis residual foci resulting from the sequential intervention program in 4), performing high-throughput protein sequencing, utilizing the above prediction system again to screen for heterogeneous molecules driving tumor metastasis, and developing and implementing a next round of sequential intervention program to inhibit tumor metastasis; and
6) repeating operations in 5) for several rounds of sequential interventions until the tumor metastasis is completely and effectively inhibited.

The disclosure is described in further detail below with reference to the accompanying drawings and in connection with examples. However, the invention is not limited to the examples given below. Unless otherwise stated, the experimental methods used are conventional experimental methods.

In the examples of the disclosure, the focus is on the systematic algorithms on how to identify heterogeneous molecules that drive tumor metastasis, and the method is applied to different species and different tumor types. The method is preferentially applicable to humans, but also to other mammals; the tumor types include, but are not limited to, gastric cancer and melanoma.

In the examples of the disclosure, the sequencing method for identifying the heterogeneous molecules driving the tumor metastasis is high-throughput protein sequencing, and the promotion and application of the achievements of the disclosure include but are not limited to being based on the high-throughput protein sequencing.

In the examples of the disclosure, the sequential intervention for gastric cancer/melanoma comprises 5 independent heterogeneous molecular targets, respectively, while the promotion and application of the achievements of the disclosure include, but are not limited to, the 5 molecule targets listed in the disclosure.

Example 1

The example provides a method of identifying heterogeneous molecules driving metastasis of gastric cancer and implementing sequential intervention on the heterogeneous molecules.

The main purpose of the example is to apply the technical solution of the disclosure to identify heterogeneous molecules driving metastasis of gastric cancer after the joint intervention of JWA and MDM2, and further to implement a sequential intervention strategy to verify the effectiveness of the technical solution of the disclosure.

Figure 1B:
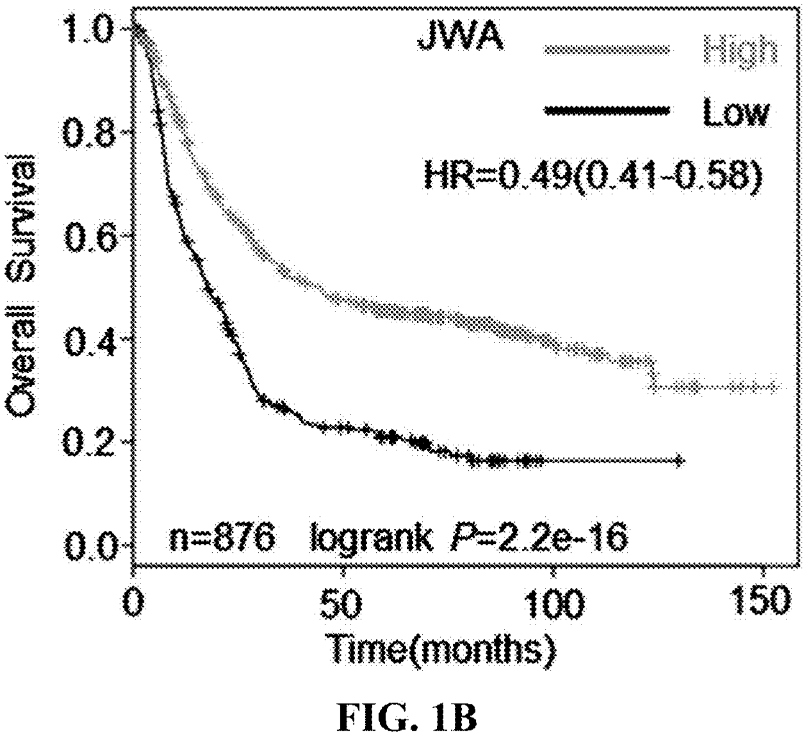

1.1 Relationship between cancer suppressor gene JWA and the prognostic and metastatic characteristics of gastric cancer The relationship between JWA and prognosis of the gastric cancer population was analyzed using TCGA database. FIGS. 1A-1B show a comparison of JWA mRNA levels in paired and unpaired cancerous and paracancerous tissues, which indicates that the JWA mRNA levels in cancerous tissues are lower than that in the paracancerous tissues (FIG. 1A); patients with low JWA expression have a poor prognosis FIG. 1B).

Figure 2A:
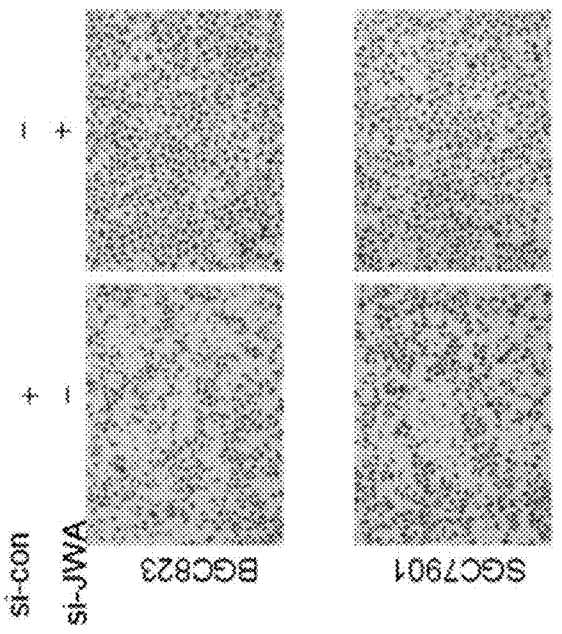
Figure 2B:
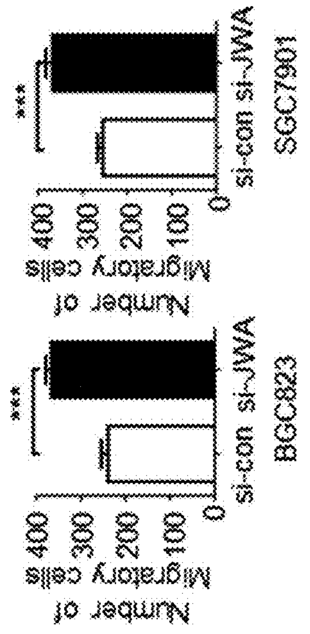
Figure 2C:
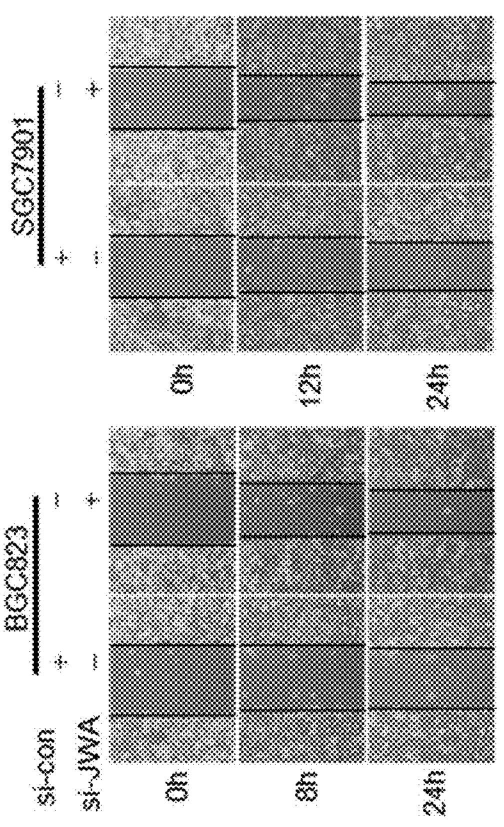
Figure 2D:
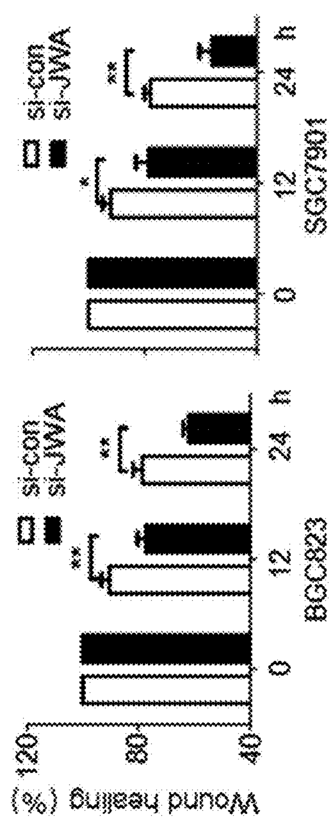

Gastric cancer cells BGC823 and SGC7901 were transfected with si-JWA to interfere with JWA mRNA and its protein expression level. The results of a transwell assay showed that low expression of JWA in the gastric cancer cells led to the increase of the number of tumor cells passing through the cells in the same period of time (FIG. 2A and FIG. 2B); the results of a scratch assay showed that low expression of JWA in the gastric cancer cells accelerated the speed of healing (FIG. 2C and FIG. 2D). Thus, as shown in FIGS. 2A-2D, reducing the expression level of JWA could enhance the migration ability of gastric cancer cells.

Figure 3A:
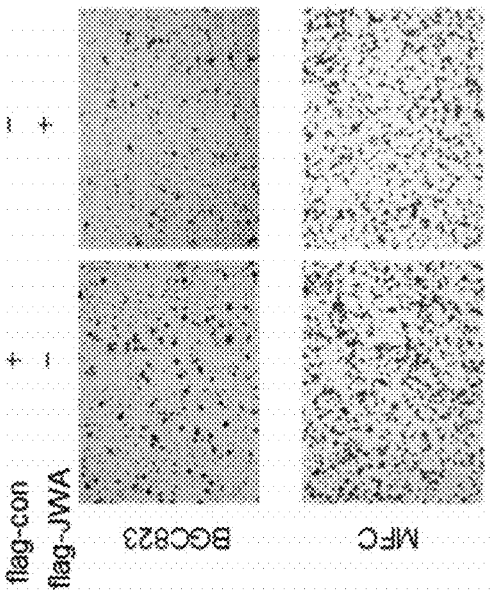
Figure 3B:
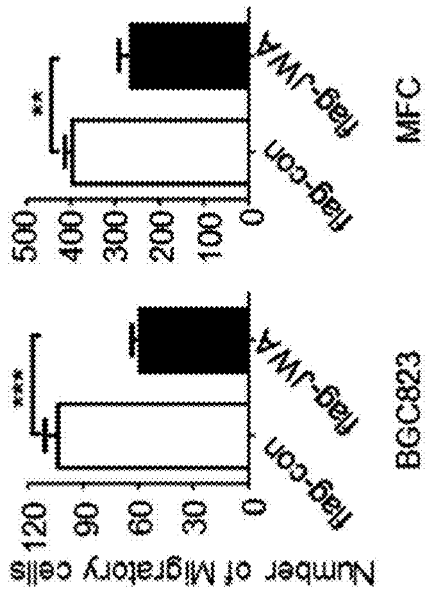
Figure 3C:
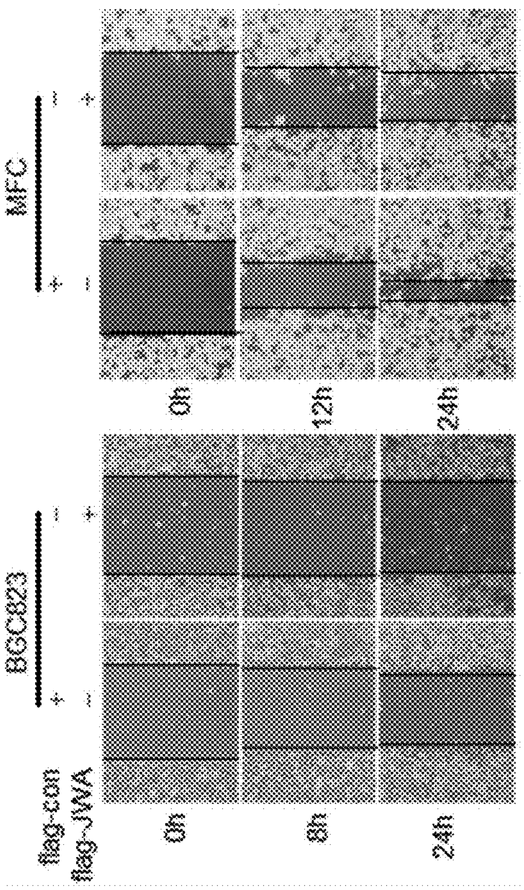
Figure 3D:
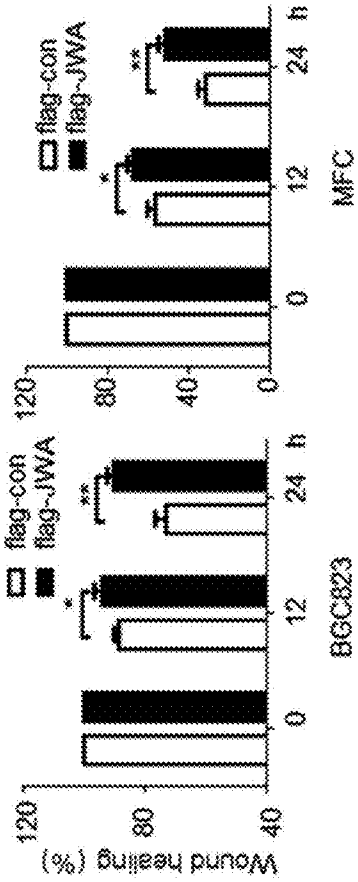

Similarly, Flag-JWA was transfected into gastric cancer cells BGC823 and MFC to increase JWA protein expression levels. The results of a transwell assay showed that JWA were highly expressed in the gastric cancer cells, and the number of tumor cells passing through the small chamber decreased at the same time (FIG. 3A and FIG. 3B); the results of a scratch assay showed that the healing speed of gastric cancer cells significantly slowed down after high expression of JWA (FIG. 3C and FIG. 3D). As shown in FIGS. 3A-3D, increasing the expression level of JWA can weaken the migration ability of gastric cancer cells.

Figure 4B:
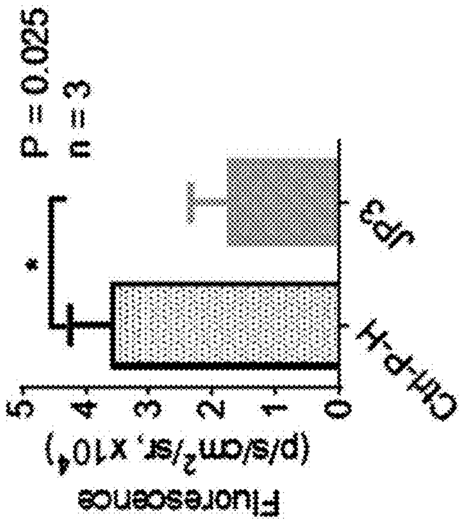
Figure 4A:
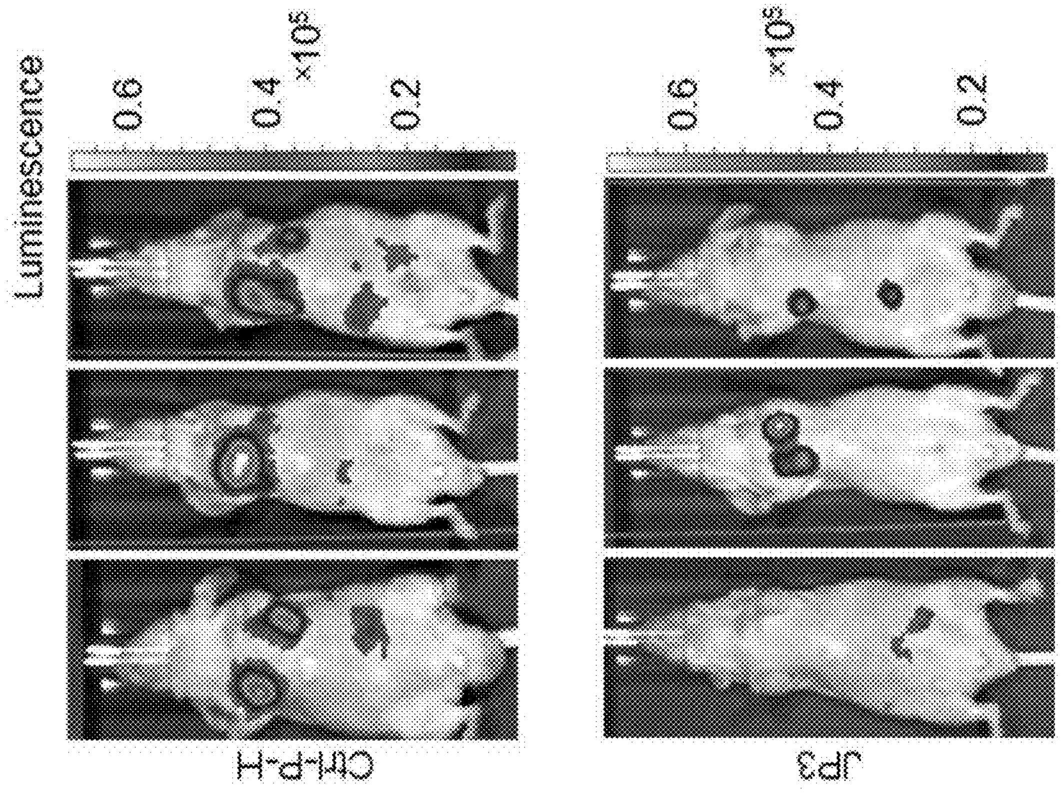

BGC823 cells were selected and injected into the tail vein of nude mice to construct a passive metastasis model. On the 2nd day after cell inoculation, mice were grouped and injected intraperitoneally with peptides, JP3 or Ctrl-P-H. As shown in FIGS. 4A-4B, compared with the control peptide, Ctrl-P-H, the lung metastasis foci of mice in the JP3 group were significantly smaller. Note: JP3 and Ctrl-P-H peptides are described in Chen J et al. J Exp Clin Cancer Res. 2020; 39: 118.

The above results indicate that the use of a simulated peptide JP3 based on the tumor suppressor gene JWA can effectively inhibit the in vivo and in vitro metastasis of gastric cancer.

Figure 5B:
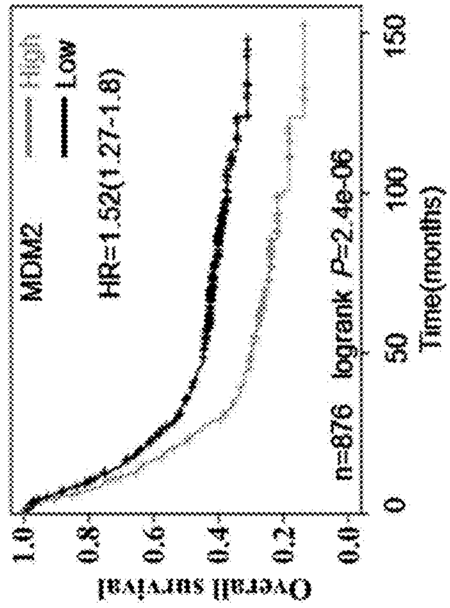
FIGS. 5A-5B, 6A-6C, 7A-7B, and 8A-8E show a relationship between the oncogene MDM2 and the prognosis and metastasis characteristics of gastric cancer in operations 1.2 of Example 1 of the disclosure.
Figure 5A:
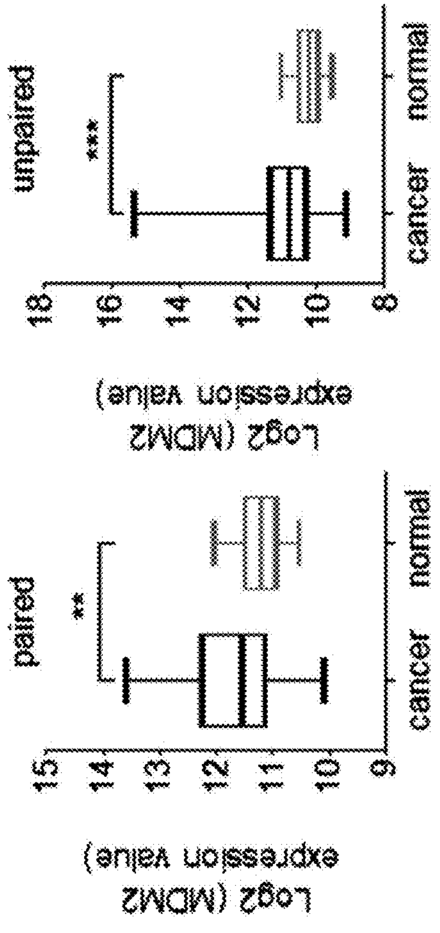

1.2 Relationship between oncogene MDM2 and the prognosis and metastasis characteristics of gastric cancer The relationship between MDM2 and prognosis of the gastric cancer population was analyzed using TCGA database. FIGS. 5A-5B show a comparison of MDM2 mRNA levels in paired and unpaired cancerous and paracancerous tissues, which indicates that the MDM2 mRNA levels in cancerous tissues are higher than that in the paracancerous tissues (FIG. 5A); patients with low MDM2 expression have a better prognosis than those with high MDM2 expression (FIG. 5B).

Figure 6A:
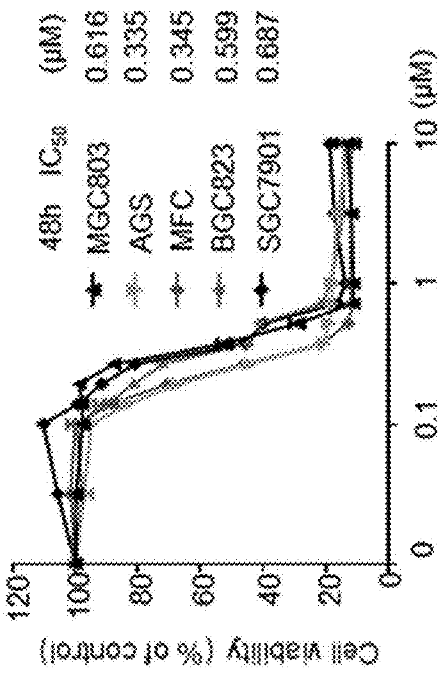
Figure 6B:
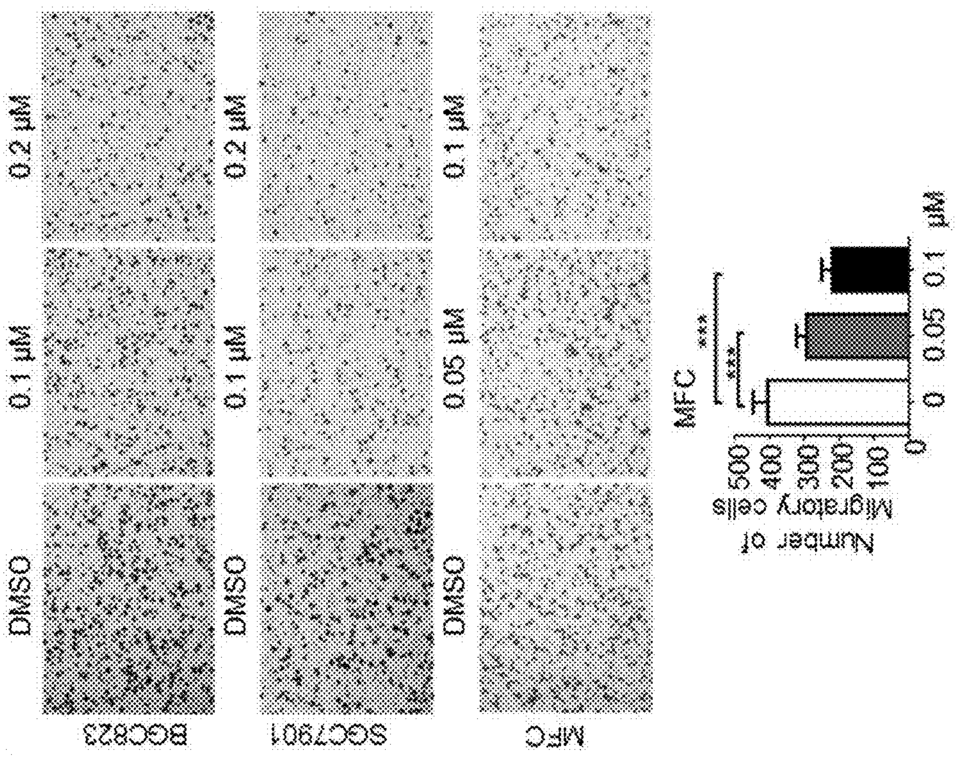
Figure 6C:
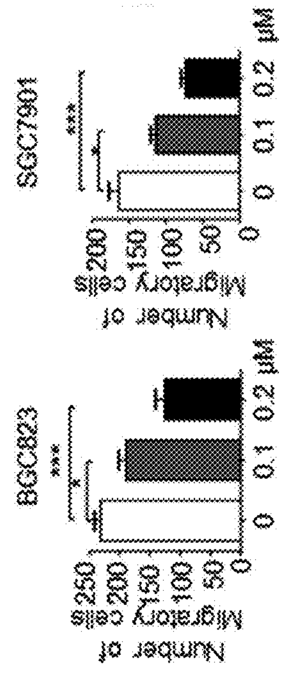

As shown in FIGS. 6A-6C, the CCK-8 method was used to detect the half inhibitory concentration ($IC_{50}$) of MDM2 inhibitor SP141 (existing product) on gastric cancer cells MGC803, AGS, MFC, SGC7901, and BGC823, with $IC_{50}$ values of 0.616 μM, 0.335 μM, 0.345 μM, 0.687 μM, and 0.599 μM, respectively (FIG. 6A). The results of a scratch assay showed that when gastric cancer cells BGC823, SGC7901, and MFC were treated with different doses of SP141 for 24 hours, the number of perforated cells gradually decreased with increasing dose of SP141 in a dose-response relationship (FIG. 6B and FIG. 6C).

Figure 7A:
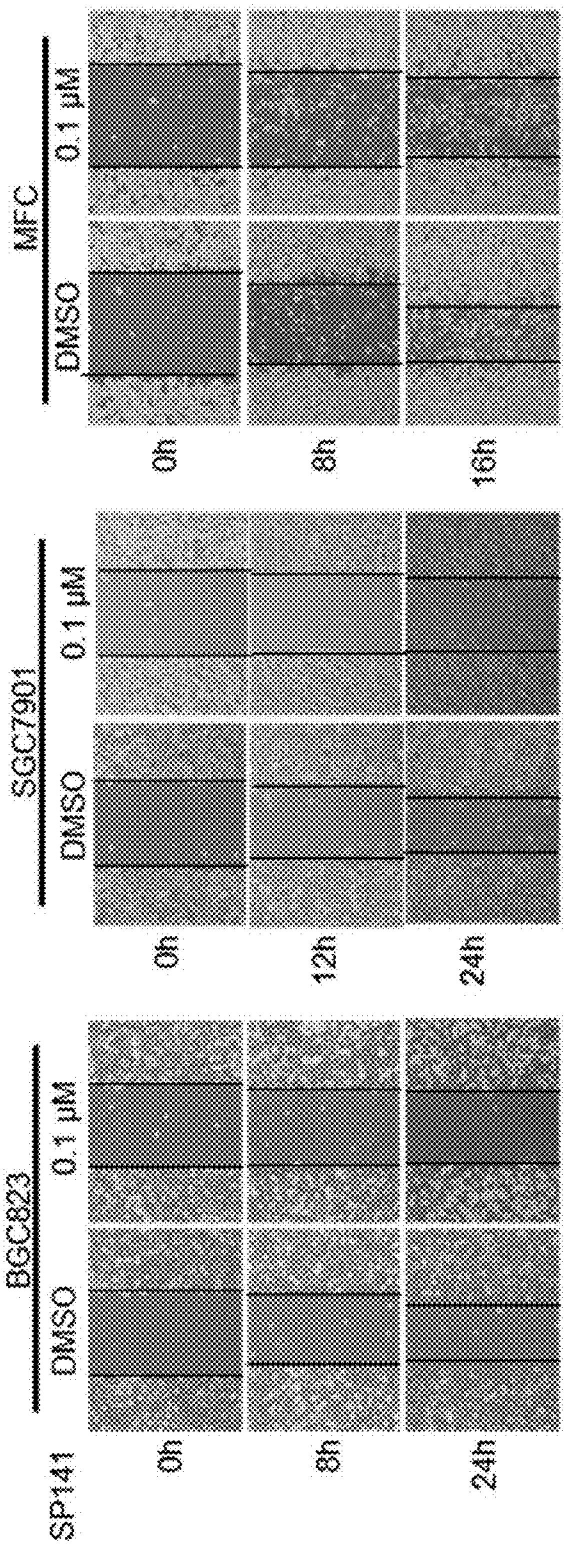
Figure 7B:
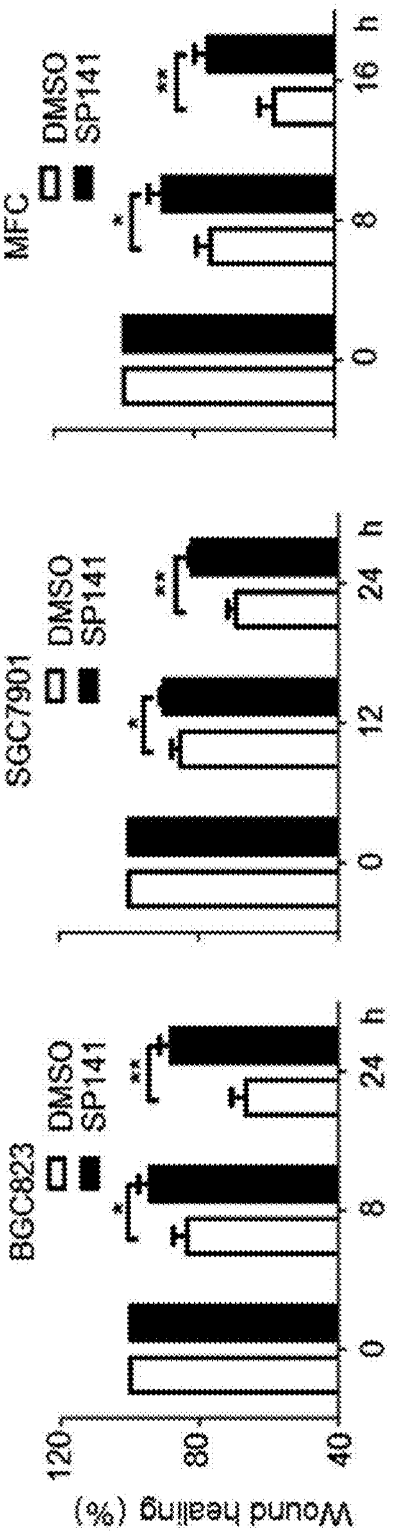
Figure 8A:
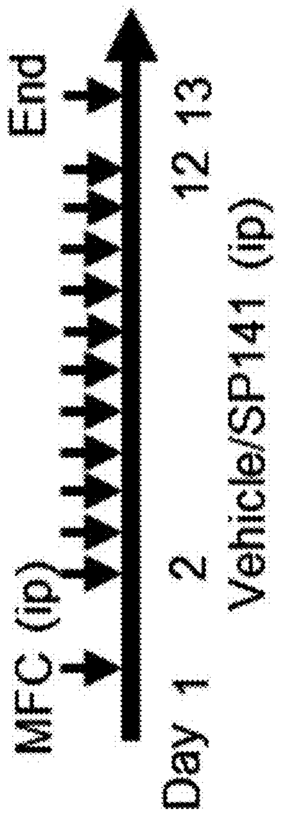
Figure 8B:
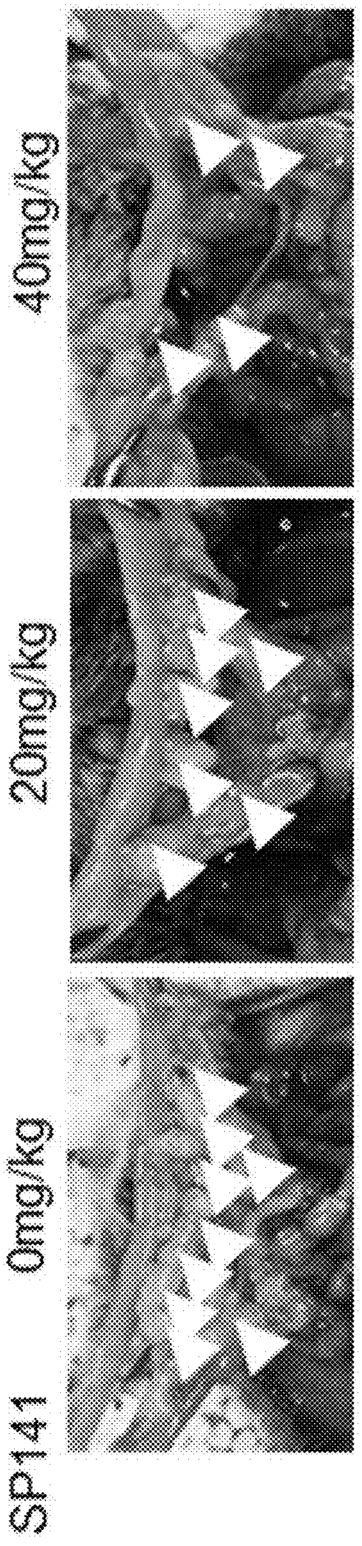
Figure 8D:
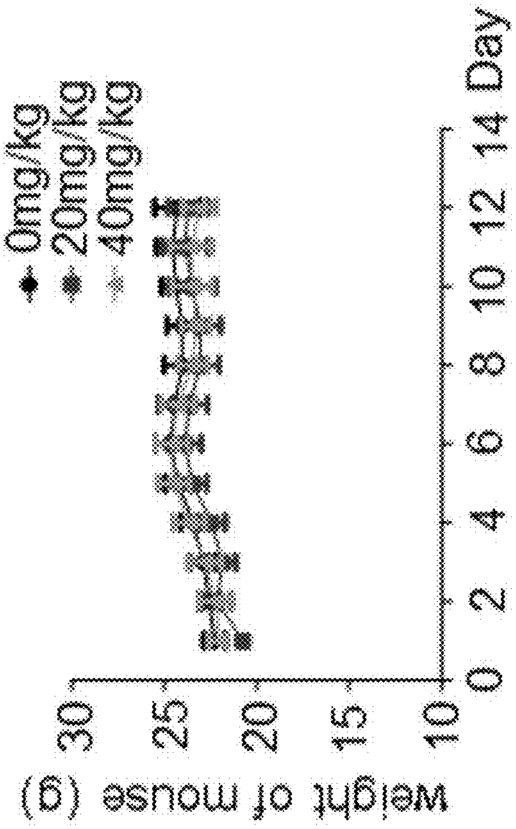
Figure 8C:
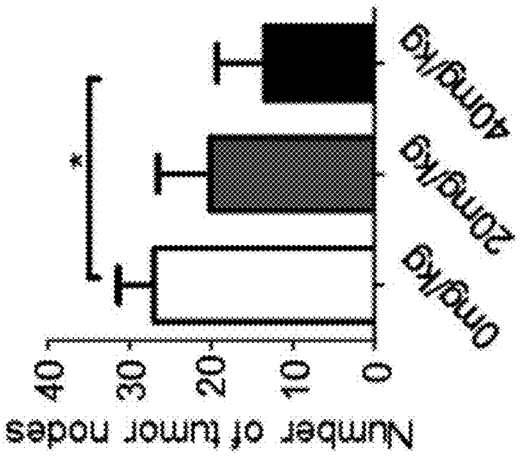
Figure 8E:
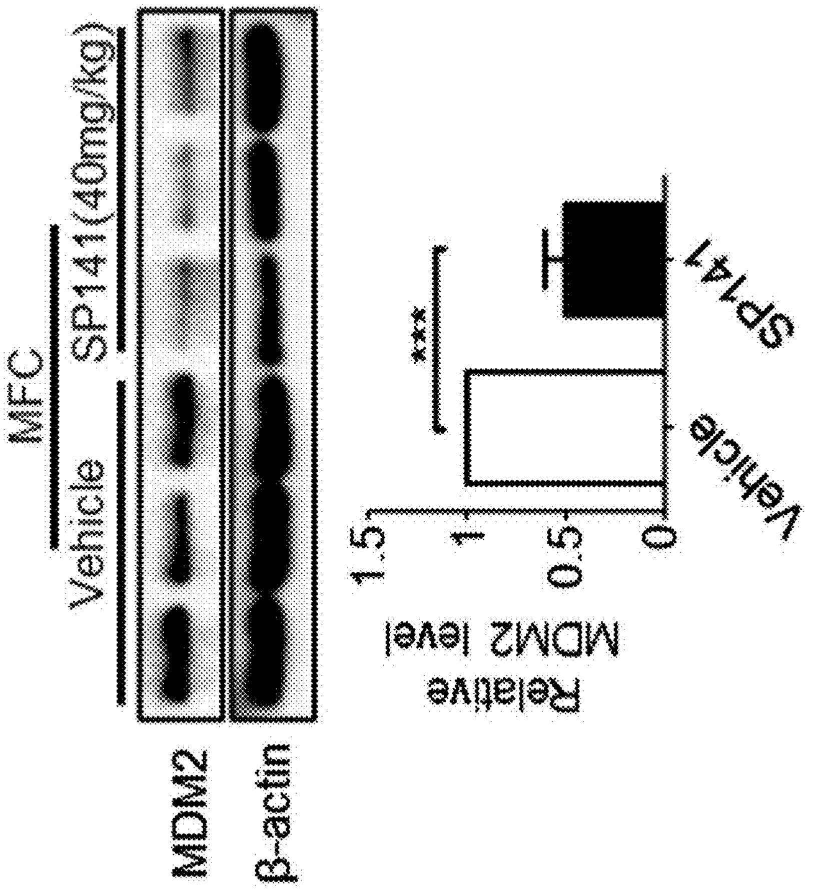

Similar results were obtained from a cell scratch assay. After the gastric cancer cells BGC823, SGC7901, and MFC were treated with SP141, the migration rate of the cells significantly slowed down, as shown in FIGS. 7A-7B.

The mouse-derived gastric cancer cell line MFC were selected to construct an abdominal implant metastasis model. On the second day of cell inoculation, different doses of SP141 were administered intraperitoneally for intervention. The modeling was completed and the number of abdominal metastatic nodules was recorded. As shown in FIGS. 8A-8E, SP141 could inhibit the number of gastric cancer abdominal implantation metastases, presenting a dose-response relationship. Compared with the control group, the data of the 40 mg/kg group was statistically significant. Whole protein immunoblotting analysis was performed on the residual tumor tissues from the control group and the 40 mg/kg group, and the results showed a significant decrease in MDM2 protein levels in the SP141 intervention group.

The above results indicate that reducing the expression of the oncogene MDM2 can effectively inhibit the in vivo and in vitro metastasis of gastric cancer.

Figure 9A:
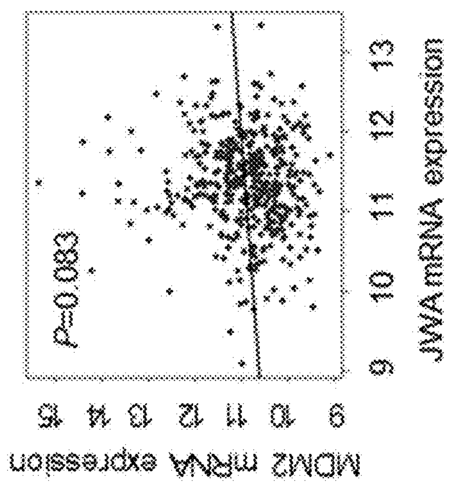
FIGS. 9A-9C, 10A-10B, and 11A-11D show JWA and MDM2 are functionally independent heterogeneous molecules that can synergistically inhibit in vivo and in vitro metastasis of gastric cancer in operations 1.3 of Example 1 of the disclosure.
Figure 9B:
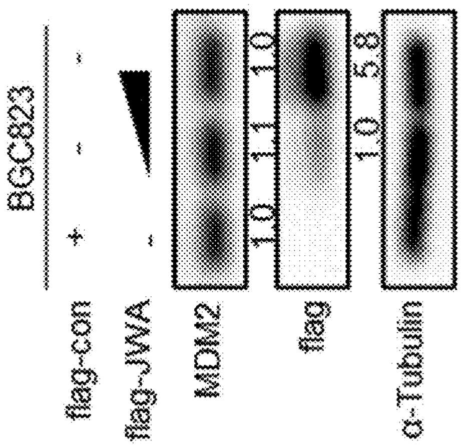
Figure 9C:
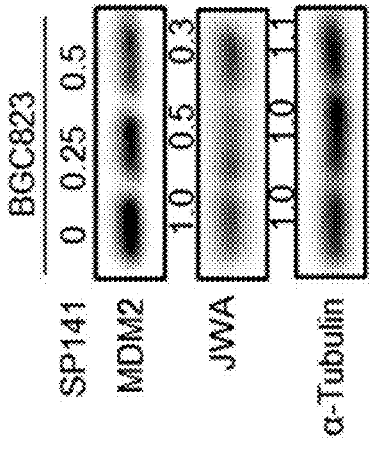

1.3 JWA and MDM2 are functionally independent heterogeneous molecules that can synergistically inhibit gastric cancer metastasis The correlation between JWA and MDM2 mRNA in 413 gastric cancer tissue samples was analyzed using the TCGA database, and the results showed no correlation between the two genes (FIG. 9A). With a cell model, the mutual regulation between JWA and MDM2 proteins was examined. Different doses of Flag-JWA plasmids were transfected into BGC823 cells, and the gradient increase of JWA protein levels did not result in significant changes in MDM2 protein (FIG. 9B). Thereafter, 0, 0.25, 0.5 μM SP141 were used to inhibit the expression level of MDM2 in gastric cancer cells BGC823 for 24 hours. The results showed that the protein expression level of MDM2 decreased with increasing SP141 dose, while there was no significant change in the protein expression level of JWA (FIG. 9C). Thus, it can be seen that as shown in FIGS. 9A-9C, in gastric cancer, JWA and MDM2 have no mutually regulatory relationship at the protein and mRNA levels, and their respective biological functions on gastric cancer cells are independent.

Figure 10B:
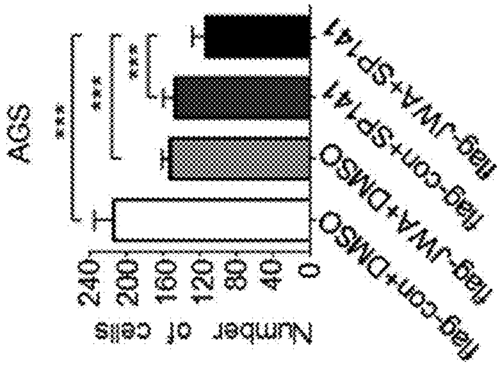
Figure 10A:
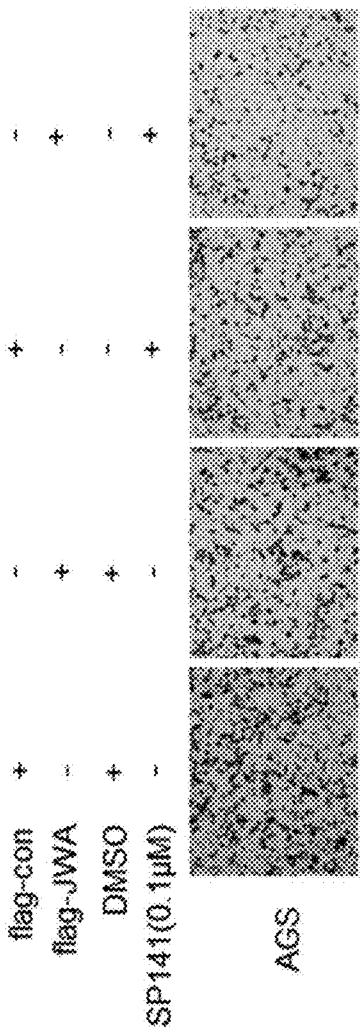

The results of the transwell assay showed that transfection of Flag-JWA plasmid into AGS cells followed by SP141 treatment resulted in a decrease in the number of cell perforations in both the single and combined treatment groups compared to the control group, while the combined treatment group had the least number of cells, and the difference was statistically significant. Thus, as shown in FIGS. 10A-10B, the combined intervention of JWA and MDM2 has a synergistic inhibitory effect on gastric cancer cell migration.

Figure 11A:
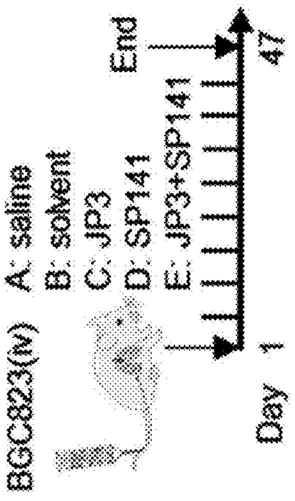
Figure 11B:
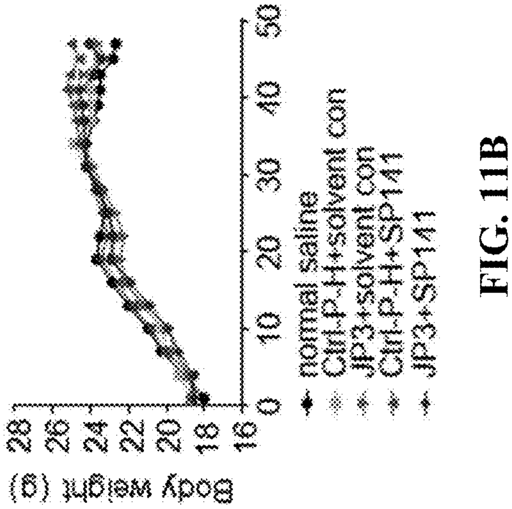
Figure 11C:
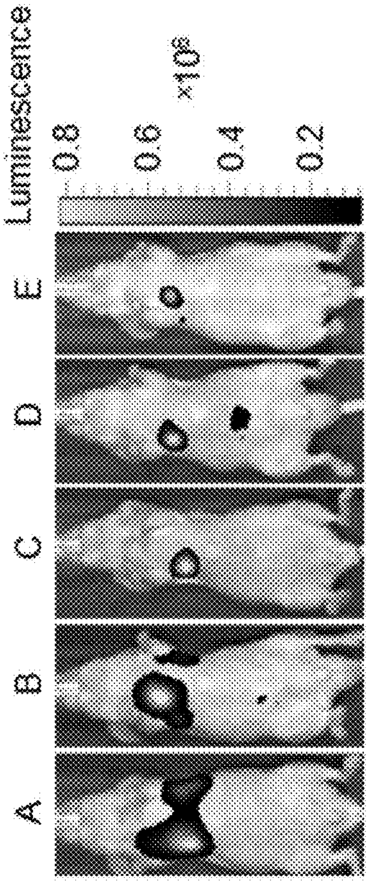
Figure 11D:
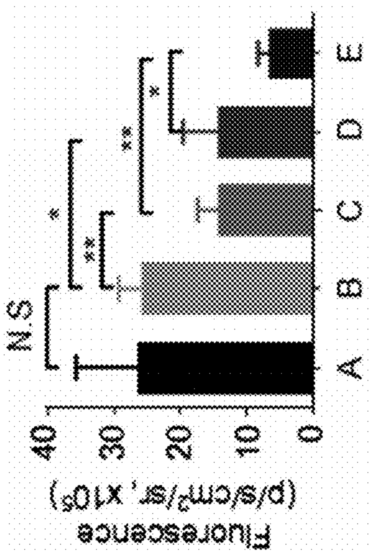

In an in vivo model, fluorescent labeled gastric cancer cells BGC823-luc were injected into the tail vein of nude mice to construct a passive metastasis model of gastric cancer. Drug intervention began on the second day after cell inoculation (FIG. 11A). The observation results showed that in the early stage of the model, the weight of the mice steadily increased, and after 33 days, the weight of the control group mice began to decrease. The weight of the mice of the drug intervention group was relatively stable and in good condition (FIG. 11B). The results of in vivo fluorescence imaging showed that the fluorescence intensity of lung metastases in the saline group and solvent control group was relatively similar. The fluorescence intensity of the individual SP141 and JP3 intervention groups was weaker than that of the control group, and the difference was statistically significant. The joint intervention group had the weakest lung fluorescence intensity, and there was a statistically significant difference in fluorescence intensity compared to the individual intervention group (FIG. 11C and FIG. 11D). Thus, as shown in FIGS. 11A-11D, the joint intervention of JWA and MDM2 has a synergistic inhibitory effect on gastric cancer metastasis in vivo.

The above results indicate that the joint intervention on the heterogeneous molecules JWA and MDM2 driving gastric cancer metastasis have a synergistic inhibitory effect on gastric cancer metastasis.

1.4 Identifying other heterogeneous molecules driving gastric cancer metastasis after joint intervention on JWA and MDM2

Figure 12:
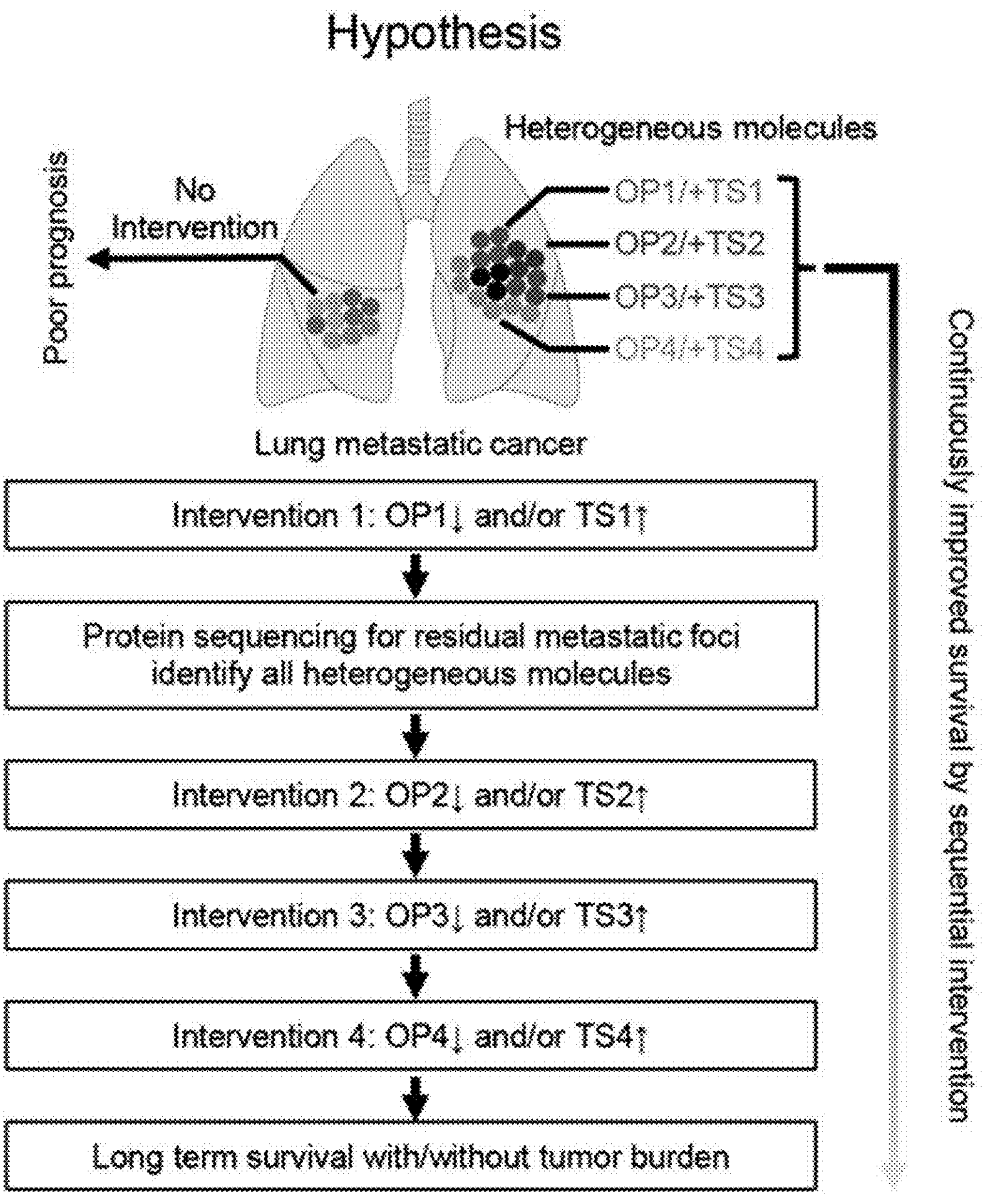

This section proposes a theory for identifying heterogeneous molecules driving tumor metastasis and implements sequential interventions for validation. Tumor heterogeneous molecules are partially independent in function and can drive various malignant phenotypes including metastasis. Even if the best intervention measures are taken for a gene (whether it is an oncogene or a tumor suppressor gene), the expression and function of other heterogeneous molecules are not affected. Therefore, under appropriate conditions, these heterogeneous molecules will play a dominant role in tumor cell fate through adaptation, driving tumor recurrence and metastasis. In the disclosure, the traditional concept of searching for and discovering differentially expressed molecules for targeted interventions has been replaced with a concept to search for heterogeneous molecules that remain unaffected in expression after targeted drug intervention but may drive tumor metastasis. Assuming that sequential interventions targeting these molecules can effectively prolong the survival of cancer patients, as shown in FIG. 12.

As described in 1.3, the joint intervention on JWA and MDM2 significantly enhanced the inhibitory effect on gastric cancer metastasis. However, even with continued joint intervention, after a period of time, lung metastases and drug resistance in mice still develop due to adaptation to the microenvironment, indicating the presence of heterogeneous molecules that are not regulated by JWA and MDM2 after JP3 and SP141 intervention. To predict and identify unknown heterogeneous molecules driving the subsequent progression of gastric cancer, protein mass spectrometry analysis was performed on the metastatic lesions that still existed after the joint intervention of JP3 and SP141. Protein molecules with stable expression levels compared to the control group were screened from a total of more than 7000 protein quantitative analyses (specific indicators were: the expression level of target molecules in residual metastatic lesions after JP3 combined with SP141 intervention/the range of changes in residual metastatic lesions in the control group was 0.95-1.05).

Figure 13:
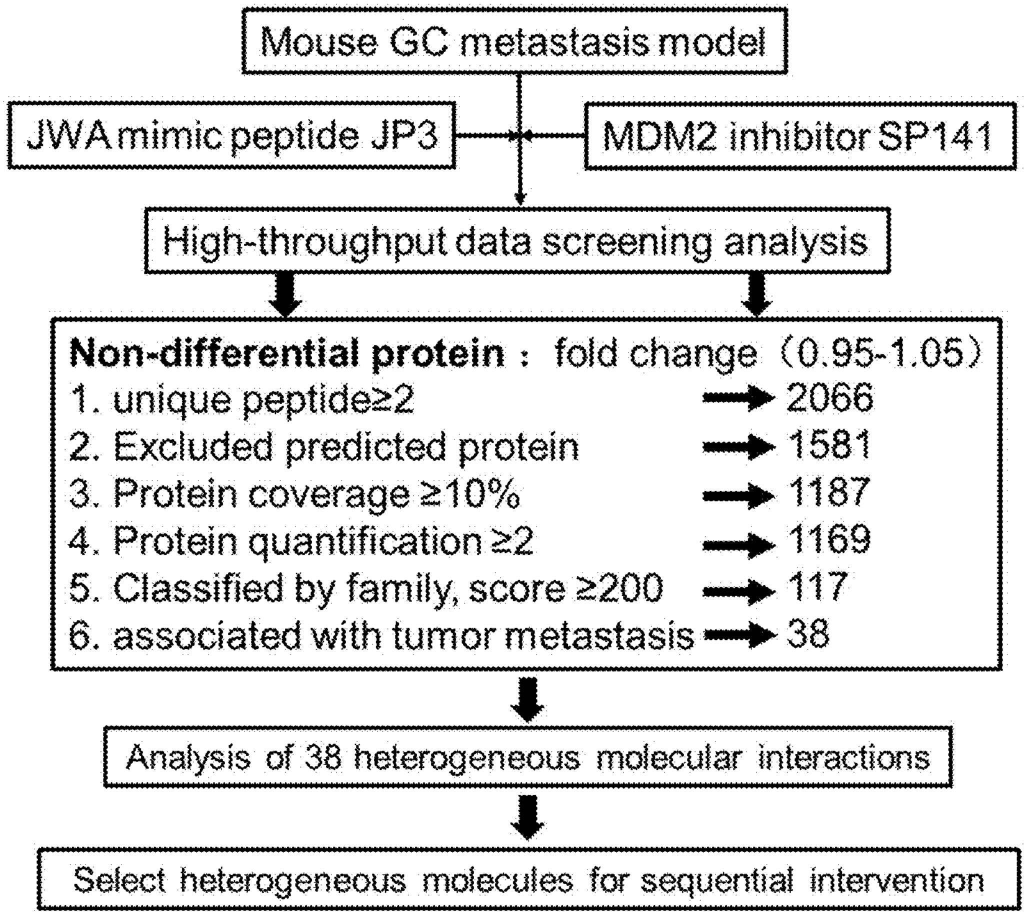

Furthermore, based on sequencing related quality control data and the correlation between molecules and tumors, candidate heterogeneous molecules meeting the following conditions were preliminarily screened: (1) protein molecules with a specific peptide number ≥2; (2) remove predicted protein molecules; (3) remove molecules with identified peptide segments covering less than 10% of the entire protein; (4) remove molecules with protein (129C/129N peptide) quantification less than twice; (5) remove molecules with a comprehensive score of less than 200 in protein sequencing; (6) retrieve keywords, including proteins and their corresponding gene names, and cancer in relevant databases (such as PubMed, Web of Science, CNKI, Wanfang Database, and VIP) to determine their correlation with tumor progression, and remove irrelevant molecules. Through the screening, 2066 protein molecules with a specific peptide segment (referring to the specific peptide segment used to identify the current protein) of ≥2 were identified; 1581 remained after predicted proteins (based on the reliability, the attribute of the current protein is defined as predicted proteins in Uniport or NCBI databases) were excluded; 1187 peptide segment molecules with an amino acid coverage rate of over 10% in the entire protein have been identified (referring to specific peptide segments that can be used to indicate the current protein being detected); 1169 molecules with 129C/129N (mass spectrometry report ion ratio) peptide quantification times (referring to the number of repetitions of the current protein being quantitatively detected) exceeding two times; 117 molecules with a sequencing quality comprehensive score exceeding 200; database analysis confirmed a total of 38 protein molecules associated with tumor progression, as shown in FIG. 13. FIGS. 14 and 42A-42C provide relevant information on candidate heterogeneous molecules.

Figure 15:
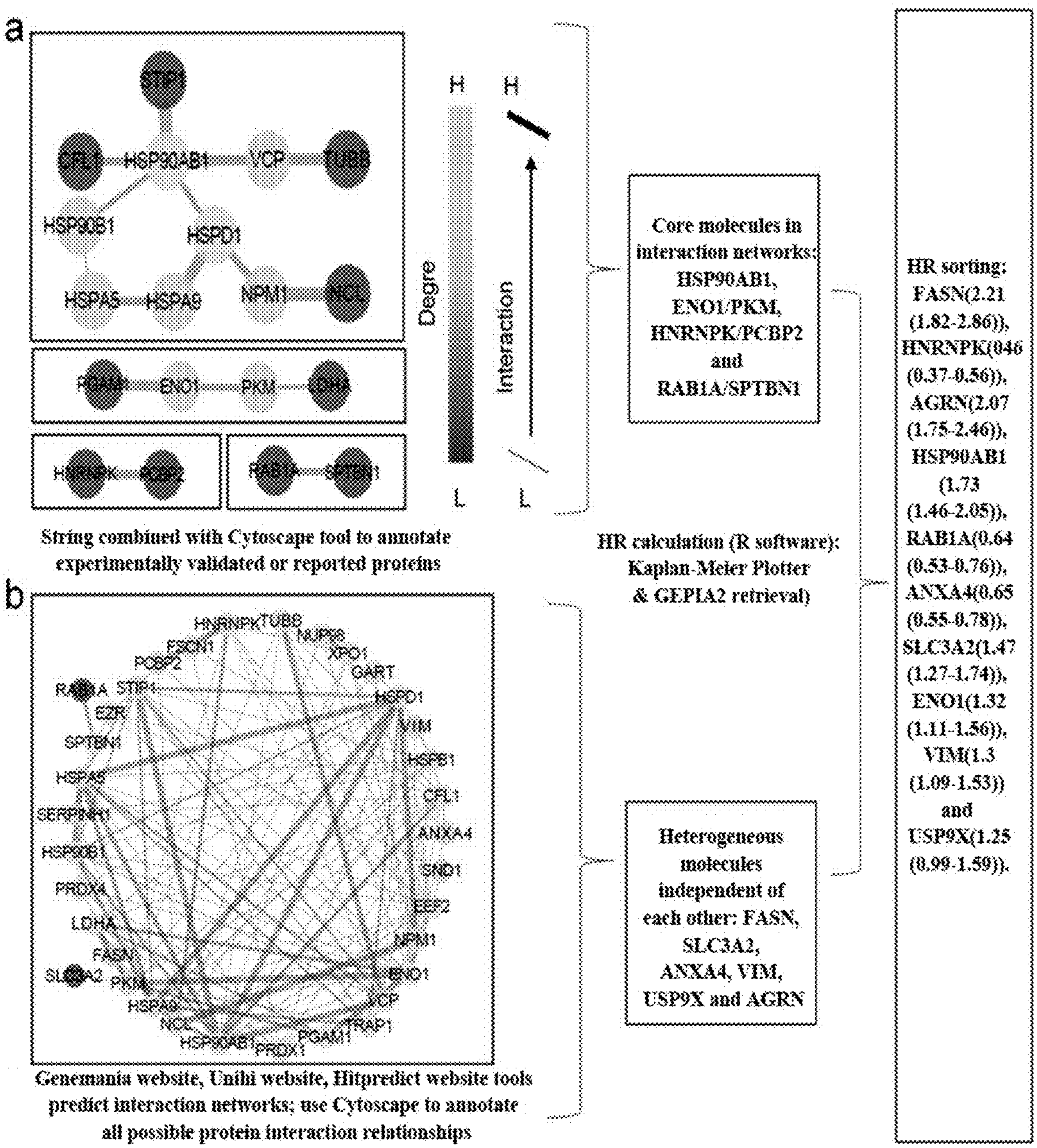
Figure 17:
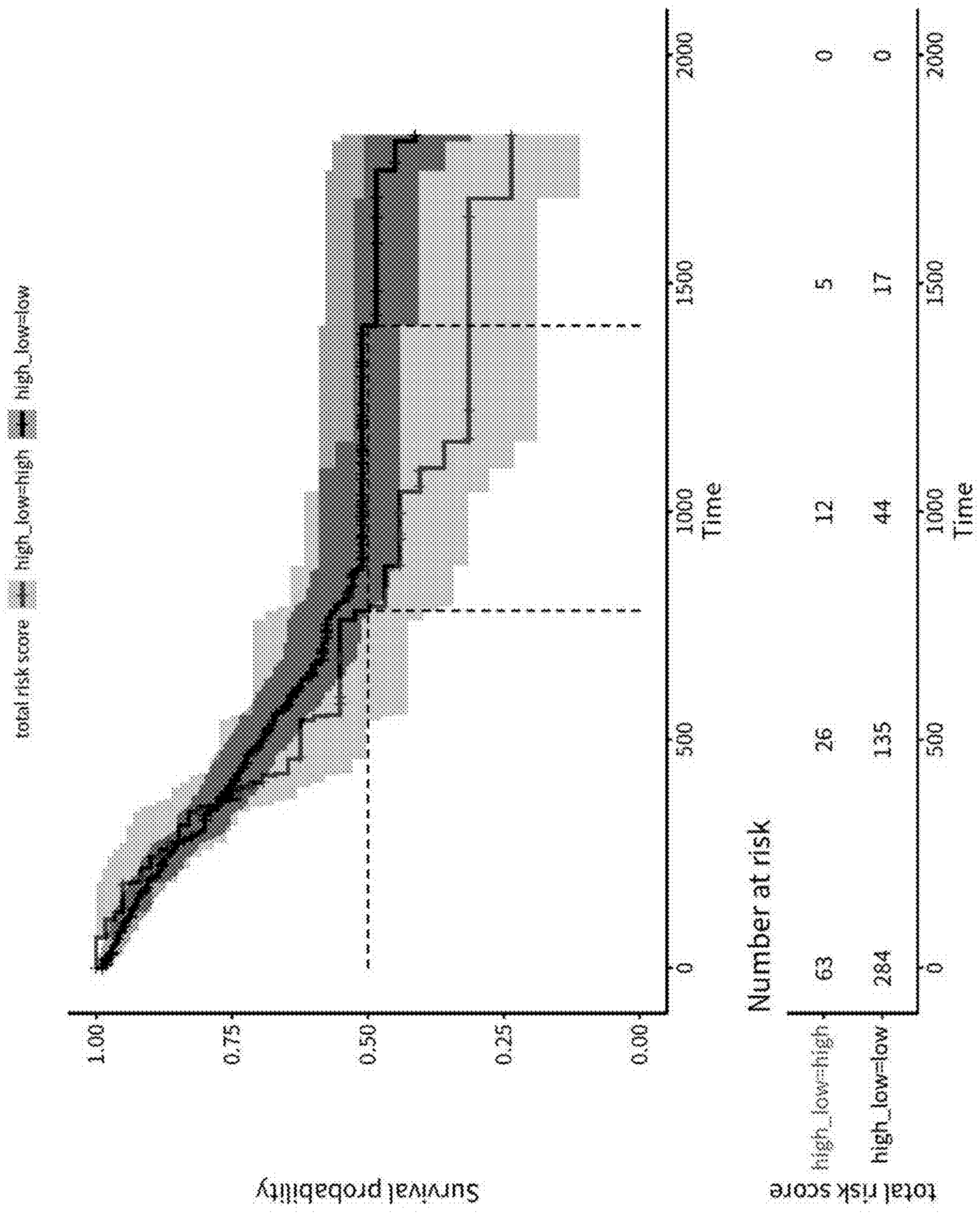

The preliminarily screened heterogeneous molecules may comprise completely independent individual heterogeneous molecules and some heterogeneous molecules with mutual regulatory effects. To screen for independent heterogeneous molecules, a currently known protein interaction network was constructed using STRING website, with the basis for determining protein interactions being experimental validation and database knowledge. Afterwards, using the 38 heterogeneous molecules as inputs, based on KEGG, SMPDB, WikiPathways, Cell Signaling Technology, BioCarta Pathway, Pathway Commons, and PID databases, the signal pathway information involved in the heterogeneous molecules was analyzed to see if there were protein molecules present in the same signal pathway. Then, new protein points and protein interaction relationships were added through Cytoscape software for further modification and correction (FIG. 15). Finally, based on the molecular point relationships in the interaction network, the network's attributes (connectivity, clustering coefficient, compactness, and topology coefficient) was calculated using a script, and the importance, degree, radiance, and other characteristics of the network were analyzed using the network analyzer module in Cytoscape software (FIGS. 16-18). Thereafter, based on the independent interaction network, the heterogeneous molecules with the highest importance, degree, and radiance were selected to determine which molecules can form an independent network (containing more than 2 proteins) and the most important heterogeneous molecules in the network, namely HSP90AB1, ENO1/PKM, HNRNPK/PCBP2, and RAB1A/SPTBN1. For the heterogeneous molecules that made up the regulatory network, the cumulative HR values of each molecule in the network were calculated and assigned to the representative heterogeneous molecules in the network, as shown in FIGS. 15-18. On the other hand, using the Genemania website, Unihi website, and Hitpredict website, based on algorithmic ideas such as text mining, coexpression, structural domain and gene fusion, it was found that among the 38 molecules, there were independent heterogeneous molecules that did not form an interaction network with other molecules, namely FASN, SLC3A2, ANXA4, VIM, USP9X, and AGRN. The HR cumulative values of these molecules were also calculated. Afterwards, the intervention order was sorted by reference to the HR values of the overall survival corresponding to independent heterogeneous molecules (sorted in reverse order according to their HR values when HR values were greater than 1, and sorted in reverse order according to their 1/HR values when HR values were less than 1). The HR sequence of independent heterogeneous molecules driving gastric cancer metastasis after joint intervention on JWA and MDM2 was determined as follows: FASN (2.21 (1.82-2.86), p=1.6e-16); HNRNPK (0.46 (0.37-0.56), p=3.9e-14); AGRN (2.07 (1.75-2.46), p<1e-16); HSP90AB1 (1.73 (1.46-2.05), p=1.7e-10). RAB1A (0.64 (0.53-0.76), p=5.2e-07); ANXA4 (0.65 (0.55-0.78), p=1.4e-06). SLC3A2 (1.47 (1.27-1.74), p=1.1e-05); ENO1 (1.32 (1.11-1.56), p=0.0014); VIM (1.3 (1.09-1.53), p=0.0027) and USP9X (1.25 (0.99-1.59), p=0.061). In this way, whether heterogeneous molecules with regulatory relationships or completely independent individual heterogeneous molecules, corresponding HR values have been obtained through the analysis, calculation, and assignment. The intervention order of all heterogeneous molecules can be determined based on the size of the HR value. FIG. 15 shows the molecular screening and HR value ranking of partial gastric cancer heterogeneity.

1.5 Sequential intervention on JWA, MDM2, and FASN can effectively inhibit in vivo metastasis of gastric cancer.

Based on the results of 1.4, FASN was determined as the next intervention target.

Figure 19A:
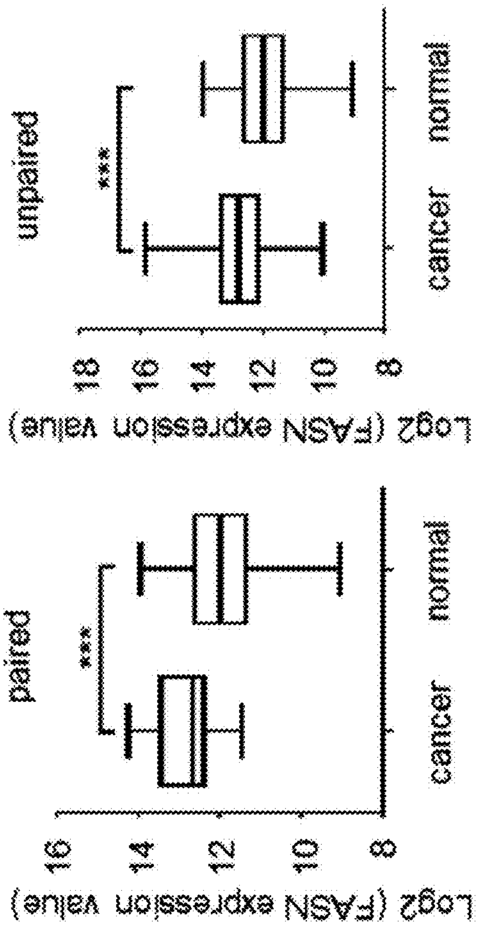
FIGS. 19A-19B, 20A-20D, and 21A-21C show results of sequential intervention on JWA, MDM2, and FASN in operations 1.5 of Example 1 of the disclosure, which can effectively inhibit in vivo metastasis of gastric cancer.
Figure 19B:
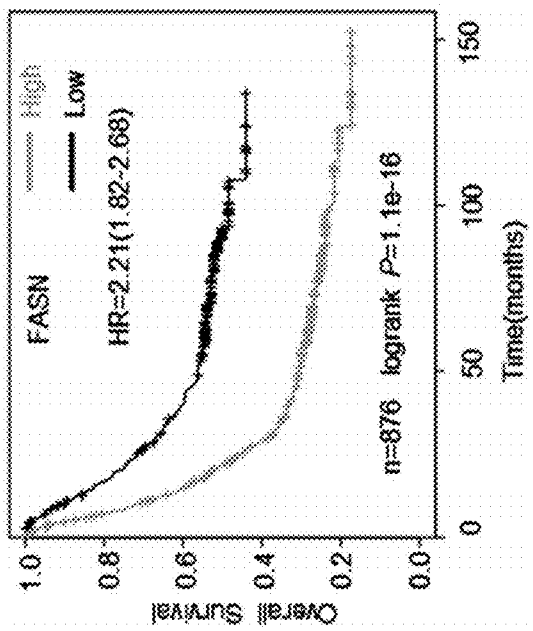

The relationship between FASN and the prognosis of gastric cancer population was analyzed using TCGA database, as shown in FIGS. 19A-19B. The mRNA levels of FASN in paired and unpaired cancerous tissues were higher than that in the paracancerous tissues, and the difference was statistically significant (FIG. 19A). Patients with low FASN expression had better prognosis than those with higher FASN expression (FIG. 19B).

Figure 20A:
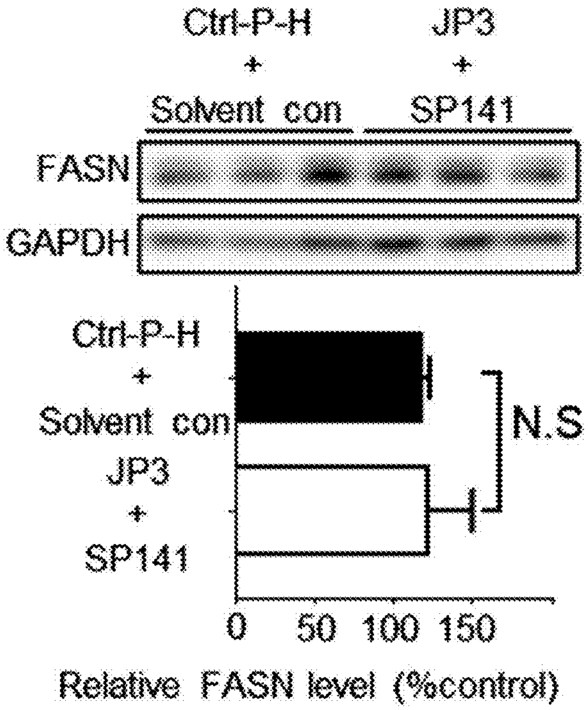
Figure 20B:
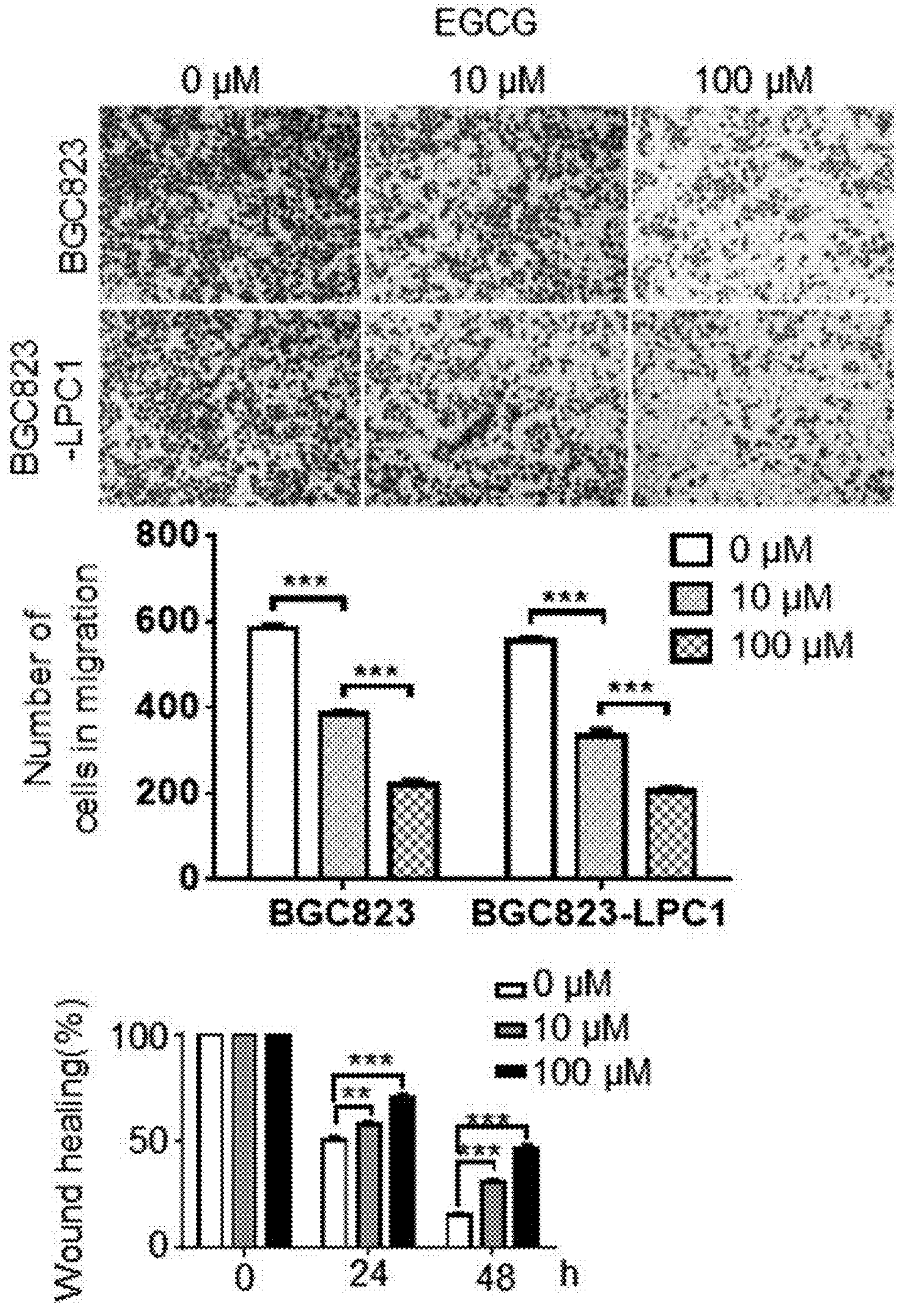
Figure 20C:
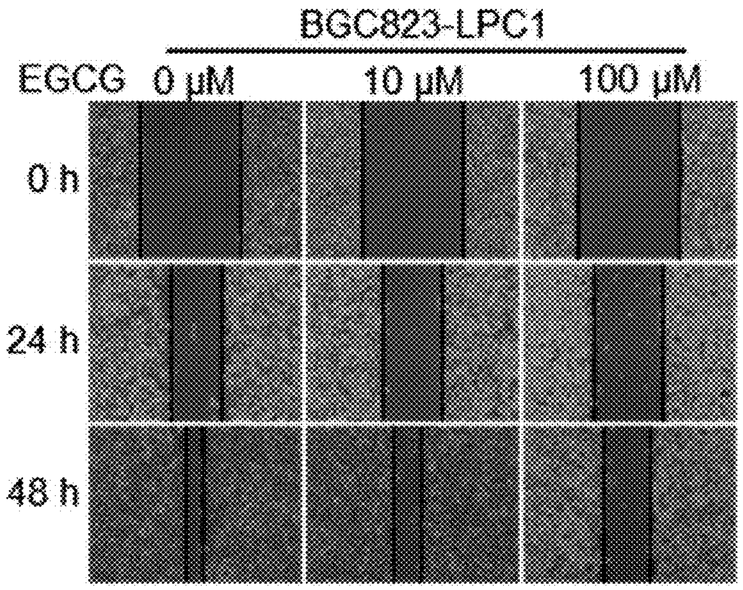
Figure 20D:
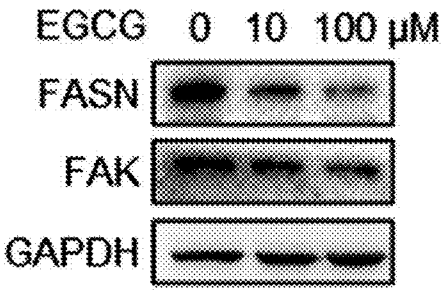

The detection of FASN protein levels in residual metastatic foci in lung tissue of mice in the solvent control group and JWA+MDM2 joint intervention group in animal models showed stable FASN expression in both groups, consistent with the protein mass spectrometry results (FIG. 20A). Further validation of the relationship between FASN and gastric cancer metastasis using transwell and scratch experiments: BGC823 cells and BGC823-LPC1 (primary cells of residual lung metastases in the animal model SP141 and JP3 combined intervention group) were treated with different concentrations of FASN inhibitor EGCG for 24 hours, followed by transwell experiments. The results showed that the number of perforation cells in the EGCG treated group was significantly reduced, and there was a dose-response relationship. The inhibition rate of perforation cells was similar in both types of cells (FIG. 20B). Similar results were obtained in the scratch experiment (FIG. 20C). The results of the immunoblotting experiment (FIG. 20D) showed that after EGCG treatment of cells, the expression level of FASN protein was reduced, and the transfer related protein FAK was also correspondingly reduced, both of which showed a dose-response relationship. As shown in FIGS. 20A-20D, intervention on FASN can inhibit the migration of gastric cancer cells.

Figure 21A:
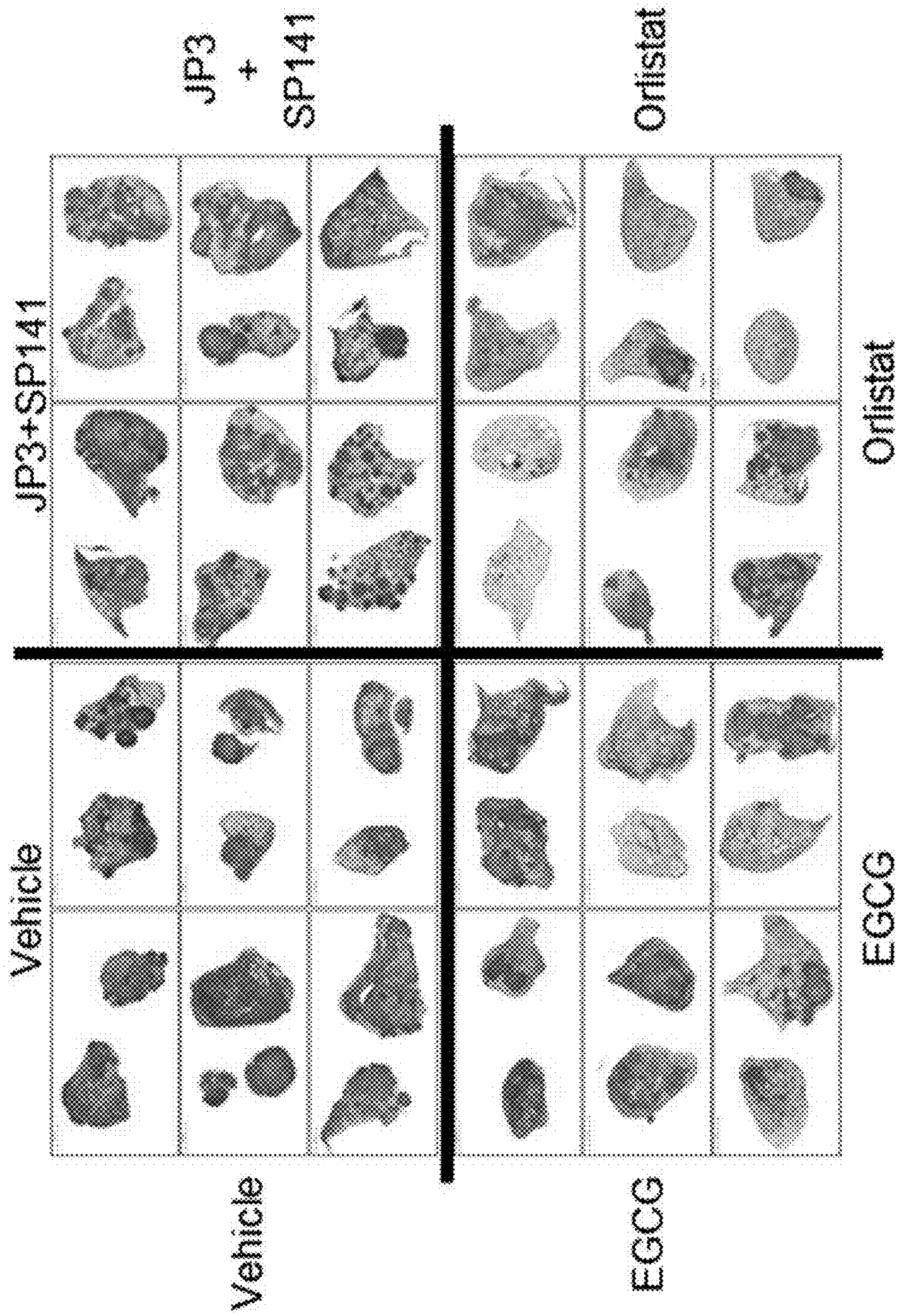
Figure 21B:
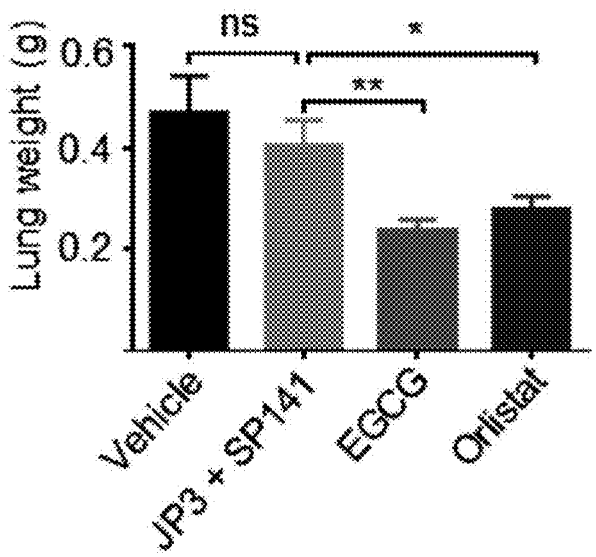
Figure 21C:
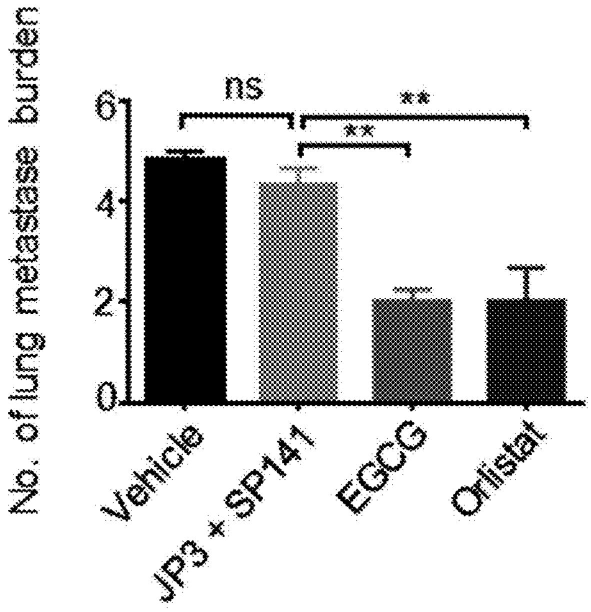

A passive metastasis model was constructed by extracting primary cells BGC823-LPC1 from residual lung metastases after joint intervention on JWA and MDM2. On the second day after injecting cells into the tail vein of the model mice, they were grouped and administered. During the medication period, they were weighed on time. At the end of the modeling, the lung wet weight of each group of mice was measured, and the situation of lung metastases was observed. The results showed (as shown in FIGS. 21A-21C) that the reduction of the lung wet weight of the mice in the intervention group continued to be treated with SP141 and JP3 was not significant compared to the solvent control group, and the reduction in the number of metastases was not significant, either. However, the FASN inhibitor EGCG group and another FASN inhibitor Orlistat group of mice showed a significant decrease in lung wet weight and a significant decrease in the number of metastatic foci, with statistical significance compared to the control group.

The results indicate that BGC823-LPC1 primary gastric cancer cells extracted from lung metastases in the SP141 and JP3 combined treatment group are re-inoculated into nude mice for modeling, followed by intervention with SP141 and JP3, however, there is little effect on inhibiting lung metastasis of gastric cancer. This indicates that the mice have developed drug resistance in the second round of model mice after receiving the first round of SP141+JP3 intervention. However, after intervention with inhibitors EGCG or Orlistat (both existing technology products) targeting the new heterogeneous molecule FASN, the lung metastasis of gastric cancer cells is significantly inhibited. This indicates that the intervention based on the algorithm proposed in the disclosure for identifying heterogeneous molecules driving tumor metastasis (i.e. the result of 1.4) is effective.

1.6 Further screening of heterogeneous molecules driving gastric cancer metastasis after sequential intervention on JWA, MDM2, and FASN On the basis of the above model, primary cells were extracted from the residual gastric cancer cells metastatic foci of the lungs of EGCG-treated mice, named BGC823-LPC2. Firstly, protein mass spectrometry analysis was continued on the residual metastatic lesions in the lungs of the EGCG group and the combined treatment group with SP141 and JP3, with a focus on observing the protein expression changes of each independent molecule identified in 1.4 above. The results showed that FASN was inhibited by 22% in the EGCG group, while the rest of the proteins were inhibited by less than 20%. As shown in FIG. 22, the heterogeneous molecules driving tumor metastasis are functionally independent from each other, and the expression level of other heterogeneous molecules remains stable after intervening one heterogeneous target molecule.

According to the strategy of identifying the heterogeneous molecular driving gastric cancer metastasis as described in section 1.4, and based on the results of the protein mass spectrometry analysis, taking into account factors such as the accessibility of inhibitors used for intervention (although many heterogeneous molecules have been screened out and theoretically intervention can be targeted at each molecule, in reality, some molecules do not have inhibitors or agonists, or are inaccessible due to high drug prices, so it is necessary to select candidate heterogeneous molecules based on the actual situation), USP9X and PFN1 oncogenes were selected as the next intervention targets. Using the TCGA database to analyze the relationship between USP9X and PFN1 and the prognosis of gastric cancer population, as shown in FIGS. 23A-23B, patients with low expression of USP9X or PFN1 have better prognosis than those with high expression.

1.7 Sequential intervention on JWA, MDM2, FASN, USP9X, PFN1 effectively inhibits in vivo metastasis of gastric cancer.

Figure 24A:
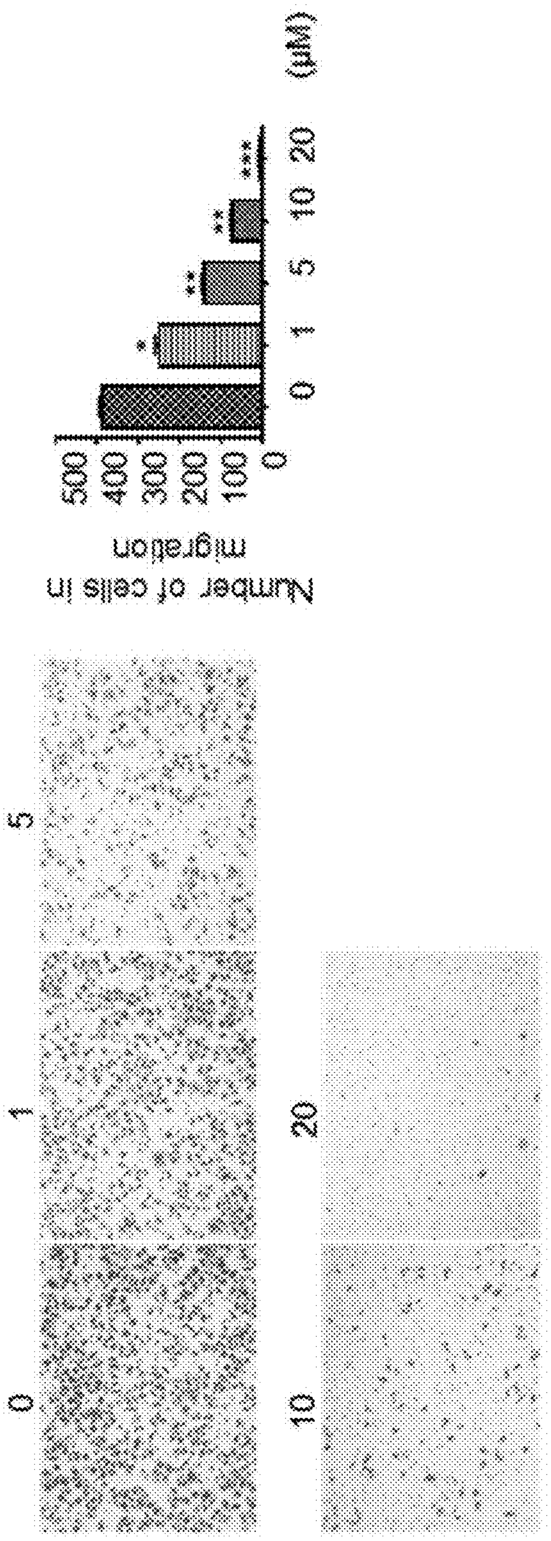
FIGS. 24A-24C, 25A-25C, and 26A-26D show sequential intervention on JWA, MDM2, FASN, USP9X, and PFN1 can effectively inhibit in vivo metastasis of gastric cancer in operations 1.7 of Example 1 of the disclosure, and each addition intervention on a heterogeneous molecule significantly delays the occurrence of gastric cancer recurrence and metastasis.
Figure 24B:
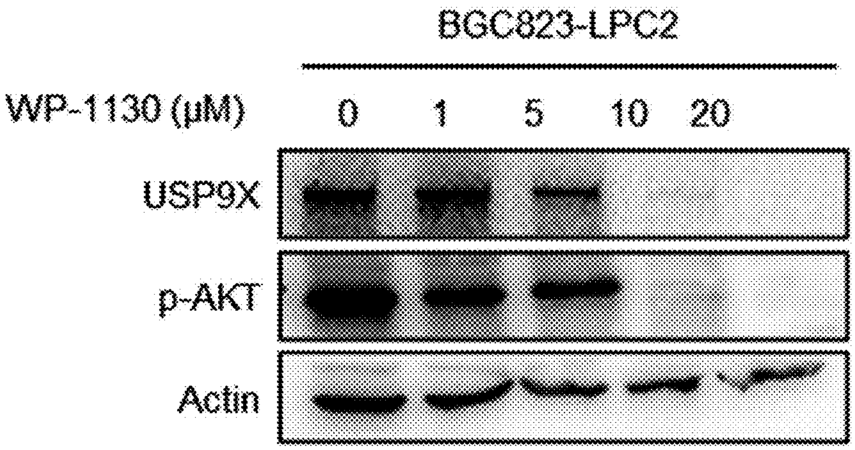
Figure 24C:
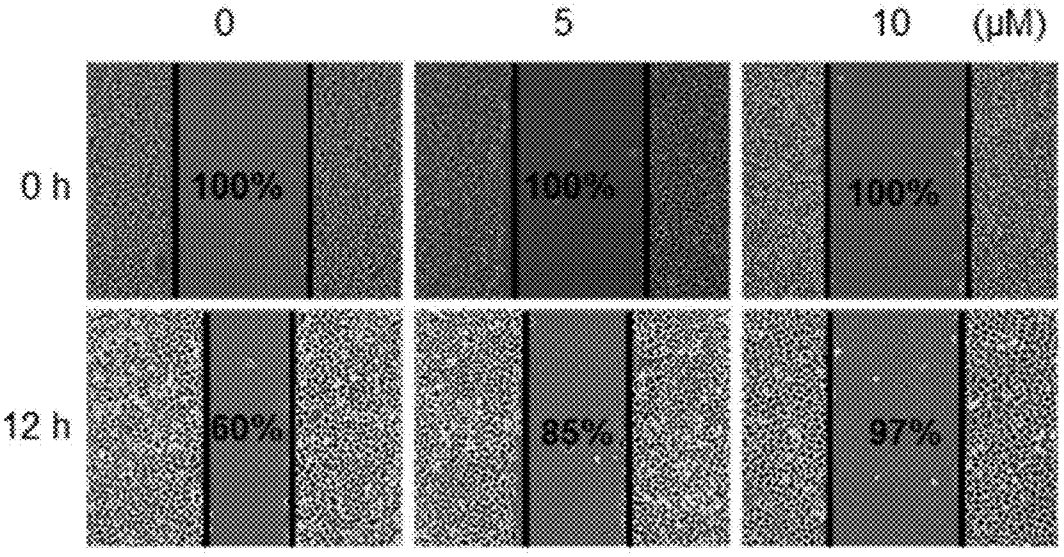

To verify the relationship between USP9X and gastric cancer metastasis, cultured BGC823 LPC2 cells were first treated with USP9X inhibitor WP-1130 (existing product) for 8 hours before a transwell experiment. The results show (as shown in FIGS. 24A-24C) that WP-1130 can significantly inhibit the number of cell perforations, and there is a dose-response relationship (FIG. 24A). The immunoblotting results showed that the expression of USP9X protein in cells treated with WP-1130 was reduced, and the transfer related protein p-AKT was also correspondingly reduced, with a dose-response relationship (FIG. 24B). The results of the scratch experiment are consistent with those of the small chamber perforation experiment (FIG. 24C). Thus, it can be seen that inhibiting the expression of USP9X can effectively reduce the migration of gastric cancer cells.

Figure 25A:
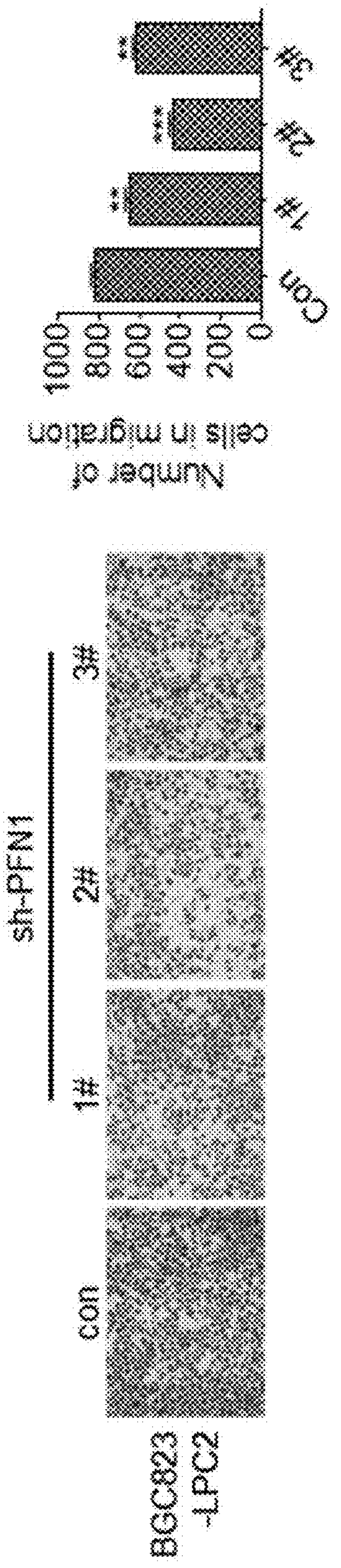
Figure 25B:
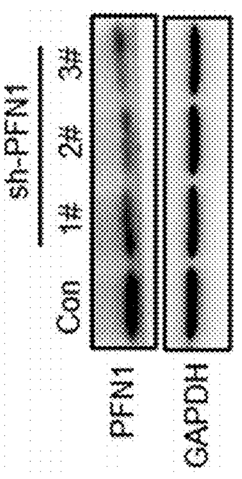
Figure 25C:
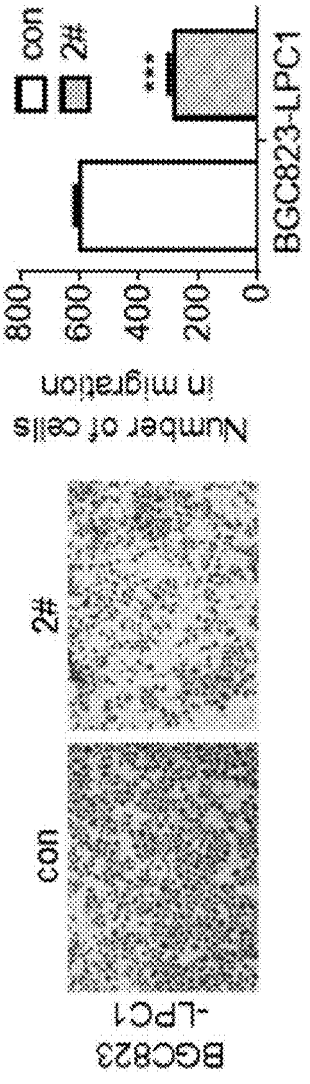

For the heterogeneous molecule PFN1, a low expression lentiviral plasmid sh-PFN1 was constructed due to the lack of commercialized inhibitor compounds. Transwell experiments were performed after transfection of sh-con and sh-PFN1 in BGC823-LPC2 for 48 hours. The results showed (FIGS. 25A-25C) that the number of perforation in gastric cancer cells with low expression of PFN1 was significantly reduced. Thus, it can be seen that interfering with PFN1 expression can effectively inhibit the migration of gastric cancer cells.

Figure 26A:
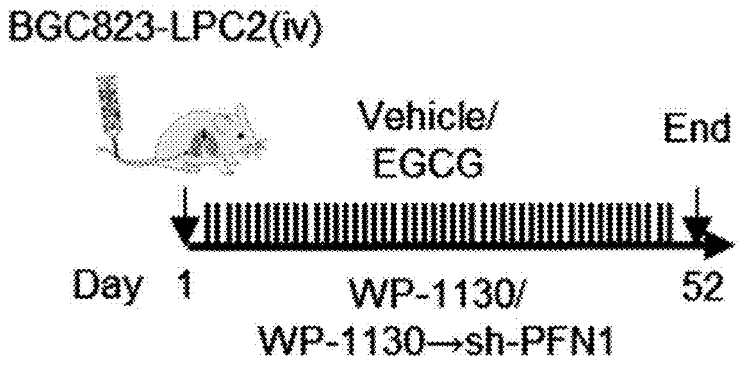
Figure 26B:
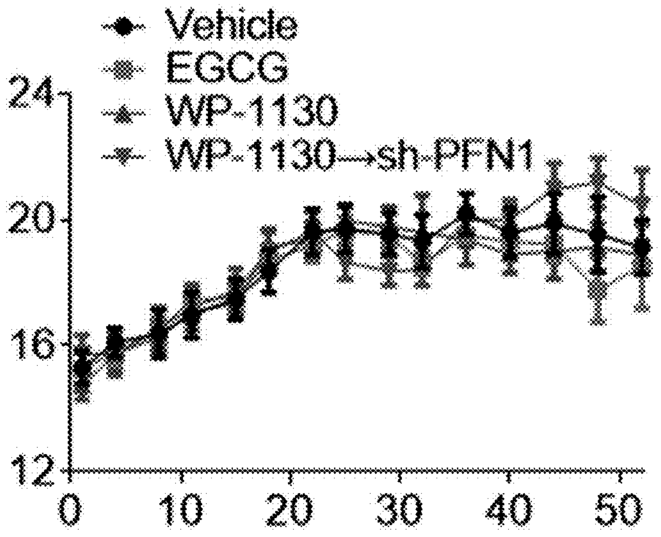
Figure 26C:
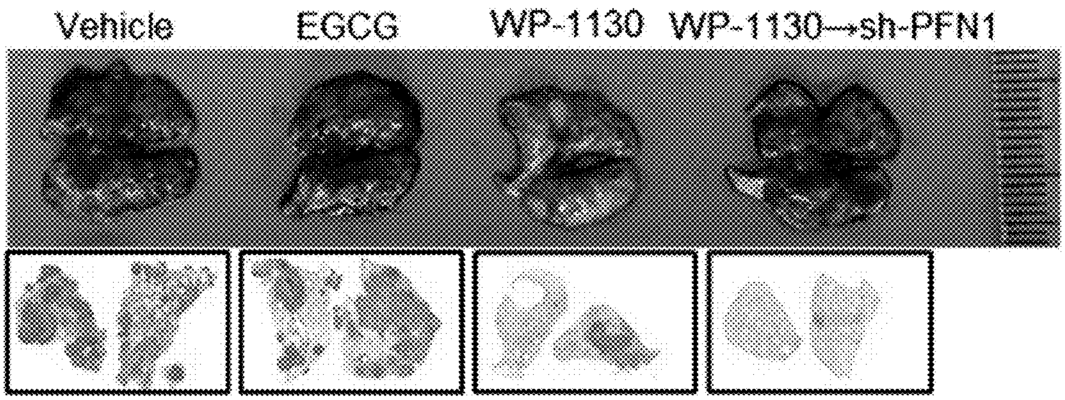
Figure 26D:
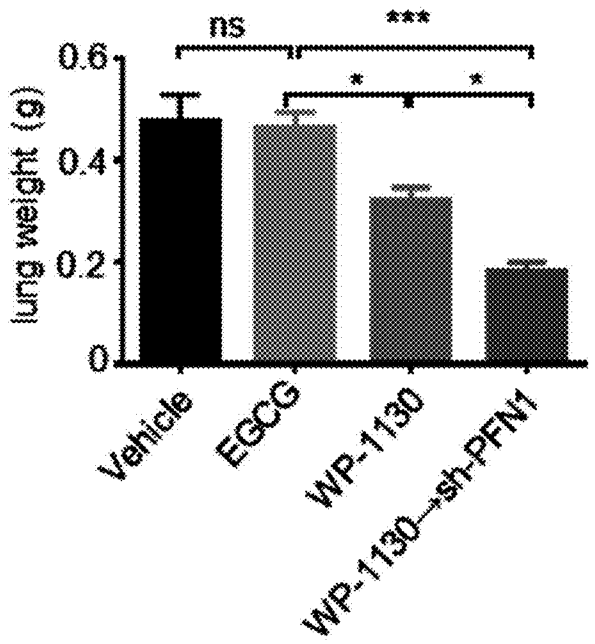
Figure 27A:
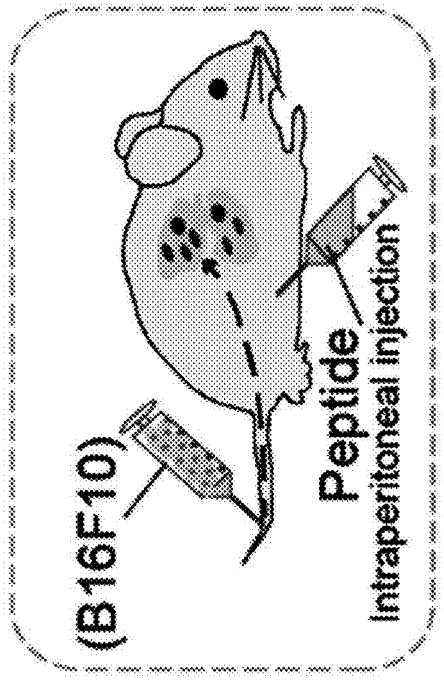
FIGS. 27A-27D and 28A-28D show JWA mimetic peptide JP1 inhibits in vivo metastasis of melanoma in operations 2.1 of Example 2 of the disclosure.
Figure 27B:
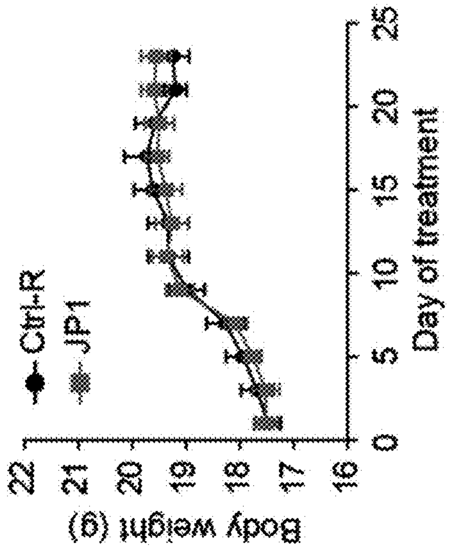
Figure 27C:
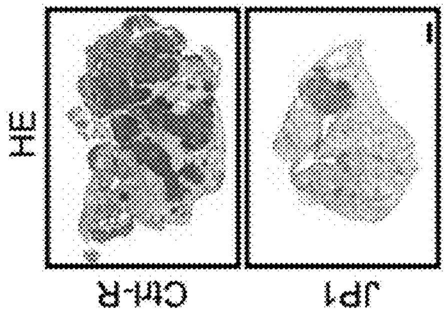
Figure 27D:
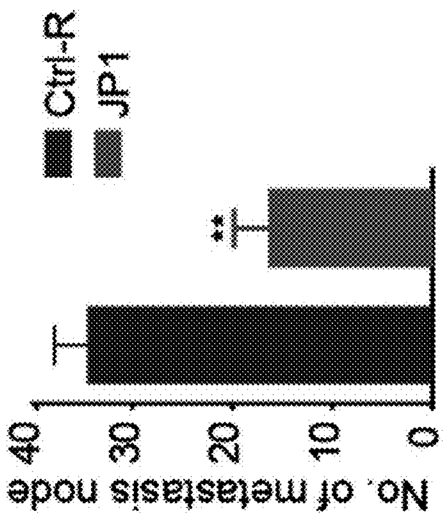
Figure 28A:
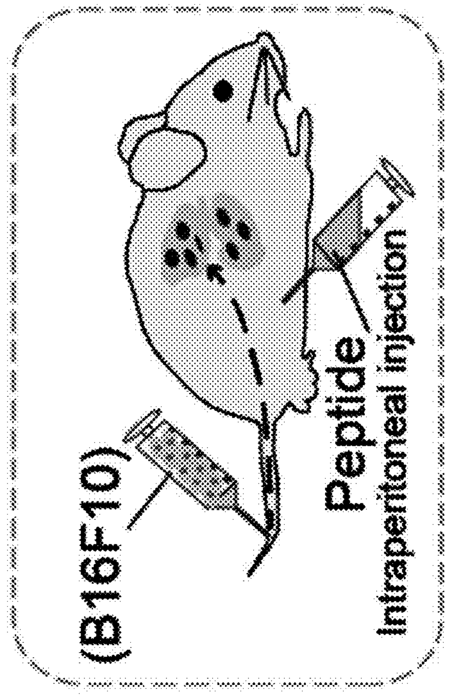
Figure 28B:
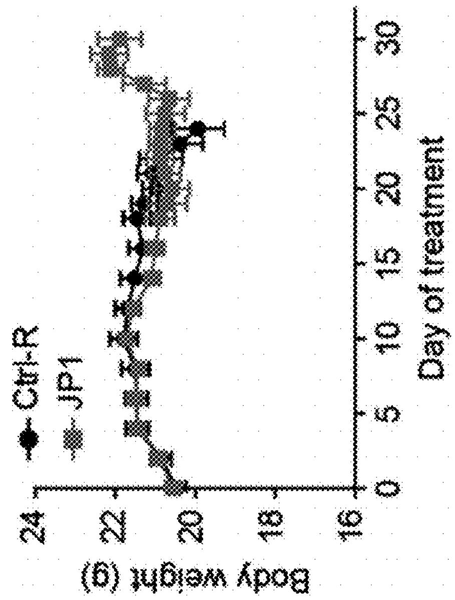
Figure 28C:
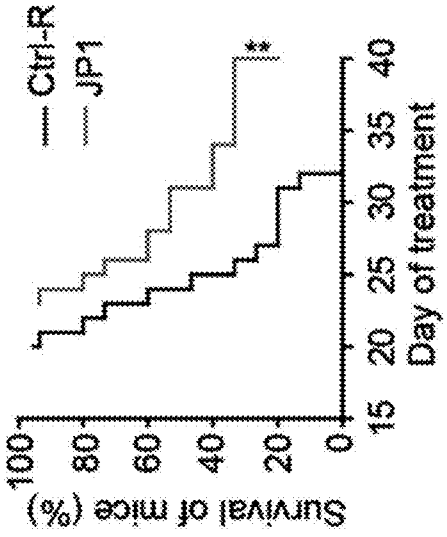
Figure 28D:
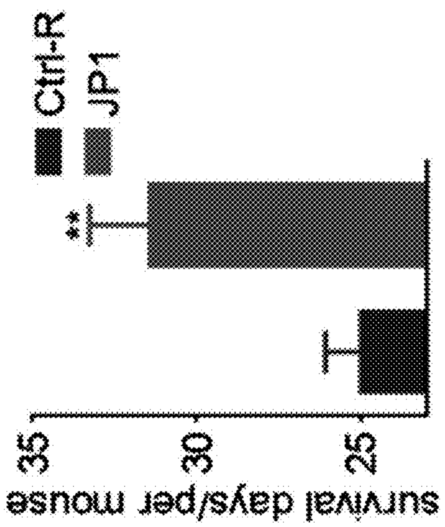
Figure 29A:
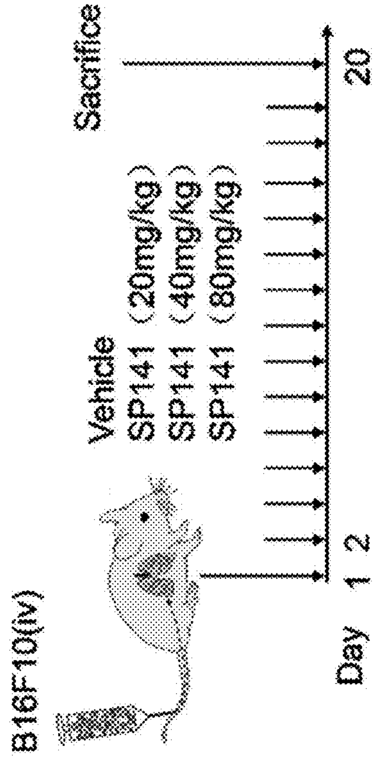
FIGS. 29A-29D shows MDM2 inhibitor SP141 inhibits in vivo metastasis of melanoma in operations 2.2 of Example 2 of the disclosure.
Figure 29B:
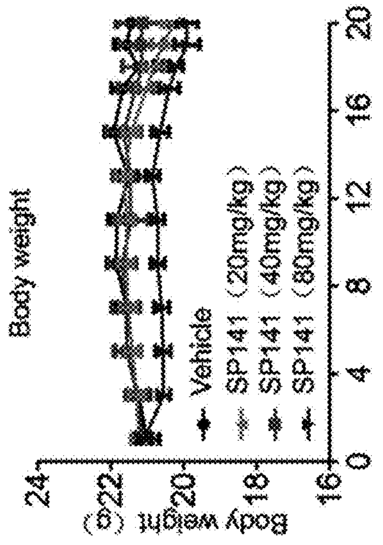
Figure 29C:
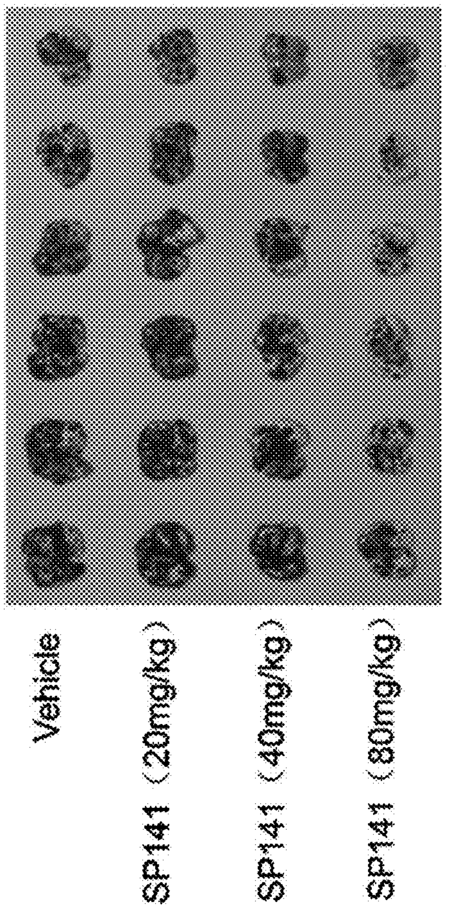
Figure 29D:
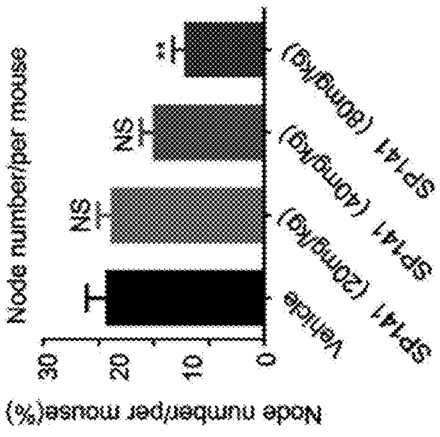

On the basis of the positive results obtained in the cell model, the animal model was then validated. A passive metastasis model was constructed using BGC823-LPC2 cells injected through the tail vein of nude mice. The mice were randomized on the second day and given control solvent, EGCG, WP-1130 alone, and WP-1130 plus sh-PFN1 lentivirus in a sequential manner. The lung metastasis of the mice was observed at the end of the modeling (FIG. 26A). Body weight observation showed that the mice gained weight steadily in the early stage and entered a plateau period on the 24th day, and the weight of the sequential group (lentiviral plasmid intervention group) increased steadily on the 40th day, while the weight of the rest of the groups began to decrease (FIG. 26B). Compared with the solvent control group, the lung metastatic foci of the mice in the continuous EGCG intervention group did not decrease significantly, and the reduction of lung wet weight was not obvious; while the lung metastatic foci of the WP-1130 group and the sequential group decreased significantly, and the lung wet weight decreased significantly (FIGS. 26C and 26D). The sequential intervention was more effective in inhibiting tumor metastasis. Thus, as shown in FIGS. 26A-26D, the sequential intervention on JWA, MDM2, FASN, USP9X and PFN1 effectively inhibited the metastasis of gastric cancer in vivo and in vitro.

Conclusion of Example 1

The example focuses on the animal model validation for the inhibition of gastric cancer drug resistance and metastasis, and the core of the research protocol is to carry out a combined intervention with a targeted drug against two independent tumor heterogeneity molecules, and then sequence (protein mass spectrographic analysis) the residual metastatic tumor foci tissues, to screen for heterogeneous molecules driving the tumor metastasis and rank them according to the HR value, to find out the next heterogeneous molecule to be intervened on; after intervening on a new heterogeneous molecule, the residual metastatic tumor foci tissues are further sequenced and screened, and so on, until all the desired heterogeneous molecules are found out and the interventions are implemented.

To verify the sequential intervention scheme for inhibiting gastric cancer metastasis, the first round candidate molecules were JWA and MDM2. After joint intervention, protein sequencing analysis was performed on residual metastatic lesions in the lungs of experimental animals, and the third heterogeneous molecule was the fatty acid synthase FASN. A passive metastasis mouse model of gastric cancer was constructed using primary cells extracted from residual tumor metastases after joint intervention on JWA and MDM2, and sequential intervention therapy was performed with FASN inhibitors. After intervention, resequencing was performed on the residual metastatic tissue of gastric cancer in the lungs of experimental animals to find subsequent heterogeneous molecules. According to the scheme, a series of new heterogeneous molecules would be discovered. Corresponding inhibitors or agonists were selected for verification of sequential intervention based on factors such as the accessibility of heterogeneous molecules and market prices. The example focuses on gastric cancer metastasis, and subsequently, two heterogeneous molecules, USP9X and PFN1, were selected for intervention verification. Therefore, the example sequentially intervened with a total of 5 heterogeneous molecules. In a confirmatory study of sequential intervention to verify the regulation of gastric cancer metastasis by heterogeneous molecules, the effectiveness of each round of sequential intervention was evaluated based on the number and size of lung metastatic nodules.

It should be noted that in the implementation of the confirmatory model, except for JWA and MDM2, which were known to be important independent molecules for direct joint intervention, FASN, USP9X, and PFN1 selected based on factors such as the availability of intervention drugs targeting the target molecule were all independent heterogeneous molecules, and different software predicted their interaction intensity scores to be 0 (FIG. 16).

Example 2

The example relates to a systematic algorithm and verification of sequential intervention for identifying heterogeneous molecules driving melanoma metastasis.

One objective of the example is to apply the method of predicting and identifying heterogeneous molecules driving tumor metastasis of the disclosure to verify whether the heterogeneous molecules identified through the algorithm of the disclosure have independent driving functions for melanoma lung metastasis in a mouse lung metastasis model constructed using melanoma cell B16F10. Meanwhile, combining the conclusion 1.6 of the identification of heterogeneous molecules driving gastric cancer metastasis and the implementation of sequential intervention in Example 1: the heterogeneous molecules driving tumor metastasis are functionally independent of each other; intervention of one heterogeneous target molecule has no effect on the stable expression levels of other heterogeneous molecules, the example further optimize the identifying and screening scheme of heterogeneous molecules driving tumor metastasis, and validate the effectiveness of the optimization scheme in the model.

2.1 Mimetic peptide JP1 of JWA inhibits in vivo metastasis of melanoma

A passive metastasis model was constructed by injecting B16F10 melanoma cells into the tail vein of mice. On the second day of cell inoculation, the mice were grouped, and Ctrl-R or JP1 peptides were injected intraperitoneally for intervention. As shown in FIGS. 27A-27D, compared to the Ctrl-R group, the JP1 intervention group significantly inhibited melanoma lung metastasis, and the difference was statistically significant. Note: Ctrl-R peptide and JP1 peptide can be found in Cui J, et al. Theranotics 2020; 10 (18): Recorded in 8036-8050.

To verify the effect of JP1 intervention on mouse survival, a B16F10 cell tail vein injection lung metastasis survival model was constructed. On the second day after tail vein injection of B16F10 cells, mice were randomly divided according to body weight and given daily intraperitoneal injection of Ctrl-R or JP1 intervention. As shown in FIGS. 28A-28D, compared to the Ctrl-R group, JP1 intervention significantly prolonged the survival period of mice with lung metastasis. The average survival days of mice in the Ctrl-R group and JP1 intervention group were 25 days and 32 days, respectively, with statistically significant differences. Conclusion: Intervention with JWA mimetic peptide JP1 can effectively inhibit in vivo metastasis of melanoma.

2.2 MDM2 inhibitor SP141 inhibits in vivo metastasis of melanoma

A passive metastatic mouse model was constructed using B16F10 cells. On the second day of cell inoculation, different doses of SP141 were used for intervention. At the end of the modeling, the number of metastatic nodules in the lungs was recorded. As shown in FIGS. 29A-29D, SP141 can inhibit the lung metastasis of melanoma in mice, and there is a dose-response relationship. Compared with the control group, the difference data of the 80 mg/kg group was statistically significant. Conclusion: inhibition of MDM2 by SP141 can effectively reduce in vivo metastasis of melanoma in mice.

2.3 Based on the characteristic that JWA and MDM2 were two functionally independent heterogeneous molecules, a synergistic inhibition model for in vitro and in vivo metastasis of melanoma was constructed.

Figure 30A:
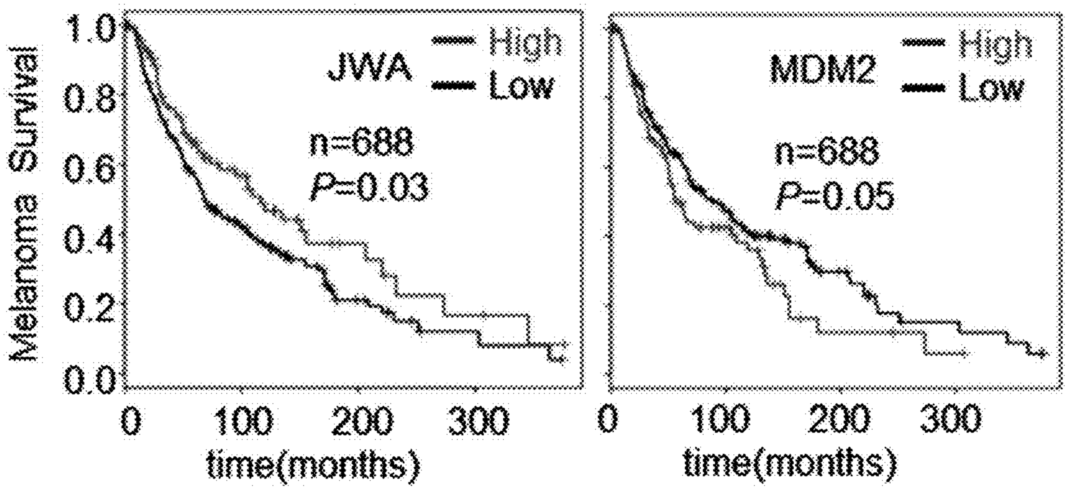
FIGS. 30A-30C and 31A-31F show JWA and MDM2 are functionally independent heterogeneous molecules that can synergistically inhibit the in vitro and in vivo metastasis of melanoma in operations 2.3 of Example 2 of the disclosure.
Figure 30B:
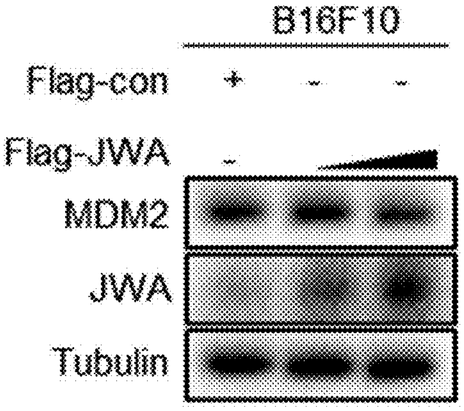
Figure 30C:
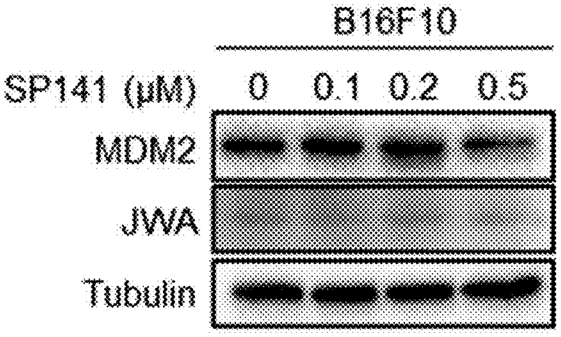
Figure 31A:
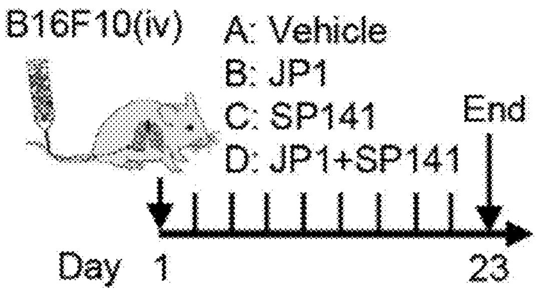
Figure 31B:
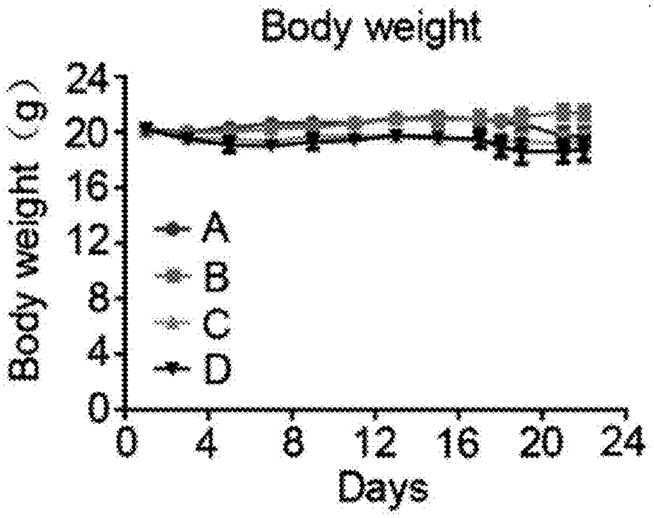
Figure 31C:
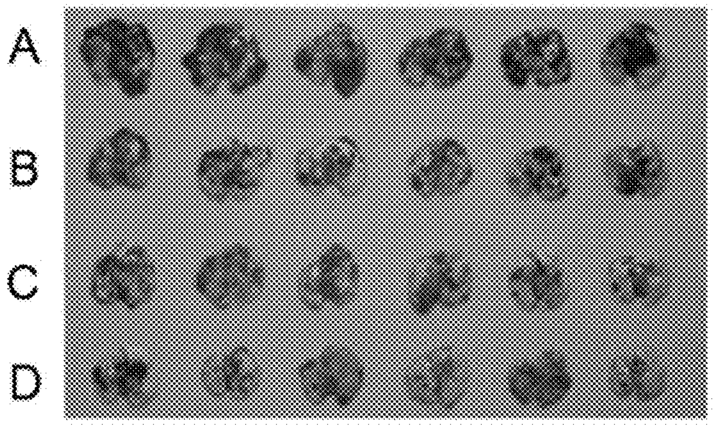
Figure 31D:
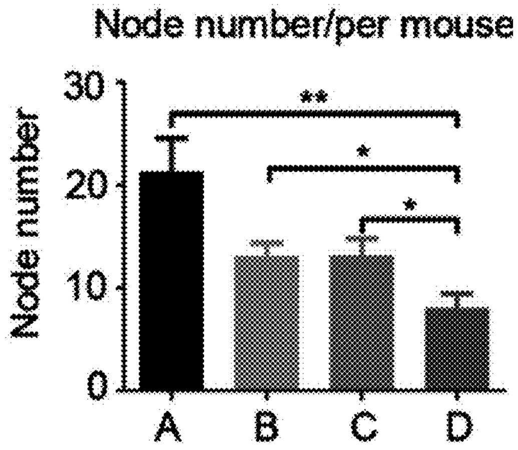
Figure 31E:
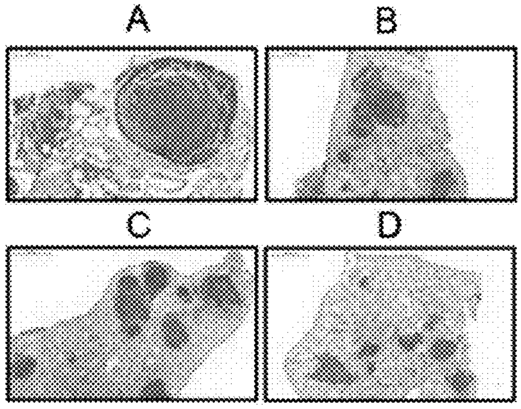
Figure 31F:
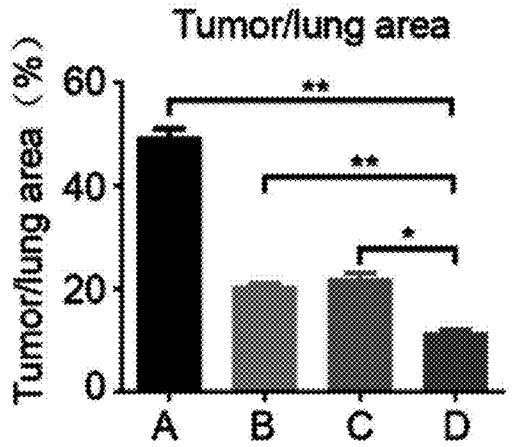

The relationship between the expression levels of JWA and MDM2 genes and the prognosis of melanoma population was analyzed using the TCGA database. The results showed that patients with high expression of JWA had significantly longer survival time than those with low expression. The survival time of MDM2 low expression patients was significantly longer than that of high expression patients. To analyze the relationship between the expression levels of the two molecular proteins and the malignant phenotype of B16F10 cells, different amounts of Flag JWA plasmids were transfected into B16F10 cells, and the JWA protein level was gradually increased, but there was no significant change in the MDM2 protein expression level. Meanwhile, melanoma cells B16F10 were treated respectively with 0, 0.25, 0.5 μM SP141 for 24 hours, and the protein expression levels of MDM2 and JWA were measured. It was found that the protein expression level of MDM2 decreased with increasing SP141 dose, but there was no significant change in JWA protein expression level. From the results, it can be seen that as shown in FIGS. 30A-30C, as far as melanoma is concerned, JWA and MDM2 do not have a mutually regulatory relationship at the protein level and are functionally independent heterogeneous molecules.

The mouse model validation was further carried out on the basis of cell model validation. A lung metastasis model with B16F10 cell tail vein injection was constructed, and on the second day, the mice were randomly grouped according to their body weight for drug intervention. As shown in FIGS. 31A-31F, the joint intervention of JWA and MDM2 has a synergistic inhibitory effect on the in vivo metastasis of melanoma. Conclusion: the joint intervention of heterogeneous molecules JWA and MDM2 driving melanoma metastasis has a synergistic effect in inhibiting melanoma lung metastasis.

2.4 after joint intervention on JWA and MDM2, although the melanoma lung metastasis in mice was significantly inhibited, the mice ultimately died from lung metastasis. In this regard, other heterogeneous molecules driving melanoma metastasis in the lungs were further screened and identified after joint intervention on the residual metastatic lesions of melanoma.

Figure 32:
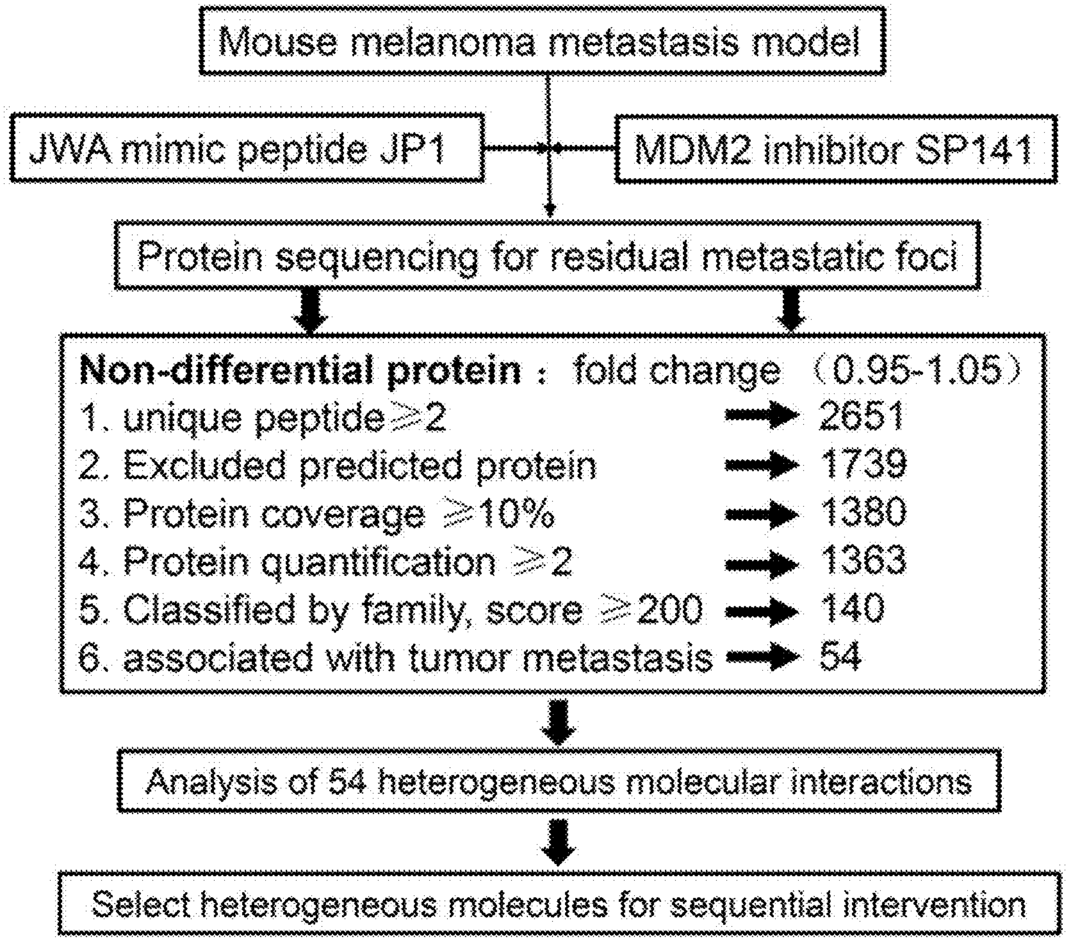
Figure 34A:
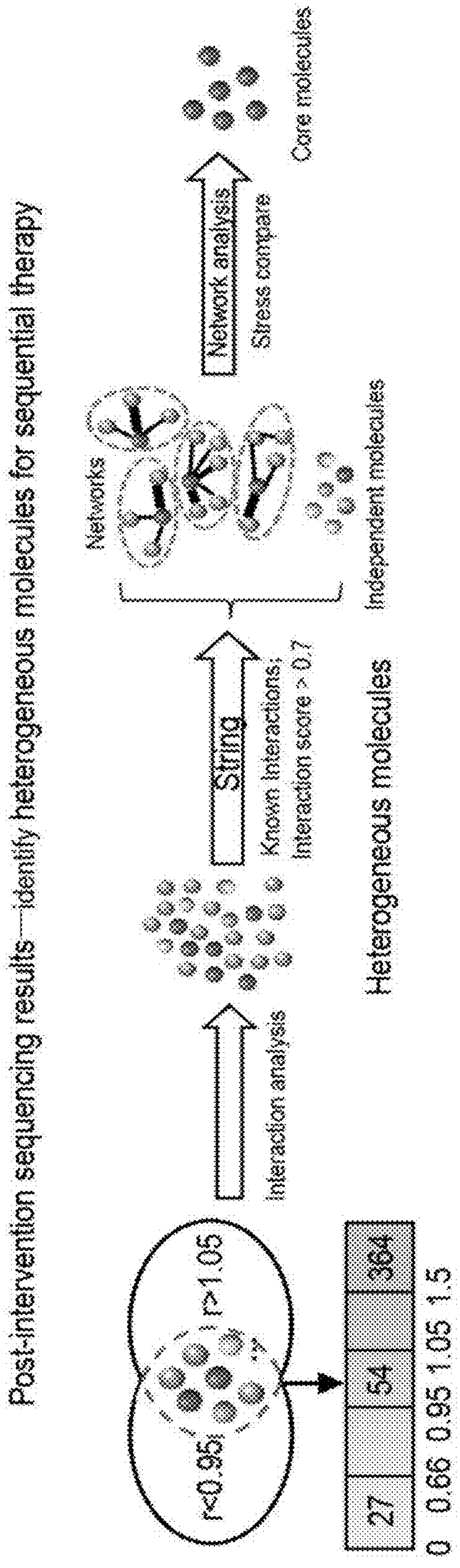
Figure 34B:
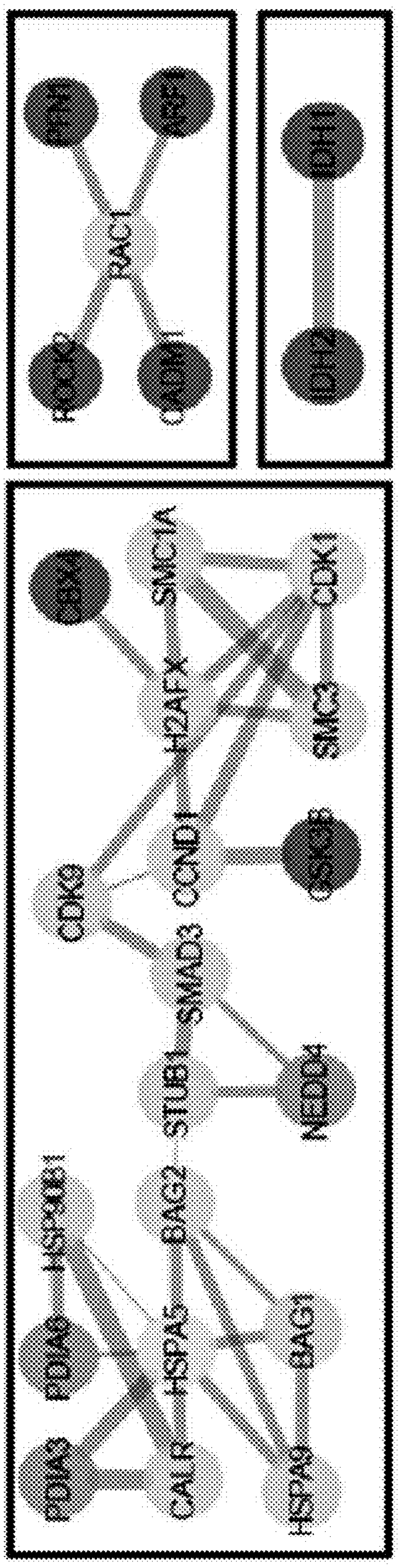
Figure 34C:
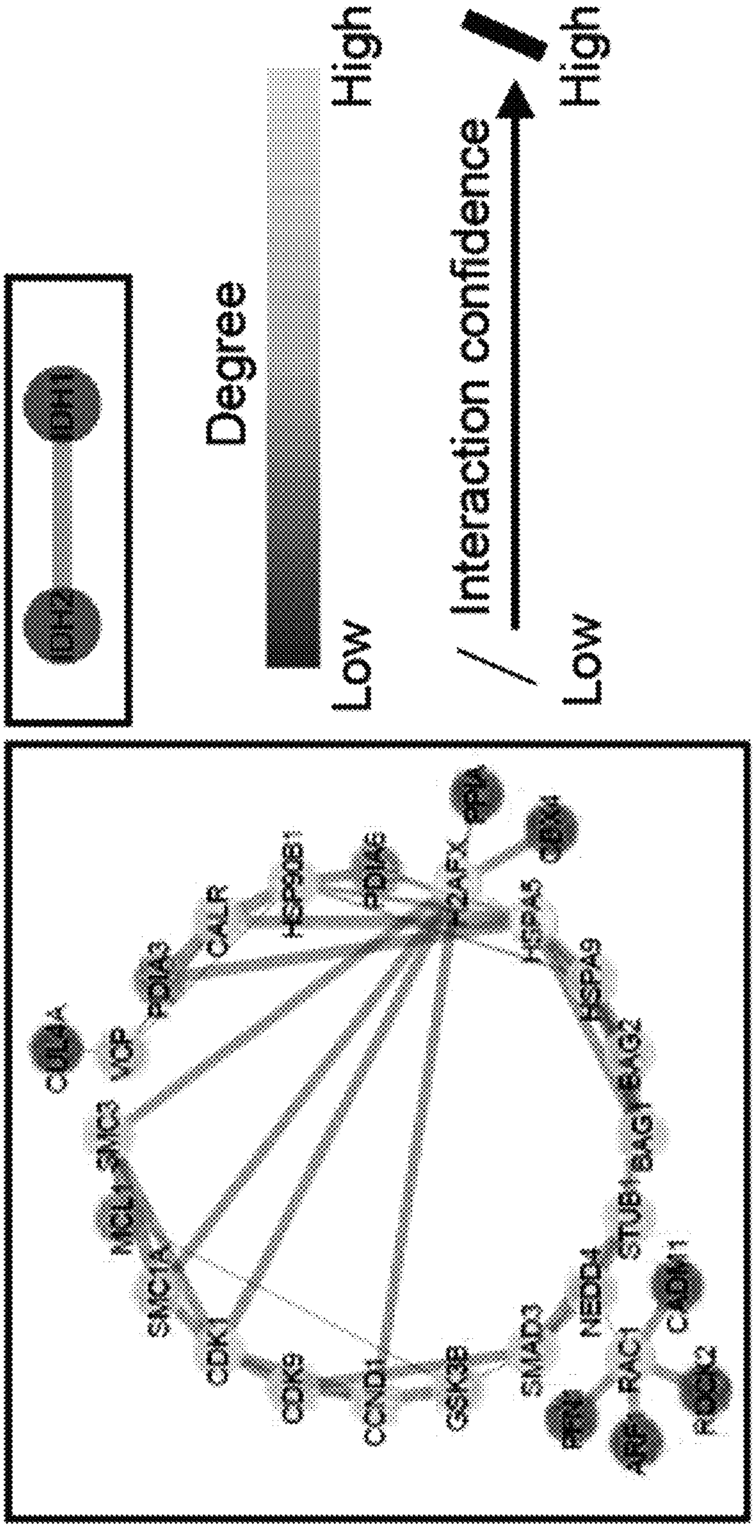
Figure 34D:
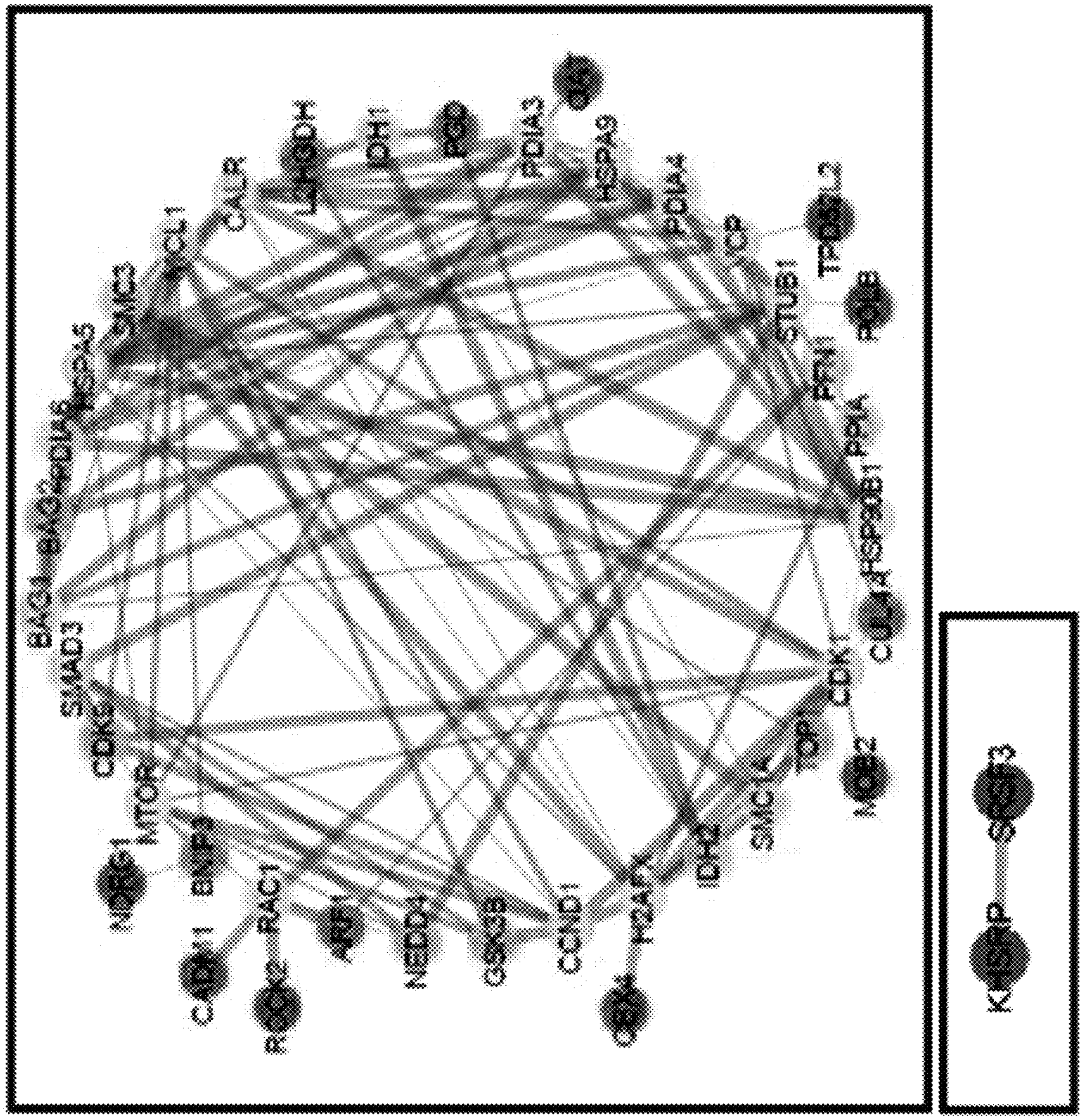
Figure 36:
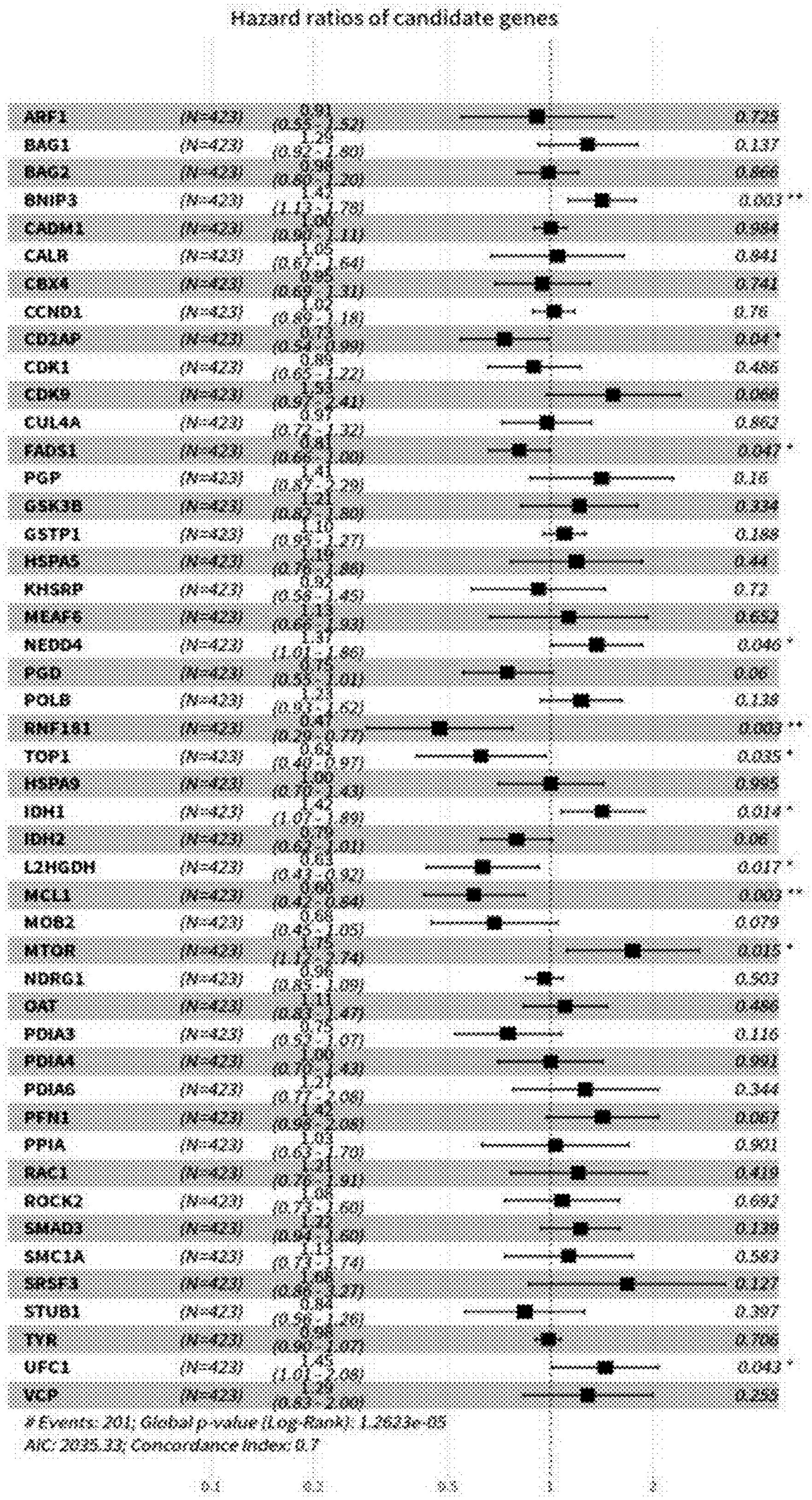
Figure 37:
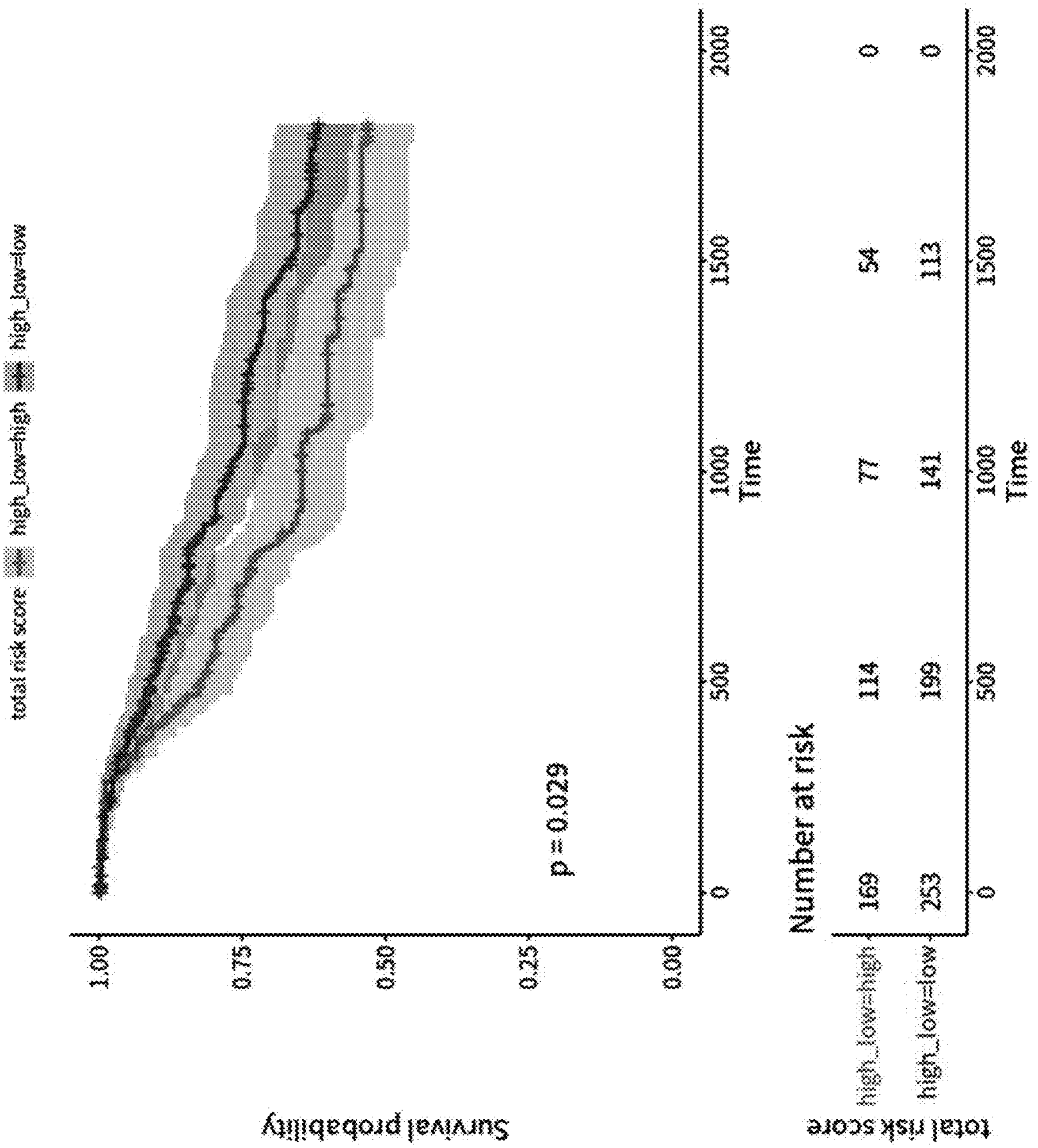

The joint intervention of JWA and MDM2 enhanced the inhibitory effect on melanoma metastasis, but due to the presence of heterogeneous molecules in melanoma cells that were not regulated by JWA and MDM2, there were still molecules driving the progression of melanoma after the joint intervention. Protein mass spectrometry analysis was performed on residual metastatic lesions in the lungs of mice after joint intervention with JP1 and SP141, and a total of over 7000 proteins were quantitatively analyzed, and protein molecules with stable expression levels (within the range of 0.95-1.05) were selected compared to the control group. The heterogeneous molecules were further screened according to the following principles: (1) specific peptide segments ≥2, totaling 2651 molecules; (2) remove predicted protein molecules from mass spectrometry analysis results; (3) remove molecules with less than 10% coverage of identified peptide segments in the protein; (4) retain molecules with protein quantification exceeding twice; (5) retain numerators with a comprehensive score exceeding 200; (6) confirmed 54 protein molecules related to tumor progression, as shown in FIG. 32. FIGS. 33A-33C and FIGS. 42A-42C list the relevant information of each candidate protein molecule.

A series of bioinformatics related analyses were conducted on the 54 molecules, similar to the process described in 1.4 of Example 1. Initial interaction networks were constructed based on experimental data and protein interaction patterns, respectively, to obtain the modifiable heterogeneous molecules in melanoma: SMAD3, IDH1/IDH2, mTOR, KHSRP/SRSF3, PGD, POLB, TOP1, L2HGDH, MOB2, PDIA4, CD2AP, FADS1, PGP, GSTP1, MAPAK3, MAPAK4, MEAF6, RNF181, D54, ITGA4, TYR, UFC1, NDRG1, OAT (FIGS. 34A-38H).

Calculate the HR value of each molecule and determine the order in which heterogeneous molecules can intervene in sequential treatment of melanoma as follows: RNF181 (0.47 (0.29-0.77), p=0.003), mTOR (1.75 (1.12-2.74), p=0.015), SRSF3 (1.68 (0.86-3.27), p=0.127) TOP1 (0.62 (0.40-0.97), p=0.035), L2HGDH (0.63 (0.43-0.92), p=0.017), MOB2 (0.68 (0.45-1.05), p=0.079), UFC1 (1.45 (1.01-2.08), p=0.043), IDH1/2 (1.42 (1.07-1.89), p=0.014), PGP (1.41 (0.87-2.29), p=0.16), CD2AP (0.73 (0.54-0.99), p=0.04), PGD (0.75 (0.55-1.01), p=0.06), ITGA4 (0.78, p=0.066), FADS1 (0.81 (0.66-1.00), p=0.047), POLB (1.23 (0.93-1.62), p=0.138), SMAD3 (1.22 (0.94-1.60), p=0.139), MEAF6 (1.13 (0.66-1.93), p=0.652), OAT (1.11 (0.83-1.47), p=0.486) GSTP1 (1.10 (0.95-1.27), p=0.188), NDRG1 (0.96 (0.85-1.09), p=0.503), TYR (0.98 (0.90-1.07), p=0.706), PDIA4 (1.00 (0.70-1.43), p=0.991), MAP2K3 (1.00, p=0.74), MAP2K4 (1.00, p=0.87) and D54 (1.00, p=0.95) (FIGS. 34A-38H).

However, it is unknown whether the screened heterogeneous molecules have corresponding antagonists or agonists that can be used to intervene in the model. The validation comprehensively considered the possibility of using these heterogeneous molecules as target interventions. In addition to JWA and MDM2, SMAD3, IDH1/2, and mTOR were also selected as heterogeneous molecules for intervention.

It should be noted that for the weight of heterogeneous molecules, the disclosure proposes to sort them based on the HR values, and the intervention measures based on decreasing HR values may theoretically be the best. However, the actual contribution of molecules with different HR values to tumor progression may be influenced by the dynamic changes in big data. As data accumulates, the HR values of the same molecule may change. Therefore, the HR value is a relative reference value. Since the intervenable molecules obtained by the prediction system are independent of each other, it can be considered that intervening in any one of the molecules (with interaction or independent molecules) is effective. In practical work, factors such as the availability and price of heterogeneous molecular drugs can be comprehensively considered and decided based on the order of HR values. For example, in the confirmatory model, the target molecules for sequential intervention in melanoma metastasis are JWA, MDM2, SMAD3, IDH1/2, mTOR in sequence. Although the decreasing order of HR values is not fully followed, the intervention results are effective.

Figure 39A:
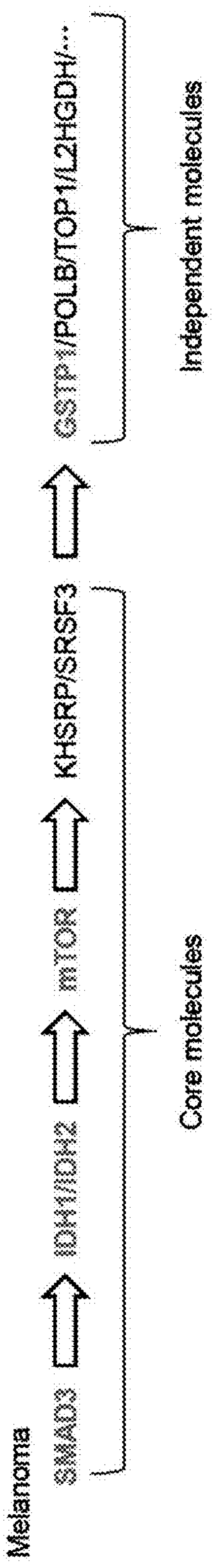
Figure 39B:
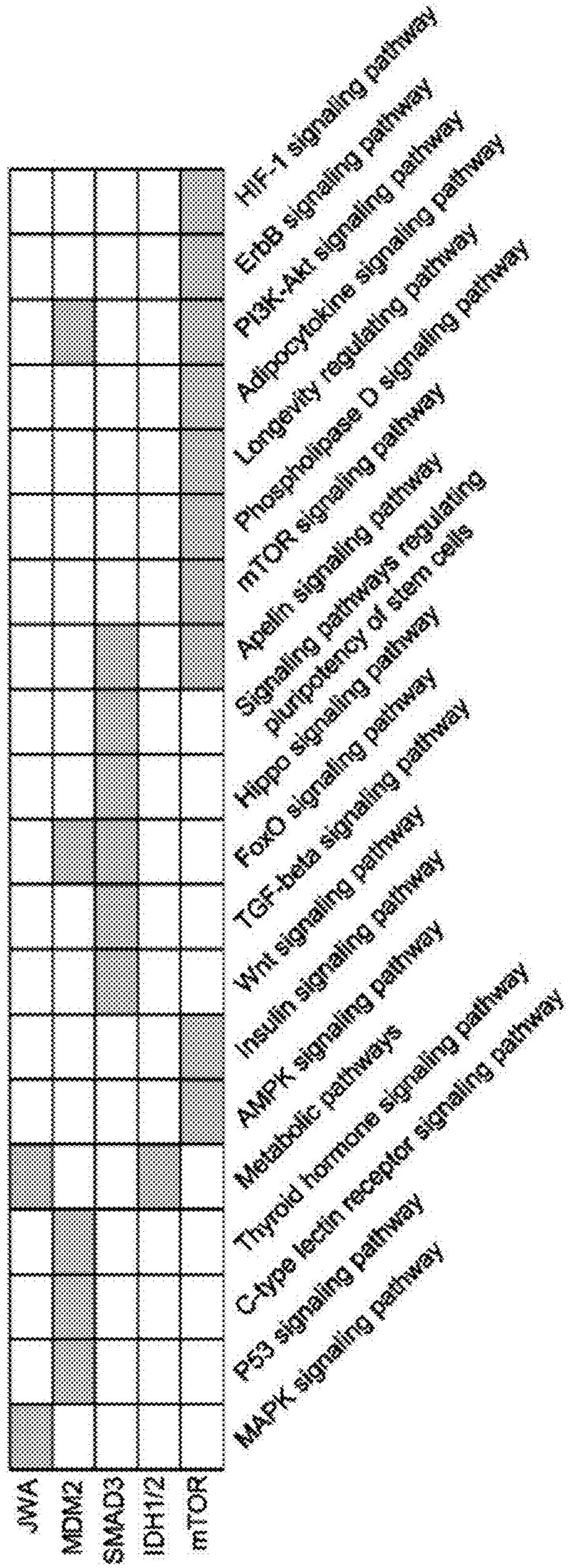

Subsequently, pathway analysis was performed on the 5 molecules, as shown in FIGS. 39A-39B. There is indeed a significant difference in the signal networks where the 5 molecules function in tumors, and they are functionally independent heterogeneous molecules.

Figure 40:
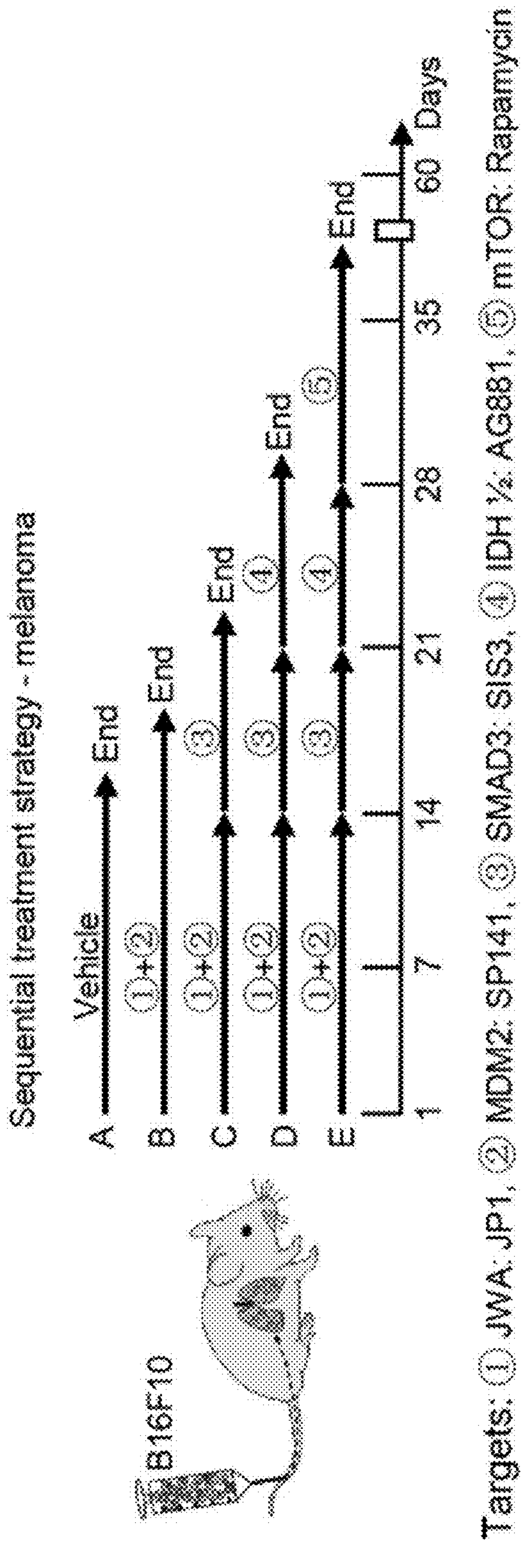
FIGS. 40 and 41A-41F show sequential intervention on JWA, MDM2, SMAD3, IDH1/2, and mTOR can effectively inhibit in vivo metastasis of melanoma in operations 2.5 of Example 2 of the disclosure.

2.5 Sequential intervention on JWA, MDM2, SMAD3, IDH1/2, mTOR effectively inhibits in vivo metastasis of melanoma Based on the screened 5 target molecules, a 4-stage sequential intervention plan was developed for melanoma metastasis model mice, as shown in FIG. 40. In the first stage, JWA and MDM2 (JP1 and SP141) were targeted for intervention from day 1 to day 14; in the second phase, targeted intervention was performed on SMAD3 (SIS3) from day 15 to day 21; in the third phase, targeted intervention was performed on IDH1/2 (AG881) from day 22 to day 28; in the fourth stage, from day 29 to the end of the model, targeted intervention was performed on mTOR (Rapamycin). Each stage of intervention was evaluated by using the previous stage model mice as a control group with continued drug use. Note: JP1 and SP141 are the same as before, while SIS3, AG881, and Rapamycin are all existing products.

Figure 41A:
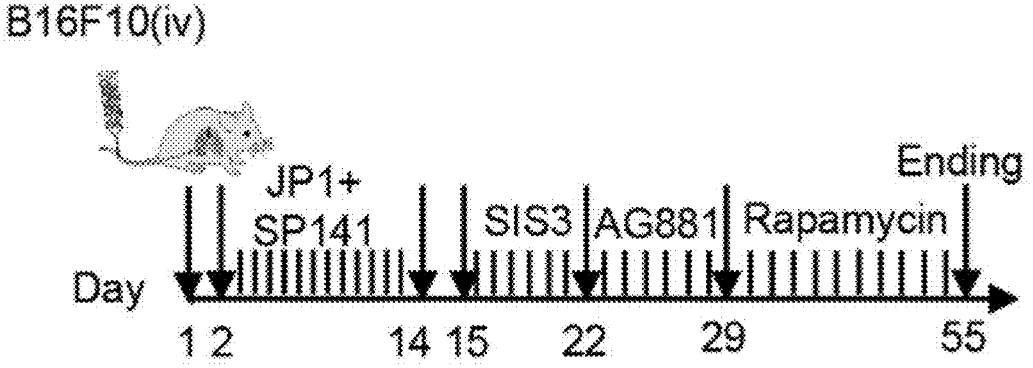
Figure 41B:
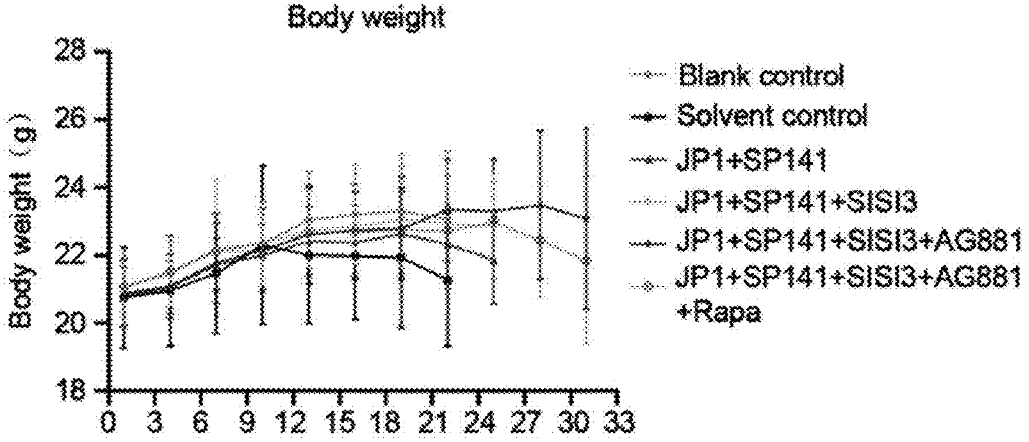
Figure 41C:
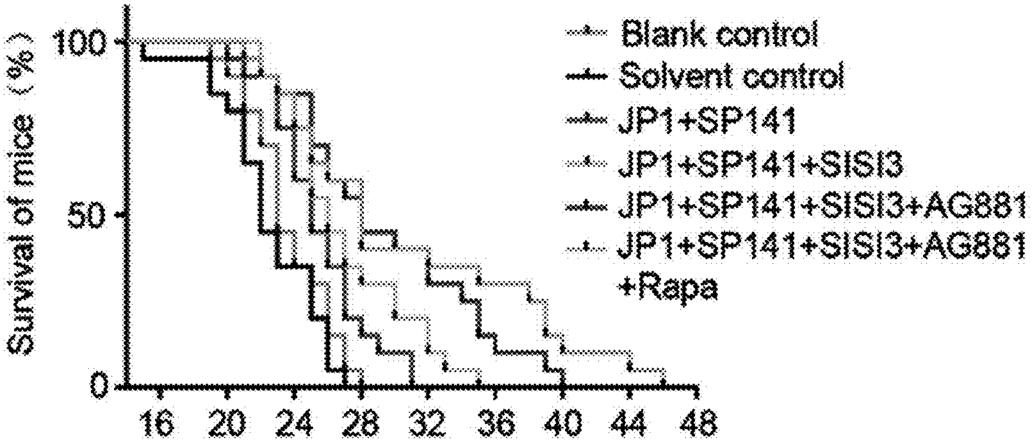
Figure 41D:
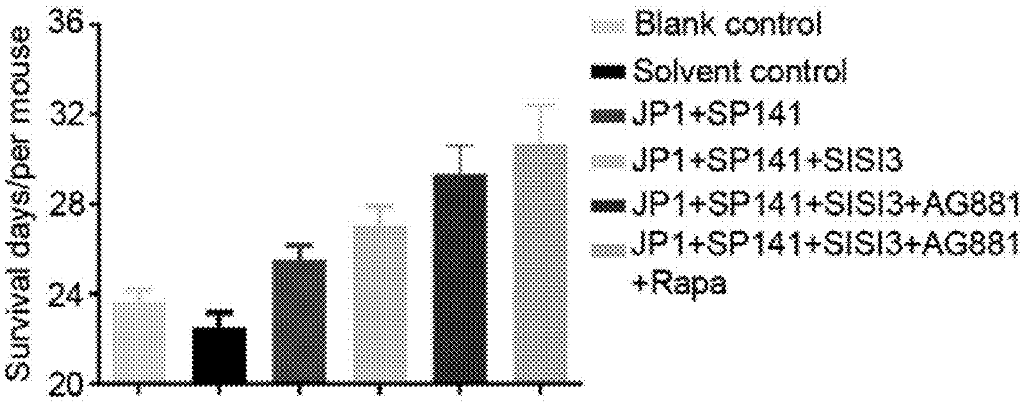
Figure 41E:
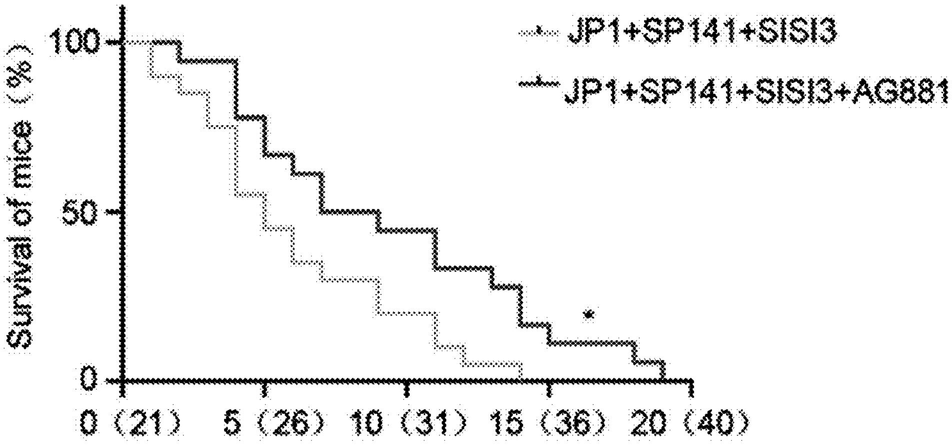
Figure 41F:
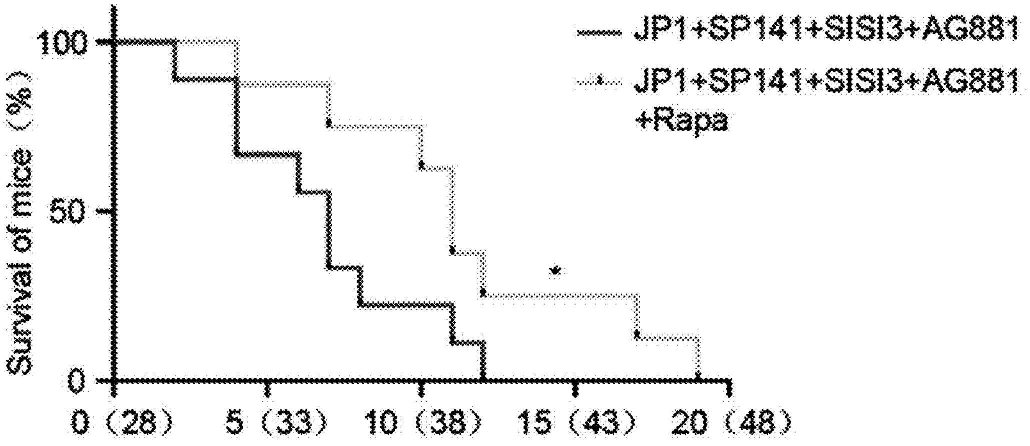

B16F10 cells were injected into the tail vein of lung metastasis mice to construct a survival model, and the mice were randomly grouped according to their body weight after tail vein injection. The drug was administered from the 2nd day. The results showed (as shown in FIGS. 41A-41F): the average survival days of mice in the control group, JP1+SP141 sequential intervention group, JP1+SP141+SIS3 sequential intervention group, JP1+SP141+SIS3+AG881 sequential intervention group, and P1+SP141+SIS3+AG881+Rapamycin sequential intervention group were 22.5, 25.55, 27.05, 29.35, and 30.7 days, respectively (FIG. 41D). The effects of the 3rd intervention of JP1+SP141+SIS3 versus the 4th intervention of JP1+SP141+SIS3+AG881 and the 4th intervention of JP1+SP141+SIS3+AG881 versus the 5th intervention of JP1+SP141+SIS3+AG881+Rapamycin on the survival of the mice were compared individually as shown in FIGS. 41E-41F, the survival time of mice increased significantly with each additional round of intervention compared with the control group, and the difference was statistically significant.

Conclusion of Example 2

To enhance the feasibility of the achievements of the disclosure in future drug development and clinical application, the strategy for screening heterogeneous molecules was further optimized in the sequential intervention confirmatory studies to inhibit melanoma metastasis. Specifically, in the gastric cancer confirmatory studies, the strategy for screening heterogeneous molecules was optimized from resequencing predicted heterogeneous molecules after each intervention to predicting all heterogeneous molecules in residual metastatic lesions with the first round of intervention as the basis for subsequent interventions. If the method is feasible, it greatly simplifies the process of identifying and predicting heterogeneous molecules, and will inevitably improve the feasibility of promotion and application. For melanoma, previous studies have shown that the expression level of JWA is significantly lower than that of para-carcinoma tissues, while the expression level of MDM2 is significantly higher than that of para-carcinoma tissues. Moreover, JWA and MDM2 are two independent heterogeneous molecules. In a confirmatory experimental model, after a joint intervention on two heterogeneous molecules, JWA and MDM2, residual metastatic foci from mouse lungs was extracted for high-throughput protein sequencing, and the heterogeneous molecules SMAD3, IDH1/2, and mTOR were identified and used for subsequent three rounds of sequential intervention, respectively.

In validating the sequential interventions for heterogeneous molecules driving melanoma metastasis, survival rates associated with lung metastases were used to judge the effectiveness of each round of sequential interventions.

It should be noted that in the confirmatory model for inhibiting melanoma metastasis, JWA and MDM2 are known independent molecules and are directly used for joint intervention, and the other three molecules, SMAD3, IDH1/2, and mTOR, predicted by different software for their interaction strength, are molecules with high interaction strength scores that exist in independent interaction networks (FIGS. 35A-35B).

It will be obvious to those skilled in the art that changes and modifications may be made, and therefore, the aim in the appended claims is to cover all such changes and modifications.

What is claimed is:

1. A method for inhibiting in vivo tumor metastasis within a patient, the method comprising:

A) identifying key heterogeneous molecules driving that drive tumor metastasis by using a prediction system to obtain a sorted list of heterogeneous molecules, the prediction system comprising a non-transitory computer readable storage medium having computer instructions stored in the medium and a processor for executing the computer instructions, identifying the key heterogeneous molecules that drive tumor metastasis by using the prediction system to obtain a sorted list of heterogeneous molecules comprising:

(1) inputting a first quantitative analysis result of proteins and a second quantitative analysis result of proteins to the prediction system; the first quantitative analysis result of proteins is a collection of quantitative analysis results of various protein expression levels in tumor metastases of the patient before drug intervention, and the second quantitative analysis result of proteins is a collection of quantitative analysis results of various protein expression levels in residual tumor metastases of the patient after drug intervention;

(2) comparing, by using the prediction system, the first quantitative analysis result of proteins and the second quantitative analysis result of proteins, and including proteins with expression changes within a predetermined range in a candidate protein set;

(3) constructing, by using the prediction system to employ a protein interaction network analysis tool, experimentally validated protein interaction networks based on the candidate protein set, supplementing the protein interaction networks by utilizing signal pathways of the candidate protein; including most important proteins in each protein interaction network as independent heterogeneous molecules in an independent molecular set; constructing, by using the prediction system to employ a protein interaction network prediction tool and based on the candidate protein set, a protein interaction prediction network according to a protein interaction law; and including proteins in the candidate protein set that do not participate in any protein interaction prediction network as independent heterogeneous molecules in the independent molecular set; and (4) calculating, by using the prediction system, a hazard ratio (HR) value of each heterogeneous molecule in the independent molecular set, and sorting the heterogeneous molecules based on the HR value, to form the sorted list of heterogeneous molecules; and B) conducting a sequential intervention on the heterogeneous molecules within the patient by administering to the patient, in sequence, inhibitors or agonists that respectively target the heterogeneous molecules according to an order in the sorted list of heterogeneous molecules, thereby inhibiting in vivo tumor metastasis within the patient.

2. The method of claim 1, wherein the first quantitative analysis result of proteins and the second quantitative analysis result of proteins are acquired through high-throughput protein sequencing; and the high-throughput protein sequencing comprises protein mass spectrometry analysis.

3. The method of claim 1, wherein the proteins with expression changes within the predetermined range are proteins whose expression levels after drug intervention are 0.95-1.05 times higher than those before drug intervention.

4. The method of claim 1, wherein the proteins with expression changes within the predetermined range are first screened and then included in the candidate protein set; the proteins that are screened meet the following conditions: a number of specific peptide segments is ≥2, and is not a predicted protein; a coverage of amino acids of identified peptide segments of a current protein is ≥10%; a quantification frequency of the current protein is ≥2, and a sequencing quality comprehensive score of the current protein is ≥200; evidence in a database shows the current protein is related to tumor progression; the specific peptide segments refer to a specific peptide segment used to identify the current protein; the predicted protein refers to an attribute that defines a reliability of the current protein in Uniport or National Center for Biotechnology Information (NCBI) databases as a predicted protein; the identified peptide segments refer to a specific peptide segment that can be used to indicate the current protein being detected; the quantification frequency of the current protein refers to a number of repetitions of the current protein being quantitatively detected.

5. The method of claim 1, wherein the protein interaction network analysis tool comprises a STRING network tool; the system further comprises a signal pathway database for accessing the signal pathways of the candidate protein, and the signal pathway database comprises Kyoto Encyclopedia of Genes and Genomes (KEGG), Small Molecule Pathway Database (SMPDB), WikiPathways, Cell Signaling Technology, BioCarta Pathway, Pathway Commons, and Pathway Interaction Database (PID); the protein interaction network prediction tool comprises a Gene Multiple Association Network Integration Algorithm (GeneMANIA) network tool, Unified Human Interactome (UniHI) network tool, and Hitpredict network tool.

6. The method of claim 5, wherein the system further comprises a Cytoscape tool for constructing and supplementing the protein interaction networks, and for constructing a protein interaction prediction network.

7. The method of claim 1, wherein the most important proteins in each protein interaction network are identified through characteristic analysis; the characteristic analysis comprises analyzing the importance, degree, and radiancy of each protein in the protein interaction network; and proteins with the highest importance, degree, and radiancy are the most important proteins in the protein interaction network.

8. The method of claim 1, wherein during the calculating and sorting, the HR value of each heterogeneous molecule is calculated as follows: obtaining sequencing data of tumors from a public database, obtaining a standardized counting matrix of genes corresponding to the heterogeneous molecules from the sequencing data, and performing batch single factor Cox regression on the genes to obtain the HR value.

9. The method of claim 8, wherein the public database comprises The Cancer Genome Atlas (TCGA), International Cancer Genome Consortium (ICGC), and Gene Expression Omnibus (GEO).

10. The method of claim 1, wherein during the calculating and sorting, a sorting rule is: the heterogeneous molecules with HR values greater than or equal to 1 are directly sorted in reverse order according to their HR values, and the heterogeneous molecules with HR values less than 1 are sorted in reverse order according to their 1/HR values.

* * * * *